(12) United States Patent
Chen et al.

(10) Patent No.: US 6,761,903 B2
(45) Date of Patent: **\*Jul. 13, 2004**

(54) CLEAR OIL-CONTAINING PHARMACEUTICAL COMPOSITIONS CONTAINING A THERAPEUTIC AGENT

(75) Inventors: Feng-Jing Chen, Salt Lake City, UT (US); Mahesh V. Patel, Salt Lake City, UT (US); David T. Fikstad, Salt Lake City, UT (US)

(73) Assignee: Lipocine, Inc., Salt Lake City, UT (US)

( \* ) Notice: Subject to any disclaimer, the term of this patent is extended or adjusted under 35 U.S.C. 154(b) by 30 days.

This patent is subject to a terminal disclaimer.

(21) Appl. No.: 09/877,541

(22) Filed: Jun. 8, 2001

(65) Prior Publication Data

US 2002/0032171 A1 Mar. 14, 2002

Related U.S. Application Data

(63) Continuation-in-part of application No. 09/345,615, filed on Jun. 30, 1999, now Pat. No. 6,267,985, and a continuation-in-part of application No. 09/751,968, filed on Dec. 29, 2000, now Pat. No. 6,458,383, which is a continuation-in-part of application No. 09/375,636, filed on Aug. 17, 1999, now Pat. No. 6,309,663.

(51) Int. Cl.[7] .............................. A61K 9/08; A61K 9/10; A61K 9/14; A61K 9/20; A61K 9/48
(52) U.S. Cl. .................. 424/451; 424/43; 424/433; 424/436; 424/441; 424/445; 424/455; 424/456; 424/458; 424/463; 424/464; 424/465; 424/489; 424/490; 424/725; 514/772.2; 514/772.3; 514/777; 514/779; 514/781; 514/783; 514/784; 514/785; 514/786; 514/937; 514/944
(58) Field of Search ........................ 424/451, 450, 424/433, 436, 441, 443, 445

(56) References Cited

U.S. PATENT DOCUMENTS

| | | | |
|---|---|---|---|
| 3,510,561 A | 5/1970 | Koh et al. |
| 4,156,719 A | 5/1979 | Sezaki et al. |
| 4,239,754 A | 12/1980 | Sache et al. |
| 4,388,307 A | 6/1983 | Cavanak |
| 4,572,915 A | 2/1986 | Crooks |
| 4,579,730 A | 4/1986 | Kidron et al. |
| 4,654,327 A | 3/1987 | Teng |
| 4,656,161 A | 4/1987 | Herr |
| 4,695,450 A | 9/1987 | Bauer |
| 4,703,042 A | 10/1987 | Bodor |
| 4,713,246 A | 12/1987 | Begum et al. |
| 4,719,239 A | 1/1988 | Muller et al. |
| 4,727,109 A | 2/1988 | Schmidt et al. |
| 4,731,384 A | 3/1988 | Dell et al. |
| 4,944,949 A | 7/1990 | Story et al. |
| 4,994,439 A | 2/1991 | Longenecker et al. |
| 5,071,643 A | 12/1991 | Yu et al. |
| 5,120,710 A | 6/1992 | Liedtke |
| 5,145,684 A | 9/1992 | Liversidge et al. |
| 5,206,219 A | 4/1993 | Desai |
| 5,244,925 A | 9/1993 | Wretlind et al. |
| 5,300,529 A | 4/1994 | Narayanan |
| 5,342,625 A | 8/1994 | Hauer et al. |
| 5,350,741 A | 9/1994 | Takada |
| 5,364,632 A | 11/1994 | Benita et al. |
| 5,376,688 A | 12/1994 | Morton et al. |
| 5,444,041 A | 8/1995 | Owen et al. |
| 5,500,224 A | 3/1996 | Vranckx et al. |
| 5,532,002 A | 7/1996 | Story |
| 5,589,455 A | 12/1996 | Woo |
| 5,614,491 A | 3/1997 | Walch et al. |
| 5,616,330 A | 4/1997 | Kaufman et al. |
| 5,622,721 A | 4/1997 | Dansereau et al. |
| 5,626,869 A | 5/1997 | Nyqvist et al. |
| 5,633,226 A | 5/1997 | Owen et al. |
| 5,639,474 A | 6/1997 | Woo |

(List continued on next page.)

FOREIGN PATENT DOCUMENTS

| | | |
|---|---|---|
| EP | 036145 | 9/1981 |
| WO | 84/02076 | 6/1984 |
| WO | 88/00059 | 1/1988 |
| WO | 93/06921 | 4/1993 |
| WO | 95/34287 | 12/1995 |
| WO | 96/17597 | 6/1996 |

OTHER PUBLICATIONS

Alvarez et al. (1989), "The Role of Calcium Ions and Bile Salts on the Pancreatic Lipase–Catalyzed Hydrolysis of Triglycefide Emulsions Stabilized with Lecithin," *Pharmaceutical Research* 6(6):449–457.

Aungst (2000), "Intestinal Permeation Enhancers," *Journal of Pharmaceutical Sciences* 89(4):429–442.

Baluom et al. (1998), "The Importance of Intestinal Residence Time of Absorption Enhancer on Drug Absorption and Implication on Formulative Considerations," *International Journal of Pharmaceutics* 176:21–30.

Bates et al. (1975), "Bioavailability of Micronized Griseofulvin from Corn Oil–in–Water Emulsion, Aqueous Suspension, and Commercial Tablet Dosage Forms in Humans," *Journal of Pharmaceutical Sciences* 64(5):793–797.

(List continued on next page.)

*Primary Examiner*—James M. Spear
(74) *Attorney, Agent, or Firm*—Thorpe North & Western, LLP

(57) ABSTRACT

The present invention relates to pharmaceutical compositions and methods for improved solubilization of triglycerides and improved delivery of therapeutic agents. Compositions of the present invention include a carrier, where the carrier is formed from a combination of a triglyceride and at least two surfactants, at least one of which is hydrophilic. Upon dilution with an aqueous medium, the carrier forms a clear, aqueous dispersion of the triglyceride and surfactants.

122 Claims, No Drawings

U.S. PATENT DOCUMENTS

| | | |
|---|---|---|
| 5,639,724 A | 6/1997 | Cavanak |
| 5,645,856 A | 7/1997 | Lacy et al. |
| 5,646,109 A | 7/1997 | Owen et al. |
| 5,653,987 A | 8/1997 | Modi et al. |
| 5,656,277 A | 8/1997 | Berlati et al. |
| 5,656,289 A | 8/1997 | Cho et al. |
| 5,665,379 A | 9/1997 | Herslof et al. |
| 5,686,105 A | 11/1997 | Kelm et al. |
| 5,688,761 A | 11/1997 | Owen et al. |
| 5,707,648 A | 1/1998 | Yiv |
| 5,714,477 A | 2/1998 | Einarsson |
| 5,726,181 A | 3/1998 | Hausheer et al. |
| 5,731,355 A | 3/1998 | Jones et al. |
| 5,736,161 A | 4/1998 | Garces et al. |
| 5,741,822 A | 4/1998 | Yesair |
| 5,747,066 A | 5/1998 | Pittrof et al. |
| 5,766,629 A | 6/1998 | Cho et al. |
| 5,817,320 A | 10/1998 | Stone |
| 5,853,748 A | 12/1998 | New |
| 5,858,398 A | 1/1999 | Cho |
| 5,858,401 A | 1/1999 | Bhalani et al. |
| 5,948,825 A | 9/1999 | Takahashi et al. |
| 6,267,985 B1 * | 7/2001 | Chen et al. ............... 424/451 |
| 6,309,663 B1 | 10/2001 | Patel et al. |
| 6,458,383 B2 * | 10/2002 | Chen et al. ............... 424/451 |

OTHER PUBLICATIONS

Bernkop–Schnürch (1998), "The Use of Inhibitory Agents to Overcome the Enzymatic Barrier to Perorally Administered Therapeutic Peptides and Proteins," *Journal of Controlled Release* 52:1–16.

Charman et al. (1997), "Physicochemical and Physiological Mechanisms for the Effects of Food on Drug Absorption: The Role of Lipids and pH," *Journal of Pharmaceutical Sciences* 86(3):269–282.

Gennaro (1985), *Remington's Pharmaceutical Sciences*, Chapter 20, pp. 293–300.

Hörter et al. (1997), "Influence of Physicochemical Properties on Dissolution of Drugs in the Gastrointestinal Tract," *Advanced Drug Delivery Reviews* 25:3–14.

Humberstone et al. (1977), "Lipid–Based Vehicles for the Oral Delivery of Poorly Water Soluble Drugs," *Advanced Drug Delivery Review*, pp. 103–128.

Johnson (1997), "Gastrointestinal Physiology," *C V Morby Co., St. Louis*, Houston, Texas, pp. 25–26, 93, 106, 133–134, and 136–137.

LeCluyse et al. (1997), "In Vitro Models for Selection of Development Candidates. Permeability Studies to Define Mechanisms of Absorption Enhancement," *Advanced Drug Delivery Reviews* 23:163–183.

MacGregor et al. (1997), "Influence of Lipolysis on Drug Absorption From the Gastro–Intestinal Tract," *Advanced Drug Delivery Reviews* 25:33–46.

Muranishi (1977), "Potential Absorption of Heparin from the Small Intestine and the Large Intestine in the Presence of Monoolein Mixed Micelles," *Chem. Pharm. Bull.* 24(5):1159–1161.

Muranishi (1990), "Absorption Enhancers," *Critical Reviews in Therapeutic Drug Carrier Systems* 7(1):1–33.

Pouton (1997), "Formulation of Self–Emulsifying Drug Delivery Systems," *Advanced Drug Delivery Reviews* 25:47–58.

Reymond et al., "In Vitro Model for Ciclosporin Intestinal Absorption in Lipid Vehicles," *Pharmaceutical Research* 5(10):673–676.

Schott (1990), "Comments on Hydrophile–Lipophile Balance Systems," *Journal of Pharmaceutical Sciences* 79(1):87–88.

Tarr et al. (1989), "Enhanced Intestinal Absorption of Cyclosporine in Rats Through The Reduction of Emulsion Droplet Size," *Pharmaceutical Research* 6(1):40–43 (1989).

Wilson et al. (1997), "The Behaviour of Fats and Oils in the Upper G.I. Tract," *Bulletin Technique Gattefossé* 90:13–18.

Winne (1978), "Dependence of Intestinal Absorption in Vivo on the Unstirred Layer," *Archives of Pharmacology* 304:175–181.

Zhi et al. (1995), "Effects of Dietary Fat on Drug Absorption," *Clinical Pharmacology and Therapeutics* 58(5):487–491.

* cited by examiner

CLEAR OIL-CONTAINING PHARMACEUTICAL COMPOSITIONS CONTAINING A THERAPEUTIC AGENT

CROSS REFERENCE TO RELATED APPLICATIONS

This application is a continuation-in-part of U.S. patent application Ser. No. 09/345,615, filed Jun. 30, 1999 U.S. Pat. No. 6,267,985, and a continuation-in-part of U.S. application Ser. No. 09/751,968, filed Dec. 29, 2000 U.S. Pat. No. 6,458,383, which is a continuation-in-part of U.S. application Ser. No. 09/375,636, filed Aug. 17, 1999 U.S. Pat. No. 6,309,663, the disclosures of which are hereby incorporated by reference.

TECHNICAL FIELD

The present invention relates to drug delivery, and in particular to pharmaceutical compositions and methods for the improved solubilization of both triglycerides and surfactants and improved delivery of therapeutic agents, particularly polysaccharide drugs, including low molecular weight heparin. The invention has utility in the fields of pharmaceutical formulation, pharmacology and medicine.

BACKGROUND

A wide variety of therapeutic agents are conventionally formulated in oil/water emulsion systems. These conventional emulsions take advantage of the increased solubility of many therapeutic agents in oils (triglycerides). Thus, one conventional approach is to solubilize a therapeutic agent in a bioacceptable triglyceride solvent, such as a digestible vegetable oil, and disperse this oil phase in an aqueous medium. The dispersion may be stabilized by emulsifying agents and provided in emulsion form. Alternatively, the therapeutic agent can be provided in a water-free formulation, with an aqueous dispersion being formed in vivo in the gastrointestinal environment. The properties of these oil-based formulations are determined by such factors as the size of the triglyceride/therapeutic agent colloidal particles and the presence or absence of surfactant additives.

In simplest form, a triglyceride-containing formulation suitable for delivering therapeutic agents through an aqueous environment is an oil-in-water emulsion. Such emulsions contain the therapeutic agent solubilized in an oil phase that is dispersed in an aqueous environment with the aid of a surfactant. The surfactant may be present in the oil-based formulation itself, or may be a compound provided in the gastrointestinal system, such as bile salts, which are known to be in vivo emulsifying agents. The colloidal oil particle sizes are relatively large, ranging from several hundred nanometers to several microns in diameter, in a broad particle size distribution. Since the particle sizes are on the order of or greater than the wavelength range of visible light, such emulsions, when prepared in an emulsion dosage form, are visibly "cloudy" or "milky" to the naked eye.

Although conventional triglyceride-based pharmaceutical compositions are useful in solubilizing and delivering some therapeutic agents, such compositions are subject to a number of significant limitations and disadvantages. Emulsions are thermodynamically unstable, and colloidal emulsion particles will spontaneously agglomerate, eventually leading to complete phase separation. The tendency to agglomerate and phase separate presents problems of storage and handling, and increases the likelihood that pharmaceutical emulsions initially properly prepared will be in a less optimal, less effective, and poorly-characterized state upon ultimate administration to a patient. Uncharacterized degradation is particularly disadvantageous, since increased particle size slows the rate of transport of the colloidal particle and digestion of the oil component, and hence the rate and extent of absorption of the therapeutic agent. These problems lead to poorly characterized and potentially harmful changes in the effective dosage received by the patient. Moreover, changes in colloidal emulsion particle size are also believed to render absorption more sensitive to and dependent upon conditions in the gastrointestinal tract, such as pH, enzyme activity, bile components, and stomach contents. Such uncertainty in the rate and extent of ultimate absorption of the therapeutic agent severely compromises the medical professional's ability to safely administer therapeutically effective dosages. In addition, when such compositions are administered parenterally, the presence of large particles can block blood capillaries, further compromising patient safety.

A further disadvantage of conventional triglyceride-containing compositions is the dependence of therapeutic agent absorption on the rate and extent of lipolysis. Although colloidal emulsion particles can transport therapeutic agents through the aqueous environment of the gastrointestinal tract, ultimately the triglyceride must be digested and the therapeutic agent must be released in order to be absorbed through the intestinal mucosa. The triglyceride carrier is emulsified by bile salts and hydrolyzed, primarily by pancreatic lipase. The rate and extent of lipolysis, however, are dependent upon several factors that are difficult to adequately control. For example, the amount and rate of bile salt secretion affect the lipolysis of the triglycerides, and the bile salt secretion can vary with stomach contents, with metabolic abnormalities, and with functional changes of the liver, bile ducts, gall bladder and intestine. Lipase availability in patients with decreased pancreatic secretory function, such as cystic fibrosis or chronic pancreatitis, may be undesirably low, resulting in a slow and incomplete triglyceride lipolysis. The activity of lipase is pH dependent, with deactivation occurring at about pH 3, so that the lipolysis rate will vary with stomach contents, and may be insufficient in patients with gastric acid hyper-secretion. Moreover, certain surfactants commonly used in the preparation of pharmaceutical emulsions, such as polyethoxylated castor oils, may themselves act as inhibitors of lipolysis. Although recent work suggests that certain surfactant combinations, when used in combination with digestible oils in emulsion preparations, can substantially decrease the lipolysis-inhibiting effect of some common pharmaceutical surfactants (see, U.S. Pat. No. 5,645,856), such formulations are still subject to the other disadvantages of pharmaceutical emulsions and triglyceride-based formulations.

Yet another approach is based on formation of "microemulsions." Like an emulsion, a microemulsion is a liquid dispersion of oil in water, stabilized by surfactants. Conventional microemulsions, however, present several safety and efficiency problems. The amount of triglyceride that can be solubilized in a conventional microemulsion is generally quite small, resulting in a poor loading capacity. In order to solubilize significant amounts of triglycerides, large amounts of hydrophilic surfactant and/or solvents must be used. These high concentrations of hydrophilic surfactant and solvents raise questions of safety, since the levels of hydrophilic surfactant and solvent needed can approach or exceed bioacceptable levels.

Thus, conventional triglyceride-containing formulations suffer from limitations and safety concerns including, for example, instability of the formulation, dependence on lipolysis and poor loading capacity of the therapeutic agent. Triglyceride-containing formulations incorporating a therapeutic agent, in particular a polysaccharide drug, that do not suffer from these and other limitations and safety concerns are desired.

Administration of one particular class of therapeutic agents, the polysaccharide drugs, is severely hampered by the permeation barrier imposed by the intestinal epithelial cell membrane as well as the junctional structure between the epithelial cells. In addition, chemical degradation in the acidic environment of the stomach, enzymatic inactivation, and binding or interference by mucous and other contents of the gastrointestinal (GI) tract can also contribute to the reduced availability of polysaccharide drugs in the GI tract for absorption. As a result, the administration of polysaccharide drugs frequently calls for invasive approaches such as subcutaneous or intravenous injection, resulting in severe restrictions in clinical use and problems with patient compliance.

Heparin is a polysaccharide drug of particular interest and importance because it is a potent anticoagulant drug widely used in the prevention and treatment of thrombosis. It decreases the rate of coagulation by increasing the rate at which antithrombin (also termed "heparin cofactor" or "antithrombin III") inhibits activated coagulation factors, particularly thrombin, a key enzyme in the coagulation cascade. Heparin is a glycosaminoglycan present in the secretory granules of mast cells, and is characterized as a polymer of alternating D-glucuronic acid and N-acetyl-D-glucosamine residues (Bourin et al. (1993), "Glycosaminoglycans and the Regulation of Blood Coagulation," *Biochem. J.* 289:313–330). Heparinoids—derivatives, analogs, fragments, salts, esters, etc. of heparin or heparin like glycosaminoglycan such as chrondroitin, dermatan sulfate, sulfomucopolysaccharide, mesoglycan, sulodexide, etc.— are also of paramount interest as anticoagulants.

Among all the heparins and heparinoids, low molecular weight heparin is of particular interest from a clinical standpoint. The potential advantages of low molecular weight heparin over unfractionated heparin include are numerous. For example, it has been suggested that low molecular weight heparin may be associated with a reduced risk of bleeding complications, possibly due to its more specific action on clotting factor Xa and relatively low action on factor IIa. In addition, low molecular weight heparin has a longer half-life so dosing frequency can be reduced. Because low molecular weight heparin exhibits reduced binding to platelets, the incidence of thrombocytopenia is substantially reduced. Furthermore, the likelihood of bone loss is reduced because low molecular weight heparin tends to bind less strongly to osteoblasts. See Hirsch et al. (1998), "Heparin and Low-Molecular-Weight Heparin." *Chest* 114:489S-510S.

Administration of a polysaccharide drug in a triglyceride-containing formulation would overcome some problems such as chemical degradation and enzymatic degradation that are associated with the administration of this class of drug. U.S. Pat. No. 5,626,869 to Nyqvist et al. describes pharmaceutical compositions containing heparin or heparin fragments in a defined lipid system of at least two lipid components. The particles in the described formulations, however, can vary considerably. Such variation in particle sizes results in a milky or cloudy dispersion as some particles in the formulations ostensibly have sizes corresponding to the wavelength of light. In addition, U.S. Pat. No. 5,744,155 to Friedman et al. describes oil-in-water emulsions containing a drug such as a low molecular weight heparin. The described emulsions contain particles having diameters of from 10 nm to 600 nm. Again, the formulations will be milky or cloudy as the particle sizes contained in the described formulations overlap the wavelengths of visible light (400 nm to 700 nm).

Clearly, then, there is a need in the art for a triglyceride-containing formulation for the administration of a polysaccharide drug, such as heparin, heparinoids, and particularly low molecular weight heparin, wherein the formulation contains a therapeutically effective amount of the polysaccharide drug, and the dosage formulation is chemically and physically stable, as evidenced, for example, by a clear dispersion.

SUMMARY OF THE INVENTION

It is therefore an object of the present invention to provide pharmaceutical compositions capable of solubilizing therapeutically effective amounts of therapeutic agents.

It is a further objection of the invention to provide pharmaceutical compositions, wherein the therapeutic agent is a polysaccharide drug.

It is another object of the invention to provide triglyceride-containing pharmaceutical compositions that are homogeneous and thermodynamically stable.

It is still another object of the invention to provide pharmaceutical compositions of a therapeutic agent that have decreased dependence upon lipolysis for bioabsorption.

It is yet another object of the invention to provide pharmaceutical compositions capable of increasing the rate and/or extent of bioabsorption of co-administered therapeutic agents.

It is a further object of the invention to provide pharmaceutical compositions and methods for the prevention of blood coagulation and treatment of thrombosis.

In accordance with these and other objects and features, the present invention provides pharmaceutical compositions for improved solubilization of triglycerides, and improved delivery of therapeutic agents. It has been surprisingly found that pharmaceutical compositions containing significant amounts of triglycerides can be formed without the disadvantages of conventional triglyceride-containing compositions by using a combination of surfactants and triglycerides in amounts such that when the pharmaceutical composition is mixed with an aqueous medium, a clear aqueous dispersion is formed. Such compositions can be co-administered with a therapeutic agent to increase the rate and/or extend of bioabsorption of the therapeutic agent, or can be provided with a therapeutic agent in the preconcentrate composition or in the diluent solution.

In one embodiment, the present invention relates to pharmaceutical compositions having a carrier and a therapeutic agent, e.g., polysaccharide drug, the carrier including a triglyceride and at least two surfactants, at least one of which is hydrophilic. The triglyceride and surfactants are present in amounts such that upon mixing with an aqueous medium in an aqueous medium to carrier ratio of about 100:1 by weight, either in vitro or in vivo, the carrier forms a clear aqueous dispersion. In one aspect of this embodiment, the aqueous dispersion has an absorbance of less than about 0.3 at 400 nm. In another aspect of this embodiment, the aqueous dispersion has an average particle size of less than about 200 nm. In yet another aspect of this embodiment, the carrier is capable of containing more triglyceride than can be solubilized in a clear aqueous dispersion having only one surfactant, the surfactant being hydrophilic.

In another embodiment, the present invention relates to pharmaceutical compositions having a carrier and polysaccharide drug, the carrier including a triglyceride, at least one hydrophilic surfactant, and at least one hydrophobic surfactant. The triglyceride and surfactants are present in amounts such that upon mixing with an aqueous medium in an aqueous medium to carrier ratio of about 100:1 by weight, either in vitro or in vivo, the carrier forms a clear aqueous dispersion. In a particular aspect of this embodiment, the carrier is capable of containing more triglyceride than can be solubilized in a clear aqueous dispersion having a hydrophilic surfactant but not having a hydrophobic surfactant.

In another embodiment, the present invention relates to pharmaceutical compositions having therapeutic agent and a carrier, the carrier including a triglyceride, at least one hydrophilic surfactant, and at least one hydrophobic surfactant. The triglyceride and surfactants are present in amounts such that upon mixing with an aqueous medium in an aqueous medium to carrier ratio of about 100:1 by weight, either in vitro or in vivo, the carrier forms a clear aqueous dispersion. In a particular aspect of this embodiment, the at least one hydrophobic surfactant is present in an amount greater than the amount of the at least one hydrophobic surfactant that remains solubilized in an aqueous dispersion of the carrier having only the at least one hydrophobic surfactant and hydrophilic surfactant without the triglyceride.

In another embodiment, the present invention relates to dosage forms comprising the pharmaceutical compositions described herein. The dosage forms may be processed by techniques selected from the group consisting of lyophilization, encapsulation, extruding, compression, melting, molding, spraying, coating, comminution, mixing, homogenization, sonciation, granulation, and combinations thereof. Dosage forms include, but are not limited, those selected from the group consisting of pills, capsules, caplets, tablets, granules, beads, powders, solutions, suspensions, emulsions, creams, ointments, lotions, suppositories, sprays, aerosols, pastes, gels, drops, douches, ovules, wafers, troches, cachets, syrups and elixirs.

In another embodiment, the invention relates to methods of treating an animal, e.g., a mammalian patient such as a human patient, with a therapeutic agent, e.g., a polysaccharide drug, the method involving providing a dosage form of a pharmaceutical composition having a carrier as described herein, providing the polysaccharide drug, and administering the dosage form to the animal. In one particular aspect of this embodiment, the polysaccharide drug is administered simultaneously, e.g., either as a part of the composition or as part of a separate and distinct composition. In another aspect of this embodiment, the polysaccharide drug is administered sequentially, e.g., either the polysaccharide drug is administered first followed by administration of the composition, or the composition is first followed by administration of the polysaccharide drug.

In another embodiment, the invention relates to the administration of a combination of therapeutic agents, e.g., a low molecular weight (LMW) heparin in combination with an anticoagulant, platelet inhibitor, and/or fibrinolytic agent, in a single dosage form or in separate dosage forms. Such combinations provide several benefits to patients as will be discussed below. Preferred combinations include: LMW heparin with one or more anticoagulants, e.g., warfarin sodium, dipyridamole, or a combination thereof; LMW heparin with one or more platelet inhibitors, e.g., aspirin, hirudin, cilostazol, ticlidopine, clopidrogel, abciximab, eptifitabide, bivalirudin, or combination thereof; and LMW heparin with a fibrinolytic agent, e.g., unfractionated heparin, r-tPA, or combinations thereof.

In another embodiment, the present invention relates to methods of increasing the amount of hydrophobic surfactant that can be solubilized in a clear aqueous dispersion, by providing a composition including carrier having a triglyceride, at least one hydrophilic surfactant, and one hydrophobic surfactant, and dispersing the composition in an aqueous medium so that a clear aqueous dispersion is formed. Within the clear aqueous dispersion, the hydrophobic surfactant is present in an amount greater than the amount of the hydrophobic surfactant that remains solubilized in an aqueous dispersion of the carrier having only the at least one hydrophobic surfactant and hydrophilic surfactant without the triglyceride.

In another embodiment, the present invention relates to methods of treating an animal, e.g., a mammalian patient, with a therapeutic drug, the method comprising providing an initial dosage form of a pharmaceutical composition having a therapeutic agent and a carrier comprising a triglyceride, at least one hydrophilic surfactant, and at least one hydrophobic surfactant, and administering the dosage form to the animal. The triglyceride and surfactants are present in amounts such that upon mixing with an aqueous medium in an aqueous medium to carrier ratio of about 100:1 by weight, either in vitro or in vivo, the carrier forms a clear aqueous dispersion. The at least one hydrophobic surfactant is present in an amount greater than the amount of the at least one hydrophobic surfactant that remains solubilized in an aqueous dispersion of the carrier having only the at least one hydrophobic surfactant and hydrophilic surfactant without the triglyceride. The primary therapeutic agent may be present in the initial dosage form or may be present in a second dosage form. Similarly, additional therapeutic agents may be present in the initial dosage form or may be present in a second dosage form, independent of the dosage form containing the primary therapeutic agent.

In another embodiment, the present invention relates to a pharmaceutical composition comprising an oil soluble vitamin and a carrier comprising a triglyceride, at least one hydrophilic surfactant, and at least one hydrophobic surfactant. The triglyceride and surfactants are present in amounts such that upon mixing with an aqueous medium in an aqueous medium to carrier ratio of about 100:1 by weight, either in vitro or in vivo, the carrier forms a clear aqueous dispersion.

In another embodiment, the present invention relates to a method for increasing the loading capacity of a pharmaceutical composition comprising the steps of: providing a pharmaceutical composition comprised of (a) a carrier comprising a triglyceride and a first surfactant, and (b) a therapeutically effective amount of a polysaccharide drug; and adding an absorption-enhancing amount of a second surfactant to the pharmaceutical composition, the second surfactant comprising a hydrophilic surfactant, wherein the absorption enhancing amount is effective to increase the loading capacity of the capacity of the pharmaceutical composition.

These and other objects and features of the present invention will become more fully apparent from the following description and appended claims, or may be learned by the practice of the invention as set forth hereinafter.

DETAILED DESCRIPTION

The present invention overcomes the problems described above characteristic of conventional triglyceride-containing formulations by providing unique pharmaceutical compositions that form clear aqueous dispersions upon mixing with an aqueous medium. Surprisingly, the present inventors have found that compositions including triglycerides and a combination of surfactants can solubilize therapeutically effective amounts of therapeutic agents. In addition, when they are mixed with an aqueous medium, the compositions are surprisingly able to form homogeneous, single-phase aqueous dispersions that are thermodynamically stable and optically clear. The optical clarity is indicative of a very small particle size within the aqueous dispersions, and this small particle size substantially reduces lipolysis dependence of the rate of bioabsorption, and other disadvantages of conventional triglyceride-containing formulations. Use of these formulations is thus believed to result in an enhanced extent, rate and/or consistency of absorption of the therapeutic agent. Advantageously, the compositions of the present invention are surprisingly able to increase solubilize greater amounts of triglycerides, than conventional formulations, even when the total surfactant concentration is the same as in a conventional formulation. In addition, the compositions of the present invention are surprisingly able to increase the solubilization power of surfactants as well.

A. Pharmaceutical Compositions

In one embodiment, the present invention provides a pharmaceutical composition including carrier. The carrier includes a triglyceride and at least two surfactants, at least one of which is a hydrophilic surfactant. Optionally, the carrier includes a triglyceride, at least one hydrophilic surfactant, and at least one hydrophobic surfactant. The triglyceride and surfactants are present in amounts such that upon dilution with an aqueous medium, either in vitro or in vivo, the composition forms a clear aqueous dispersion. It is a particular and surprising feature of the present invention that the composition is homogeneous and optically clear, despite the presence of substantial amounts of triglycerides, thereby providing surprising and important advantages over conventional triglyceride-containing formulations.

1. Triglycerides

The compositions of the present invention include one or more pharmaceutically acceptable triglycerides. Examples of triglycerides suitable for use in the present invention are shown in Table 1. In general, these triglycerides are readily available from commercial sources. For several triglycerides, representative commercial products and/or commercial suppliers are listed.

TABLE 1

| Triglycerides | |
|---|---|
| Triglyceride | Commercial Source |
| Aceituno oil | |
| Almond oil | Super Refined Almond Oil (Croda) |
| Araehis oil | |
| Babassu oil | |
| Blackcurrant seed oil | |
| Borage oil | |
| Buffalo ground oil | |
| Candlenut oil | |

TABLE 1-continued

| Triglycerides | |
|---|---|
| Triglyceride | Commercial Source |
| Canola oil | Lipex 108 (Abitec) |
| Castor oil | |
| Chinese vegetable tallow oil | |
| Cocoa butter | |
| Coconut oil | Pureco 76 (Abitec) |
| Coffee seed oil | |
| Corn oil | Super Refined Corn Oil (Croda) |
| Cottonseed oil | Super Refined Cottonseed Oil (Croda) |
| Crambe oil | |
| *Cuphea* species oil | |
| Evening primrose oil | |
| Grapeseed oil | |
| Groundnut oil | |
| Hemp seed oil | |
| Illipe butter | |
| Kapok seed oil | |
| Linseed oil | |
| Menhaden oil | Super Refined Menhaden Oil (Croda) |
| Mowrah butter | |
| Mustard seed oil | |
| Oiticica oil | |
| Olive oil | Super Refined Olive Oil (Croda) |
| Palm oil | |
| Palm kernel oil | |
| Peanut oil | Super Refined Peanut Oil (Croda) |
| Poppy seed oil | |
| Rapeseed oil | |
| Rice bran oil | |
| Safflower oil | Super Refined Safflower Oil (Croda) |
| Sal fat | |
| Sesame oil | Super Refined Sesame Oil (Croda) |
| Shark liver oil | Super Refined Shark Liver Oil (Croda) |
| Shea nut oil | |
| Soybean oil | Super Refined Soybean Oil (Croda) |
| Stillingia oil | |
| Sunflower oil | |
| Tall oil | |
| Tea seed oil | |
| Tobacco seed oil | |
| Tung oil (China wood oil) | |
| Ucuhuba | |
| Vernonia oil | |
| Wheat germ oil | Super Refined Wheat Germ Oil (Croda) |
| Hydrogenated castor oil | Castorwax |
| Hydrogenated coconut oil | Pureco 100 (Abitec) |
| Hydrogenated cottonseed oil | Dritex C (Abitec) |
| Hydrogenated palm oil | Dritex PST (Abitec); Softisan 154 (Hüls) |
| Hydrogenated soybean oil | Sterotex HM NF (Abitec); Dritex S (Abitec) |
| Hydrogenated vegetable oil | Sterotex NF (Abitec); Hydrokote M (Abitec) |
| Hydrogenated cottonseed and castor oil | Sterotex K (Abitec) |
| Partially hydrogenated soybean oil | Hydrokote AP5 (Abitec) |
| Partially soy and cottonseed oil | Apex B (Abitec) |
| Glyceryl tributyrate | (Sigma) |
| Glyceryl tricaproate | (Sigma) |
| Glyceryl tricaprylate | (Sigma) |
| Glyceryl tricaprate | Captex 1000 (Abitec) |
| Glyceryl tri-undecanoate | Captex 8227 (Abitec) |
| Glyceryl trilaurate | (Sigma) |
| Glyceryl trimyristate | Dynasan 114 (Hüls) |
| Glyceryl tripalmitate | Dynasan 116 (Hüls) |

TABLE 1-continued

Triglycerides

| Triglyceride | Commercial Source |
|---|---|
| Glyceryl tristearate | Dynasan 118 (Hüls) |
| Glyceryl triarchidate | (Sigma) |
| Glyceryl tri-myristoleate | (Sigma) |
| Glyceryl tri-palmitoleate | (Sigma) |
| Glyceryl trioleate | (Sigma) |
| Glyceryl trilinoleate | (Sigma) |
| Glyceryl tri-linolenate | (Sigma) |
| Glyceryl tricaprylate/caprate | Captex 300 (Abitec); Captex 355 (Abitec); Miglyol 810 (Hüls); Miglyol 812 (Hüls) |
| Glyceryl tricaprylate/caprate/laurate | Captex 350 (Abitec) |
| Glyceryl tricaprylate/caprate/linoleate | Captex 810 (Abitec); Miglyol 818 (Hüls) |
| Glyceryl tricaprylate/caprate/stearate | Softisan 378 (Hüls); (Larodan) |
| Glyceryl tricaprylate/laurate/stearate | (Larodan) |
| Glyceryl 1,2-caprylate-3-linoleate | (Larodan) |
| Glyceryl 1,2-caprate-3-stearate | (Larodan) |
| Glyceryl 1,2-laurate-3-myristate | (Larodan) |
| Glyceryl 1,2-myristate-3-laurate | (Larodan) |
| Glyceryl 1,3-palmitate-2-butyrate | (Larodan) |
| Glyceryl 1,3-stearate-2-caprate | (Larodan) |
| Glyceryl 1,2-linoleate-3-caprylate | (Larodan) |

Fractionated triglycerides, modified triglycerides, synthetic triglycerides, and mixtures of triglycerides are also within the scope of the invention.

Preferred triglycerides include vegetable oils, fish oils, animal fats, hydrogenated vegetable oils, partially hydrogenated vegetable oils, medium and long-chain triglycerides, and structured triglycerides. It should be appreciated that several commercial surfactant compositions contain small to moderate amounts of triglycerides, typically as a result of incomplete reaction of a triglyceride starting material in, for example, a transesterification reaction. Such commercial surfactant compositions, while nominally referred to as "surfactants," may be suitable to provide all or part of the triglyceride component for the compositions of the present invention. Examples of commercial surfactant compositions containing triglycerides include some members of the surfactant families Gelucires (Gattefosse), Maisines (Gattefosse), and Imwitors (Hüls). Specific examples of these compositions are:

Gelucire 44/14 (saturated polyglycolized glycerides);
Gelucire 50/13 (saturated polyglycolized glycerides);
Gelucire 53/10 (saturated polyglycolized glycerides);
Gelucire 33/01 (semi-synthetic triglycerides of $C_8$–$C_{18}$ saturated fatty acids);
Gelucire 39/01 (semi-synthetic glycerides);
other Gelucires, such as 37/06, 43/01, 35/10, 37/02, 46/07, 48/09, 50/02, 62/05, etc.;
Maisine 35-I (linoleic glycerides); and
Imwitor 742 (caprylic/capric glycerides);

Still other commercial surfactant compositions having significant triglyceride content are known to those skilled in the art. It should be appreciated that such compositions, which contain triglycerides as well as surfactants, may be suitable to provide all or part of the triglyceride component of the compositions of the present invention, as well as all or part of the surfactant component, as described below. Of course, none of the commonly known triglyceride-containing commercial surfactants alone provides the unique pharmaceutical compositions and characteristics as recited in the appended claims.

Among the above-listed triglycerides, preferred triglycerides include: almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; soy oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; and glyceryl tricaprylate/caprate/stearate. Other preferred triglycerides are saturated polyglycolized glycerides (Gelucire 44/14, Gelucire 50/13 and Gelucire 53/10), linoleic glycerides (Maisine 35-I), and caprylic/capric glycerides (Imwitor 742).

Among the preferred triglycerides, particularly preferred triglycerides include: coconut oil; corn oil; olive oil; palm oil; peanut oil; safflower oil; sesame oil; soybean oil; hydrogenated castor oil; hydrogenated coconut oil; partially hydrogenated soybean oil; glyceryl tricaprate; glyceryl trilaurate; glyceryl trioleate; glyceryl trilinoleate; glyceryl tricaprylate/caprate; glyceryl tricaprylate/caprate/laurate; glyceryl tricaprylate/caprate/linoleate; glyceryl tricaprylate/caprate/stearate; saturated polyglycolized glycerides (Gelucire 44/14, Gelucire 50/13 and Gelucire 53/10); linoleic glycerides (Maisine 35-I); and caprylic/capric glycerides (Imwitor 742).

2. Surfactants

The carrier includes a combination of surfactants, at least one of which is a hydrophilic surfactant, with the remaining surfactant or surfactants being hydrophilic or hydrophobic. As is well known in the art, the terms "hydrophilic" and "hydrophobic" are relative terms. To function as a surfactant, a compound must necessarily include polar or charged hydrophilic moieties as well as non-polar hydrophobic (lipophilic) moieties; i.e., a surfactant compound must be amphiphilic. An empirical parameter commonly used to characterize the relative hydrophilicity and hydrophobicity of non-ionic amphiphilic compounds is the hydrophilic-lipophilic balance (the "HLB" value). Surfactants with lower HLB values are more hydrophobic, and have greater solubility in oils, whereas surfactants with higher HLB values are more hydrophilic, and have greater solubility in aqueous mediums.

Using HLB values as a rough guide, hydrophilic surfactants are generally considered to be those compounds having an HLB value greater than about 10, as well as anionic, cationic, or zwitterionic compounds for which the HLB scale is not generally applicable. Similarly, hydrophobic surfactants are compounds having an HLB value less than about 10.

It should be appreciated that the HLB value of a surfactant is merely a rough guide generally used to enable formulation of industrial, pharmaceutical and cosmetic emulsions. For many important surfactants, including several polyethoxylated surfactants, it has been reported that HLB values can differ by as much as about 8 HLB units, depending upon the empirical method chosen to determine the HLB value (Schott, *J. Pharm. Sciences,* 79(1), 87–88 (1990)). Likewise, for certain polypropylene oxide containing block copolymers (poloxamers, available commercially as PLURONIC® surfactants, BASF Corp.), the HLB values may not accurately reflect the true physical chemical nature of the compounds. Finally, commercial surfactant products are generally not pure compounds, but are often complex mixtures of compounds, and the HLB value reported for a particular compound may more accurately be characteristic of the commercial product of which the compound is a major component. Different commercial products having the same primary surfactant component can, and typically do, have different HLB values. In addition, a certain amount of lot-to-lot variability is expected even for a single commercial surfactant product. Keeping these inherent difficulties in mind, and using HLB values as a guide, one skilled in the art can readily identify surfactants having suitable hydrophilicity or hydrophobicity for use in the present invention, as described herein.

The carrier of the present invention includes at least one hydrophilic surfactant. The hydrophilic surfactant can be any surfactant suitable for use in pharmaceutical compositions. Suitable hydrophilic surfactants can be anionic, cationic, zwitterionic or non-ionic, although non-ionic hydrophilic surfactants are presently preferred. Preferably, the carrier includes a mixture of two or more hydrophilic surfactants, more preferably two or more non-ionic hydrophilic surfactants. Also preferred are mixtures of at least one hydrophilic surfactant, preferably non-ionic, and at least one hydrophobic surfactant.

The choice of specific surfactants should be made keeping in mind the particular triglycerides and optional therapeutic agents to be used in the composition, and the range of polarity appropriate for the chosen therapeutic agent. With these general principles in mind, a very broad range of surfactants is suitable for use in the present invention. Such surfactants can be grouped into the following general chemical classes detailed in the Tables herein. The HLB values given in the Tables below generally represent the HLB value as reported by the manufacturer of the corresponding commercial product. In cases where more than one commercial product is listed, the HLB value in the Tables is the value as reported for one of the commercial products, a rough average of the reported values, or a value that, in the judgment of the present inventors, is more reliable. It should be emphasized that the invention is not limited to the surfactants in the Tables, which show representative, but not exclusive, lists of available surfactants.

2.1. Polyethoxylated Fatty Acids

Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid are especially useful. Among the surfactants of Table 2, preferred hydrophilic surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. Examples of polyethoxylated fatty acid monoester surfactants commercially available are shown in Table 2.

TABLE 2

PEG-Fatty Acid Monoester Surfactants

| COMPOUND | COMMERCIAL PRODUCT (Supplier) | HLB |
|---|---|---|
| PEG 4-100 monolaurate | Crodet L series (Croda) | >9 |
| PEG 4-100 monooleate | Crodet O series (Croda) | >8 |
| PEG 4-100 monostearate | Crodet S series (Croda), Myrj Series (Atlas/ICI) | >6 |
| PEG 400 distearate | Cithrol 4DS series (Croda) | >10 |
| PEG 100,200,300 monolaurate | Cithrol ML series (Croda) | >10 |
| PEG 100,200,300 monooleate | Cithrol MO series (Croda) | >10 |
| PEG 400 dioleate | Cithrol 4DO series (Croda) | >10 |
| PEG 400-1000 monostearate | Cithrol MS series (Croda) | >10 |
| PEG-1 stearate | Nikkol MYS-1EX (Nikko), Coster K1 (Condea) | 2 |
| PEG-2 stearate | Nikkol MYS-2 (Nikko) | 4 |
| PEG-2 oleate | Nikkol MYO-2 (Nikko) | 4.5 |
| PEG-4 laurate | Mapeg ® 200 ML (PPG), Kessco ® PEG 200ML (Stepan), LIPOPEG 2L (LIPO Chem.) | 9.3 |
| PEG-4 oleate | Mapeg ® 200 MO (PPG), Kessco ® PEG 200 MO (Stepan), | 8.3 |
| PEG-4 stearate | Kessco ® PEG 200 MS (Stephan), Hodag 20 S (Calgene), Nikkol MYS-4 (Nikko) | 6.5 |
| PEG-5 stearate | Nikkol TMGS-5 (Nikko) | 9.5 |
| PEG-5 oleate | Nikkol TMGO-5 (Nikko) | 9.5 |
| PEG-6 oleate | Algon OL 60 (Auschem SpA), Kessco ® PEG 300 MO (Stephan), Nikkol MYO-6 (Nikko), Emulgante A6 (Condea) | 8.5 |
| PEG-7 oleate | Algon OL 70 (Auschem SpA) | 10.4 |
| PEG-6 laurate | Kessco ® PEG300 ML (Stepan) | 11.4 |
| PEG-7 laurate | Lauridac 7 (Condea) | 13 |
| PEG-6 stearate | Kessco ® PEG300 MS (Stepan) | 9.7 |
| PEG-8 laurate | Mapeg ® 400 ML (PPG), LIPOPEG 4DL (Lipo Chem.) | 13 |
| PEG-8 oleate | Mapeg ® 400 MO (PPG), Emulgante A8 (Condea); Kessco PEG 400 MO (Stepan) | 12 |
| PEG-8 stearate | Mapeg ® 400 MS (PPG), Myrj 45 | 12 |
| PEG-9 oleate | Emulgante A9 (Condea) | >10 |
| PEG-9 stearate | Cremophor S9 (BASF) | >10 |
| PEG-10 laurate | Nikkol MYL-10 (Nikko), Lauridac 10 (Croda) | 13 |
| PEG-10 oleate | Nikkol MYO-10 (Nikko) | 11 |
| PEG-10 stearate | Nikkol MYS-10 (Nikko), Coster K100 (Condea) | 11 |
| PEG-12 laurate | Kessco ® PEG 600ML (Stepan) | 15 |
| PEG-12 oleate | Kessco ® PEG 600MO (Stepan) | 14 |
| PEG-12 ricinoleate | (CAS #9004-97-1) | >10 |
| PEG-12 stearate | Mapeg ® 600 MS (PPG), Kessco ® PEG 600MS (Stepan) | 14 |
| PEG-15 stearate | Nikkol TMGS-15 (Nikko), Koster K15 (Condea) | 14 |
| PEG-15 oleate | Nikkol TMGO-15 (Nikko) | 15 |
| PEG-20 laurate | Kessco ® PEG 1000 ML (Stepan) | 17 |
| PEG-20 oleate | Kessco ® PEG 1000 MO (Stepan) | 15 |
| PEG-20 stearate | Mapeg ® 1000 MS (PPG), Kessco ® PEG 1000 MS (Stepan), Myrj 49 | 16 |
| PEG-25 stearate | Nikkol MYS-25 (Nikko) | 15 |
| PEG-32 laurate | Kessco ® PEG 1540 ML (Stepan) | 16 |
| PEG-32 oleate | Kessco ® PEG 1540 MO (Stepan) | 17 |
| PEG-32 stearate | Kessco ® PEG 1540 MS (Stepan) | 17 |
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-40 stearate | Myrj 52, Emerest ® 2715 (Henkel), Nikkol MYS-40 (Nikko) | >10 |
| PEG-45 stearate | Nikkol MYS-45 (Nikko) | 18 |

TABLE 2-continued

PEG-Fatty Acid Monoester Surfactants

| COMPOUND | COMMERCIAL PRODUCT (Supplier) | HLB |
|---|---|---|
| PEG-50 stearate | Myrj 53 | >10 |
| PEG-55 stearate | Nikkol MYS-55 (Nikko) | 18 |
| PEG-100 oleate | Crodet O-100 (Croda) | 18.8 |
| PEG-100 stearate | Myrj 59, Arlacel 165 (ICI) | 19 |
| PEG-200 oleate | Albunol 200 MO (Taiwan Surf.) | >10 |
| PEG-400 oleate | LACTOMUL (Henkel), Albunol 400 MO (Taiwan Surf.) | >10 |
| PEG-600 oleate | Albunol 600 MO (Taiwan Surf.) | >10 |

2.2 PEG-Fatty Acid Diesters

Polyethylene glycol (PEG) fatty acid diesters are also suitable for use as surfactants in the compositions of the present invention. Among the surfactants in Table 3, preferred hydrophilic surfactants include PEG-20 dilaurate, PEG-20 dioleate, PEG-20 distearate, PEG-32 dilaurate and PEG-32 dioleate. Representative PEG-fatty acid diesters are shown in Table 3.

TABLE 3

PEG-Fatty Acid Diester Surfactants

| COMPOUND | COMMERCIAL PRODUCT (Supplier) | HLB |
|---|---|---|
| PEG-4 dilaurate | Mapeg ® 200 DL (PPG), Kessco ® PEG 200 DL (Stepan), LIPOPEG 2-DL (Lipo Chem.) | 7 |
| PEG-4 dioleate | Mapeg ® 200 DO (PPG), | 6 |
| PEG-4 distearate | Kessco ® 200 DS (Stepan) | 5 |
| PEG-6 dilaurate | Kessco ® PEG 300 DL (Stepan) | 9.8 |
| PEG-6 dioleate | Kessco ® PEG 300 DO (Stepan) | 7.2 |
| PEG-6 distearate | Kessco ® PEG 300 DS (Stepan) | 6.5 |
| PEG-8 dilaurate | Mapeg ® 400 DL (PPG), Kessco ® PEG 400 DL (Stepan), LIPOPEG 4 DL (Lipo Chem.) | 11 |
| PEG-8 dioleate | Mapeg ® 400 DO (PPG), Kessco ® PEG 400 DO (Stepan), LIPOPEG 4 DO (Lipo Chem.) | 8.8 |
| PEG-8 distearate | Mapeg ® 400 DS (PPG), CDS 400 (Nikkol) | 11 |
| PEG-10 dipalmitate | Polyaldo 2PKFG | >10 |
| PEG-12 dilaurate | Kessco ® PEG 600 DL (Stepan) | 11.7 |
| PEG-12 distearate | Kessco ® PEG 600 DS (Stepan) | 10.7 |
| PEG-12 dioleate | Mapeg ® 600 DO (PPG), Kessco ® 600 DO (Stepan) | 10 |
| PEG-20 dilaurate | Kessco ® PEG 1000 DL (Stepan) | 15 |
| PEG-20 dioleate | Kessco ® PEG 1000 DO (Stepan) | 13 |
| PEG-20 distearate | Kessco ® PEG 1000 DS (Stepan) | 12 |
| PEG-32 dilaurate | Kessco ® PEG 1540 DL (Stepan) | 16 |
| PEG-32 dioleate | Kessco ® PEG 1540 DO (Stepan) | 15 |
| PEG-32 distearate | Kessco ® PEG 1540 DS (Stepan) | 15 |
| PEG-400 dioleate | Cithrol 4DO series (Croda) | >10 |
| PEG-400 distearate | Cithrol 4DS series (Croda) | >10 |

2.3 PEG-Fatty Acid Mono- and Di-ester Mixtures

In general, mixtures of surfactants are also useful in the present invention, including mixtures of two or more commercial surfactant products. Several PEG-fatty acid esters are marketed commercially as mixtures or mono- and diesters. Representative surfactant mixtures are shown in Table 4.

TABLE 4

PEG-Fatty Acid Mono- and Diester Mixtures

| COMPOUND | COMMERCIAL PRODUCT (Supplier) | HLB |
|---|---|---|
| PEG 4-150 mono, dilaurate | Kessco ® PEG 200-6000 mono, dilaurate (Stepan) | |
| PEG 4-150 mono, dioleate | Kessco ® PEG 200-6000 mono, dioleate (Stepan) | |
| PEG 4-150 mono, distearate | Kessco ® 200-6000 mono, distearate (Stepan) | |

2.4 Polyethylene Glycol Glycerol Fatty Acid Esters

Suitable PEG glycerol fatty acid esters are shown in Table 5. Among the surfactants in the Table, preferred hydrophilic surfactants are PEG-20 glyceryl laurate, PEG-30 glyceryl laurate, PEG-40 glyceryl laurate, PEG-20 glyceryl oleate, and PEG-30 glyceryl oleate.

TABLE 5

PEG Glycerol Fatty Acid Esters

| COMPOUND | COMMERCIAL PRODUCT (Supplier) | HLB |
|---|---|---|
| PEG-20 glyceryl laurate | Tagat ® L (Goldschmidt) | 16 |
| PEG-30 glyceryl laurate | Tagat ® L2 (Goldschmidt) | 16 |
| PEG-15 glyceryl laurate | Glycerox L series (Croda) | 15 |
| PEG-40 glyceryl laurate | Glycerox L series (Croda) | 15 |
| PEG-20 glyceryl stearate | Capmul ® EMG (ABITEC), Aldo ® MS-20 KFG (Lonza) | 13 |
| PEG-20 glyceryl oleate | Tagat ® O (Goldschmidt) | >10 |
| PEG-30 glyceryl oleate | Tagat ® O2 (Goldschmidt) | >10 |

2.5. Alcohol—Oil Transesterification Products

A large number of surfactants of different degrees of hydrophobicity or hydrophilicity can be prepared by reaction of alcohols or polyalcohols with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Preferred alcohols include glycerol, propylene glycol, ethylene glycol, polyethylene glycol, sorbitol, and pentaerythritol. Among these alcohol-oil transesterified surfactants, preferred hydrophilic surfactants are PEG-35 castor oil (Incrocas-35), PEG-40 hydrogenated castor oil (Cremophor RH 40), PEG-25 trioleate (TAGAT® TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). Preferred hydrophobic surfactants in this class include PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil(® M 1969 CS), PEG-6 hydrogenated palm kernel oil (Labrafil® M 2130 BS), PEG-6 palm kernel oil (Labrafil® M 2130 CS), PEG-6 triolein (Labrafil® M 2735 CS), PEG-8 corn oil (Labrafil® WL 2609 BS), PEG-20 corn glycerides (Crovol M40), and PEG-20 almond glycerides (Crovol A40). The latter two surfactants are reported to have HLB values of 10, which is generally considered to be the approximate borderline between hydrophilic and hydrophobic surfactants. For purposes of the present invention, these two surfactants are considered to be hydrophobic. Representative surfactants of this class suitable for use in the present invention are shown in Table 6.

TABLE 6

Transesterification Products of Oils and Alcohols

| COMPOUND | COMMERCIAL PRODUCT (Supplier) | HLB |
|---|---|---|
| PEG-3 castor oil | Nikkol CO-3 (Nikko) | 3 |
| PEG-5, 9, and 16 castor oil | ACCONON CA series (ABITEC) | 6–7 |
| PEG-20 castor oil | Emalex C-20 (Nihon Emulsion), Nikkol CO-20 TX (Nikko) | 11 |
| PEG-23 castor oil | Emulgante EL23 | >10 |
| PEG-30 castor oil | Emalex C-30 (Nihon Emulsion), Alkamuls ® EL 620 (Rhone-Poulenc), Incrocas 30 (Croda) | 11 |
| PEG-35 castor oil | Cremophor EL and EL-P (BASF), Emulphor EL, Incrocas-35 (Croda), Emulgin RO 35 (Henkel) | |
| PEG-38 castor oil | Emulgante EL 65 (Condea) | |
| PEG-40 castor oil | Emalex C-40 (Nihon Emulsion), Alkamuls ® EL 719 (Rhone-Poulenc) | 13 |
| PEG-50 castor oil | Emalex C-50 (Nihon Emulsion) | 14 |
| PEG-56 castor oil | Eumulgin ® PRT 56 (Pulcra SA) | >10 |
| PEG-60 castor oil | Nikkol CO-60TX (Nikko) | 14 |
| PEG-100 castor oil | Thornley | >10 |
| PEG-200 castor oil | Eumulgin ® PRT 200 (Pulcra SA) | >10 |
| PEG-5 hydrogenated castor oil | Nikkol HCO-5 (Nikko) | 6 |
| PEG-7 hydrogenated castor oil | Simusol ® 989 (Seppic), Cremophor WO7 (BASF) | 6 |
| PEG-10 hydrogenated castor oil | Nikkol HCO-10 (Nikko) | 6.5 |
| PEG-20 hydrogenated castor oil | Nikkol HCO-20 (Nikko) | 11 |
| PEG-25 hydrogenated castor oil | Simusol ® 1292 (Seppic), Cerex ELS 250 (Auschem SpA) | 11 |
| PEG-30 hydrogenated castor oil | Nikkol HCO-30 (Nikko) | 11 |
| PEG-40 hydrogenated castor oil | Cremophor RH 40 (BASF), Croduret (Croda), Emulgin HRE 40 (Henkel) | 13 |
| PEG-45 hydrogenated castor oil | Cerex ELS 450 (Auschem Spa) | 14 |
| PEG-50 hydrogenated castor oil | Emalex HC-50 (Nihon Emulsion) | 14 |
| PEG-60 hydrogenated castor oil | Nikkol HCO-60 (Nikko); Cremophor RH 60 (BASF) | 15 |
| PEG-80 hydrogenated castor oil | Nikkol HCO-80 (Nikko) | 15 |
| PEG-100 hydrogenated castor oil | Nikkol HCO-100 (Nikko) | 17 |
| PEG-6 corn oil | Labrafil ® M 2125 CS (Gattefosse) | 4 |
| PEG-6 almond oil | Labrafil ® M 1966 CS (Gattefosse) | 4 |
| PEG-6 apricot kernel oil | Labrafil ® M 1944 CS (Gattefosse) | 4 |
| PEG-6 olive oil | Labrafil ® M 1980 CS (Gattefosse) | 4 |
| PEG-6 peanut oil | Labrafil ® M 1969 CS (Gattefosse) | 4 |
| PEG-6 hydrogenated palm kernel oil | Labrafil ® M 2130 BS (Gattefosse) | 4 |
| PEG-6 palm kernel oil | Labrafil ® M 2130 CS (Gattefosse) | 4 |
| PEG-6 triolein | Labrafil ® M 2735 CS (Gattefosse) | 4 |
| PEG-8 corn oil | Labrafil ® WL 2609 BS (Gattefosse) | 6–7 |
| PEG-20 corn glycerides | Crovol M40 (Croda) | 10 |
| PEG-20 almond glycerides | Crovol A40 (Croda) | 10 |
| PEG-25 trioleate | TAGAT ® TO (Goldschmidt) | 11 |
| PEG-40 palm kernel oil | Crovol PK-70 | >10 |
| PEG-60 corn glycerides | Crovol M70 (Croda) | 15 |
| PEG-60 almond glycerides | Crovol A70 (Croda) | 15 |

TABLE 6-continued

Transesterification Products of Oils and Alcohols

| COMPOUND | COMMERCIAL PRODUCT (Supplier) | HLB |
|---|---|---|
| PEG-4 caprylic/capric triglyceride | Labrafac ® Hydro (Gattefosse), | 4–5 |
| PEG-8 caprylic/capric glycerides | Labrasol (Gattefosse), Labrafac CM 10 (Gattefosse) | >10 |
| PEG-6 caprylic/capric glycerides | SOFTIGEN ® 767 (Hüls), Glycerox 767 (Croda) | 19 |
| Lauroyl macrogol-32 glyceride | GELUCIRE 44/14 (Gattefosse) | 14 |
| Stearoyl macrogol glyceride | GELUCIRE 50/13 (Gattefosse) | 13 |
| Mono, di, tri, tetra esters of vegetable oils and sorbitol | SorbitoGlyceride (Gattefosse) | <10 |
| Pentaerythrityl tetraisostearate | Crodamol PTIS (Croda) | <10 |
| Pentaerythrityl distearate | Albunol DS (Taiwan Surf.) | <10 |
| Pentaerythrityl tetraoleate | Liponate PO-4 (Lipo Chem.) | <10 |
| Pentaerythrityl tetrastearate | Liponate PS-4 (Lipo Chem.) | <10 |
| Pentaerythrityl tetracaprylate/tetracaprate | Liponate PE-810 (Lipo Chem.), Crodamol PTC (Croda) | <10 |
| Pentaerythrityl tetraoctanoate | Nikkol Pentarate 408 (Nikko) | |

Also included as oils in this category of surfactants are oil-soluble vitamins, such as vitamins A, D, E, K, etc. Thus, derivatives of these vitamins, such as tocopheryl PEG-1000 succinate (TPGS, available from Eastman), are also suitable surfactants.

2.6. Polyglycerized Fatty Acids

Polyglycerol esters of fatty acids are also suitable surfactants for the present invention. Among the polyglyceryl fatty acid esters, preferred hydrophobic surfactants include polyglyceryl oleate (Plurol Oleique), polyglyceryl-2 dioleate (Nikkol DGDO), and polyglyceryl-10 trioleate. Preferred hydrophilic surfactants include polyglyceryl-10 laurate (Nikkol Decaglyn 1-L), polyglyceryl-10 oleate (Nikkol Decaglyn 1-O), and polyglyceryl-10 mono, dioleate (Caprol® PEG 860). Polyglyceryl polyricinoleates (Polymuls) are also preferred hydrophilic and hydrophobic surfactants. Examples of suitable polyglyceryl esters are shown in Table 7.

TABLE 7

Polyglycerized Fatty Acids

| COMPOUND | COMMERCIAL PRODUCT (Supplier) | HLB |
|---|---|---|
| Polyglyceryl-2 stearate | Nikkol DGMS (Nikko) | 5–7 |
| Polyglyceryl-2 oleate | Nikkol DGMO (Nikko) | 5–7 |
| Polyglyceryl-2 isostearate | Nikkol DGMIS (Nikko) | 5–7 |
| Polyglyceryl-3 oleate | Caprol ® 3GO (ABITEC), Drewpol 3-1-O (Stepan) | 6.5 |
| Polyglyceryl-4 oleate | Nikkol Tetraglyn 1-O (Nikko) | 5–7 |
| Polyglyceryl-4 stearate | Nikkol Tetraglyn 1-S (Nikko) | 5–6 |

TABLE 7-continued

Polyglycerized Fatty Acids

| COMPOUND | COMMERCIAL PRODUCT (Supplier) | HLB |
|---|---|---|
| Polyglyceryl-6 oleate | Drewpol 6-1-O (Stepan), Nikkol Hexaglyn 1-O (Nikko) | 9 |
| Polyglyceryl-10 laurate | Nikkol Decaglyn 1-L (Nikko) | 15 |
| Polyglyceryl-10 oleate | Nikkol Decaglyn 1-O (Nikko) | 14 |
| Polyglyceryl-10 stearate | Nikkol Decaglyn 1-S (Nikko) | 12 |
| Polyglyceryl-6 ricinoleate | Nikkol Hexaglyn PR-15 (Nikko) | >8 |
| Polyglyceryl-10 linoleate | Nikkol Decaglyn 1-LN (Nikko) | 12 |
| Polyglyceryl-6 pentaoleate | Nikkol Hexaglyn 5-O (Nikko) | <10 |
| Polyglyceryl-3 dioleate | Cremophor GO32 (BASF) | <10 |
| Polyglyceryl-3 distearate | Cremophor GS32 (BASF) | <10 |
| Polyglyceryl-4 pentaoleate | Nikkol Tetraglyn 5-O (Nikko) | <10 |
| Polyglyceryl-6 dioleate | Caprol® 6G20 (ABITEC); Hodag PGO-62 (Calgene), PLUROL OLEIQUE CC 497 (Gattefosse) | 8.5 |
| Polyglyceryl-2 dioleate | Nikkol DGDO (Nikko) | 7 |
| Polyglyceryl-10 trioleate | Nikkol Decaglyn 3-O (Nikko) | 7 |
| Polyglyceryl-10 pentaoleate | Nikkol Decaglyn 5-O (Nikko) | 3.5 |
| Polyglyceryl-10 septaoleate | Nikkol Decaglyn 7-O (Nikko) | 3 |
| Polyglyceryl-10 tetraoleate | Caprol® 10G4O (ABITEC); Hodag PGO-62 (CALGENE), Drewpol 10-4-O (Stepan) | 6.2 |
| Polyglyceryl-10 decaisostearate | Nikkol Decaglyn 10-IS (Nikko) | <10 |
| Polyglyceryl-101 decaoleate | Drewpol 10-10-O (Stepan), Caprol 10G10O (ABITEC), Nikkol Decaglyn 10-O | 3.5 |
| Polyglyceryl-10 mono, dioleate | Caprol® PGE 860 (ABITEC) | 11 |
| Polyglyceryl polyricinoleate | Polymuls (Henkel) | 3–20 |

2.7. Propylene Glycol Fatty Acid Esters

Esters of propylene glycol and fatty acids are suitable surfactants for use in the present invention. In this surfactant class, preferred hydrophobic surfactants include propylene glycol monolaurate (Lauroglycol FCC), propylene glycol ricinoleate (Propymuls), propylene glycol monooleate (Myverol P-06), propylene glycol dicaprylate/dicaprate (Captex® 200), and propylene glycol dioctanoate (Captex® 800). Examples of surfactants of this class are given in Table 8.

TABLE 8

Propylene Glycol Fatty Acid Esters

| COMPOUND | COMMERCIAL PRODUCT (Supplier) | HLB |
|---|---|---|
| Propylene glycol monocaprylate | Capryol 90 (Gattefosse), Nikkol Sefsol 218 (Nikko) | <10 |
| Propylene glycol monolaurate | Lauroglycol 90 (Gattefosse), Lauroglycol FCC (Gattefosse) | <10 |
| Propylene glycol oleate | Lutrol OP2000 (BASF) | <10 |
| Propylene glycol myristate | Mirpyl | <10 |
| Propylene glycol monostearate | ADM PGME-03 (ADM), LIPO PGMS (Lipo Chem.), Aldo® PGHMS (Lonza) | 3–4 |
| Propylene glycol hydroxy stearate | | <10 |
| Propylene glycol ricinoleate | PROPYMULS (Henkel) | <10 |
| Propylene glycol isostearate | | <10 |
| Propylene glycol monooleate | Myverol P-O6 (Eastman) | <10 |
| Propylene glycol dicaprylate/dicaprate | Captex® 200 (ABITEC), Miglyol® 840 (Huls), Neobee® M-20 (Stepan) | >6 |
| Propylene glycol dioctanoate | Captex® 800 (ABITEC) | >6 |
| Propylene glycol caprylate/caprate | LABRAFAC PG (Gattefosse) | >6 |
| Propylene glycol dilaurate | | >6 |
| Propylene glycol distearate | Kessco® PGDS (Stepan) | >6 |
| Propylene glycol dicaprylate | Nikkol Sefsol 228 (Nikko) | >6 |
| Propylene glycol dicaprate | Nikkol PDD (Nikko) | >6 |

2.8. Mixtures of Propylene Glycol Esters—Glycerol Esters

In general, mixtures of surfactants are also suitable for use in the present invention. In particular, mixtures of propylene glycol fatty acid esters and glycerol fatty acid esters are suitable and are commercially available. One preferred mixture is composed of the oleic acid esters of propylene glycol and glycerol (Arlacel 186). Examples of these surfactants are shown in Table 9.

TABLE 9

Glycerol/Propylene Glycol Fatty Acid Esters

| COMPOUND | COMMERCIAL PRODUCT (Supplier) | HLB |
|---|---|---|
| Oleic | ATMOS 300, ARLACEL 186 (ICI) | 3–4 |
| Stearic | ATMOS 150 | 3–4 |

2.9. Mono- and Diglycerides

A particularly important class of surfactants is the class of mono- and diglycerides. These surfactants are generally hydrophobic. Preferred hydrophobic surfactants in this class of compounds include glyceryl monooleate (Peceol), glyceryl 15 ricinoleate, glyceryl laurate, glyceryl dilaurate (Capmul® GDL), glyceryl dioleate (Capmul® GDO), glyceryl mono/dioleate (Capmul® GMO-K), glyceryl caprylate/caprate (Capmul® MCM), caprylic acid mono/diglycerides (Imwitor® 988), and mono- and diacetylated monoglycerides (Myvacet® 9-45). Examples of these surfactants are given in Table 10.

TABLE 10

Mono- and Diglyceride Surfactants

| COMPOUND | COMMERCIAL PRODUCT (Supplier) | HLB |
|---|---|---|
| Monopalmitolein (C16:1) | (Larodan) | <10 |
| Monoelaidin (C18:1) | (Larodan) | <10 |
| Monocaproin (C6) | (Larodan) | <10 |

TABLE 10-continued

Mono- and Diglyceride Surfactants

| COMPOUND | COMMERCIAL PRODUCT (Supplier) | HLB |
|---|---|---|
| Monocaprylin | (Larodan) | <10 |
| Monocaprin | (Larodan) | <10 |
| Monolaurin | (Larodan) | <10 |
| Glyceryl monomyristate (C14) | Nikkol MGM (Nikko) | 3–4 |
| Glyceryl monooleate (C18:1) | PECOL (Gattefosse), Hodag GMO-D, Nikkol MGO (Nikko) | 3–4 |
| Glyceryl monooleate | RYLO series (Danisco), DIMODAN series (Danisco), EMULDAN (Danisco), ALDO ® MO FG (Lonza), Kessco GMO (Stepan), MONOMULS ® series (Henkel), TEGIN O, DREWMULSE GMO (Stepan), Atlas G-695 (ICI), GMOrphic 80 (Eastman), ADM DMG-40, 70, and 100 (ADM), Myverol (Eastman) | 3–4 |
| Glycerol monooleate/linoleate | OLICINE (Gattefosse) | 3–4 |
| Glycerol monolinoleate | Maisine (Gattefosse), MYVEROL 18-92, Myverol 18-06 (Eastman) | 3–4 |
| Glyceryl ricinoleate | Softigen ® 701 (Hüls), HODAG GMR-D (Calgene), ALDO ® MR (Lonza) | 6 |
| Glyceryl monolaurate | ALDO ® MLD (Lonza), Hodag GML (Calgene) | 6.8 |
| Glycerol monopalmitate | Emalex GMS-P (Nihon) | 4 |
| Glycerol monostearate | Capmul ® GMS (ABITEC), Myvaplex (Eastman), IMWITOR ® 191 (Hüls), CUTINA GMS, Aldo ® MS (Lonza), Nikkol MGS series (Nikko) | 5–9 |
| Glyceryl mono-, dioleate | Capmul ® GMO-K (ABITEC) | <10 |
| Glyceryl palmitic/stearic | CUTINA MD-A, ESTAGEL-G18 | <10 |
| Glyceryl acetate | Lamegin ® EE (Grün au GmbH) | <10 |
| Glyceryl laurate | Imwitor ® 312 (Hüls), Monomuls ® 90-45 (Grunau GmbH), Aldo ® MLD (Lonza) | 4 |
| Glyceryl citrate/lactate/oleate/linoleate | Imwitor ® 375 (Hüls) | <10 |
| Glyceryl caprylate | Imwitor ® 308 (Hüls), Capmul ® MCMC8 (ABITEC) | 5–6 |
| Glyceryl caprylate/caprate | Capmul ® MCM (ABITEC) | 5–6 |
| Caprylic acid mono, diglycerides | Imwitor ® 988 (Hüls) | 5–6 |
| Caprylic/capric glycerides | Imwitor ® 742 (Hüls) | <10 |
| Mono- and diacetylated monoglycerides | Myvacet ® 9-45, Myvacet ® 9-40, Myvacet ® 9-08 (Eastman), Lamegin ® (Grunau) | 3.8–4 |
| Glyceryl monostearate | Aldo ® MS, Arlacel 129 (ICI), LIPO GMS (Lipo Chem.), Imwitor ® 191 (Hüls), Myvaplex (Eastman) | 4.4 |
| Lactic acid esters of mono, di-glycerides | LAMEGIN GLP (Henkel) | <10 |
| Dicaproin (C6) | (Larodan) | <10 |
| Dicaprin (C10) | (Larodan) | <10 |
| Dioctanoin (C8) | (Larodan) | <10 |
| Dimyristin (C14) | (Larodan) | <10 |
| Dipalmitin (C16) | (Larodan) | <10 |
| Distearin | (Larodan) | <10 |
| Glyceryl dilaurate (C12) | Capmul ® GDL (ABITEC) | 3–4 |
| Glyceryl dioleate | Capmul ® GDO (ABITEC) | 3–4 |
| Glycerol esters of fatty acids | GELUCIRE 39/01 (Gattefosse), GELUCIRE 43/01 (Gattefosse) GELUCIRE 37/06 (Gattefosse) | 1 6 |
| Dipalmitolein (C16:1) | (Larodan) | <10 |
| 1,2 and 1,3-diolein (C18:1) | (Larodan) | <10 |
| Dielaidin (C18:1) | (Larodan) | <10 |
| Dilinolein (C18:2) | (Larodan) | <10 |

2.10. Sterol and Sterol Derivatives

Sterols and derivatives of sterols are suitable surfactants for use in the present invention. These surfactants can be hydrophilic or hydrophobic. Preferred derivatives include the polyethylene glycol derivatives. A preferred hydrophobic surfactant in this class is cholesterol. A preferred hydrophilic surfactant in this class is PEG-24 cholesterol ether (Solulan C-24). Examples of surfactants of this class are shown in Table 11.

TABLE 11

Sterol and Sterol Derivative Surfactants

| COMPOUND | COMMERCIAL PRODUCT (Supplier) | HLB |
|---|---|---|
| Cholesterol, sitosterol, lanosterol | | <10 |
| PEG-24 cholesterol ether | Solulan C-24 (Amerchol) | >10 |
| PEG-30 cholestanol | Nikkol DHC (Nikko) | >10 |
| Phytosterol | GENEROL series (Henkel) | <10 |
| PEG-25 phyto sterol | Nikkol BPSH-25 (Nikko) | >10 |
| PEG-5 soya sterol | Nikkol BPS-5 (Nikko) | <10 |
| PEG-10 soya sterol | Nikkol BPS-10 (Nikko) | <10 |
| PEG-20 soya sterol | Nikkol BPS-20 (Nikko) | <10 |
| PEG-30 soya sterol | Nikkol BPS-30 (Nikko) | >10 |

2.11. Polyethylene Glycol Sorbitan Fatty Acid Esters

A variety of PEG-sorbitan fatty acid esters are available and are suitable for use as surfactants in the present invention. In general, these surfactants are hydrophilic, although several hydrophobic surfactants of this class can be used. Among the PEG-sorbitan fatty acid esters, preferred hydrophilic surfactants include PEG-20 sorbitan monolaurate (Tween-20), PEG-20 sorbitan monopalmitate (Tween-40), PEG-20 sorbitan monostearate (Tween-60), and PEG-20 sorbitan monooleate (Tween-80). Examples of these surfactants are shown in Table 12.

TABLE 12

PEG-Sorbitan Fatty Acid Esters

| COMPOUND | COMMERCIAL PRODUCT (Supplier) | HLB |
|---|---|---|
| PEG-10 sorbitan laurate | Liposorb L-10 (Lipo Chem.) | >10 |
| PEG-20 sorbitan monolaurate | Tween-20 (Atlas/ICI), Crillet 1 (Croda), DACOL MLS 20 (Condea) | 17 |
| PEG-4 sorbitan monolaurate | Tween-21 (Atlas/ICI), Crillet 11 (Croda) | 13 |
| PEG-80 sorbitan monolaurate | Hodag PSML-80 (Calgene); T-Maz 28 | >10 |
| PEG-6 sorbitan monolaurate | (Nikkol GL-1 (Nikko) | 16 |
| PEG-20 sorbitan monopalmitate | Tween-40 (Atlas/ICI), Crillet 2 (Croda) | 16 |
| PEG-20 sorbitan monostearate | Tween-60 (Atlas/ICI), Crillet 3 (Croda) | 15 |

TABLE 12-continued

PEG-Sorbitan Fatty Acid Esters

| COMPOUND | COMMERCIAL PRODUCT (Supplier) | HLB |
|---|---|---|
| PEG-4 sorbitan monostearate | Tween-61 (Atlas/ICI), Crillet 31 (Croda) | 9.6 |
| PEG-8 sorbitan monostearate | DACOL MSS (Condea) | >10 |
| PEG-6 sorbitan monostearate | Nikkol TS106 (Nikko) | 11 |
| PEG-20 sorbitan tristearate | Tween-65 (Atlas/ICI), Crillet 35 (Croda) | 11 |
| PEG-6 sorbitan tetrastearate | (Nikkol GS-6 (Nikko) | 3 |
| PEG-60 sorbitan tetrastearate | Nikkol GS-460 (Nikko) | 13 |
| PEG-5 sorbitan monooleate | Tween-81 (Atlas/ICI), Crillet 41 (Croda) | 10 |
| PEG-6 sorbitan monooleate | (Nikkol TO-106 (Nikko) | 10 |
| PEG-20 sorbitan monooleate | Tween-80 (Atlas/ICI), Crillet 4 (Croda) | 15 |
| PEG-40 sorbitan oleate | Emalex ET 8040 (Nihon Emulsion) | 18 |
| PEG-20 sorbitan trioleate | Tween-85 (Atlas/ICI), Crillet 45 (Croda) | 11 |
| PEG-6 sorbitan tetraoleate | (Nikkol GO-4 (Nikko) | 8.5 |
| PEG-30 sorbitan tetraoleate | (Nikkol GO-430 (Nikko) | 12 |
| PEG-40 sorbitan tetraoleate | (Nikkol GO-440 (Nikko) | 13 |
| PEG-20 sorbitan monoisostearate | Tween-120 (Atlas/ICI), Crillet 6 (Croda) | >10 |
| PEG sorbitol hexaoleate | Atlas G-1086 (ICI) | 10 |
| PEG-6 sorbitol hexastearate | Nikkol GS-6 (Nikko) | 3 |

2.12. Polyethylene Glycol Alkyl Ethers

Ethers of polyethylene glycol and alkyl alcohols are suitable surfactants for use in the present invention. Preferred hydrophobic ethers include PEG-3 oleyl ether (Volpo 3) and PEG-4 lauryl ether (Brij 30). Examples of these surfactants are shown in Table 13.

TABLE 13

Polyethylene Glycol Alkyl Ethers

| COMPOUND | COMMERCIAL PRODUCT (Supplier) | HLB |
|---|---|---|
| PEG-2 oleyl ether, oleth-2 | Brij 92/93 (Atlas/ICI) | 4.9 |
| PEG-3 oleyl ether, oleth-3 | Volpo 3 (Croda) | <10 |
| PEG-5 oleyl ether, oleth-5 | Volpo 5 (Croda) | <10 |
| PEG-10 oleyl ether, oleth-10 | Volpo 10 (Croda), Brij 96/97 (Atlas/ICI) | 12 |
| PEG-20 oleyl ether, oleth-20 | Volpo 20 (Croda), Brij 98/99 (Atlas/ICI) | 15 |
| PEG-4 lauryl ether, laureth-4 | Brij 30 (Atlas/ICI) | 9.7 |
| PEG-9 lauryl ether | | >10 |
| PEG-23 lauryl ether, laureth-23 | Brij 35 (Atlas/ICI) | 17 |
| PEG-2 cetyl ether | Brij 52 (ICI) | 5.3 |
| PEG-10 cetyl ether | Brij 56 (ICI) | 13 |
| PEG-20 cetyl ether | Brij 58 (ICI) | 16 |
| PEG-2 stearyl ether | Brij 72 (ICI) | 4.9 |
| PEG-10 stearyl ether | Brij 76 (ICI) | 12 |
| PEG-20 stearyl ether | Brij 78 (ICI) | 15 |
| PEG-100 stearyl ether | Brij 700 (ICI) | >10 |

2.13. Sugar Esters

Esters of sugars are suitable surfactants for use in the present invention. Preferred hydrophilic surfactants in this class include sucrose monopalmitate and sucrose monolaurate. Examples of such surfactants are shown in Table 14.

TABLE 14

Sugar Ester Surfactants

| COMPOUND | COMMERCIAL PRODUCT (Supplier) | HLB |
|---|---|---|
| Sucrose distearate | SUCRO ESTER 7 (Gattefosse), Crodesta F-10 (Croda) | 3 |
| Sucrose distearate/monostearate | SUCRO ESTER 11 (Gattefosse), Crodesta F-110 (Croda) | 12 |
| Sucrose dipalmitate | | 7.4 |
| Sucrose monostearate | Crodesta F-160 (Croda) | 15 |
| Sucrose monopalmitate | SUCRO ESTER 15 (Gattefosse) | >10 |
| Sucrose monolaurate | Saccharose monolaurate 1695 (Mitsubishi-Kasei) | 15 |

2.14. Polyethylene Glycol Alkyl Phenols

Several hydrophilic PEG-alkyl phenol surfactants are available, and are suitable for use in the present invention. Examples of these surfactants are shown in Table 15.

TABLE 15

Polyethylene Glycol Alkyl Phenol Surfactants

| COMPOUND | COMMERCIAL PRODUCT (Supplier) | HLB |
|---|---|---|
| PEG-10-100 nonyl phenol | Triton X series (Robm & Haas), Igepal CA series (GAF, USA), Antarox CA series (GAF, UK) | >10 |
| PEG-15-100 octyl phenol ether | Triton N-series (Rohm & Haas), Igepal CO series (GAF, USA), Antarox CO series (GAF, UK) | >10 |

2.15. Polyoxyethylene-Polyoxypropylene Block Copolymers

The POE-POP block copolymers are a unique class of polymeric surfactants. The unique structure of the surfactants, with hydrophilic POE and hydrophobic POP moieties in well-defined ratios and positions, provides a wide variety of surfactants suitable for use in the present invention. These surfactants are available under various trade names, including Synperonic PE series (ICI); Pluronic® series (BASF), Emkalyx, Lutrol (BASF), Supronic, Monolan, Pluracare, and Plurodac. The generic term for these polymers is "poloxamer" (CAS 9003-11-6). These polymers have the formula:

$$HO(C_2H_4O)_a(C_3H_6O)_b(C_2H_4O)_aH$$

where "a" and "b" denote the number of polyoxyethylene and polyoxypropylene units, respectively.

Preferred hydrophilic surfactants of this class include Poloxamers 108, 188, 217, 238, 288, 338, and 407. Preferred hydrophobic surfactants in this class include Poloxamers 124, 182, 183, 212, 331, and 335.

Examples of suitable surfactants of this class are shown in Table 16. Since the compounds are widely available, commercial sources are not listed in the Table. The compounds are listed by generic name, with the corresponding "a" and "b" values.

TABLE 16

POE-POP Block Copolymers

| COMPOUND | a, b values in $HO(C_2H_4O)_a(C_3H_6O)_b(C_2H_4O)_aH$ | HLB |
|---|---|---|
| Poloxamer 105 | a = 11 b = 16 | 8 |
| Poloxamer 108 | a = 46 b = 16 | >10 |

TABLE 16-continued

POE-POP Block Copolymers

| COMPOUND | a, b values in HO(C$_2$H$_4$O)$_a$(C$_3$H$_6$O)$_b$(C$_2$H$_4$O)$_a$H | HLB |
|---|---|---|
| Poloxamer 122 | a = 5 b = 21 | 3 |
| Poloxamer 123 | a = 7 b = 21 | 7 |
| Poloxamer 124 | a = 11 b = 21 | >7 |
| Poloxamer 181 | a = 3 b = 30 | |
| Poloxamer 182 | a = 8 b = 30 | 2 |
| Poloxamer 183 | a = 10 b = 30 | |
| Poloxamer 184 | a = 13 b = 30 | |
| Poloxamer 185 | a = 19 b = 30 | |
| Poloxamer 188 | a = 75 b = 30 | 29 |
| Poloxamer 212 | a = 8 b = 35 | |
| Poloxamer 215 | a = 24 b = 35 | |
| Poloxamer 217 | a = 52 b = 35 | |
| Poloxamer 231 | a = 16 b = 39 | |
| Poloxamer 234 | a = 22 b = 39 | |
| Poloxamer 235 | a = 27 b = 39 | |
| Poloxamer 237 | a = 62 b = 39 | 24 |
| Poloxamer 238 | a = 97 b = 39 | |
| Poloxamer 282 | a = 10 b = 47 | |
| Poloxamer 284 | a = 21 b = 47 | |
| Poloxamer 288 | a = 122 b = 47 | >10 |
| Poloxamer 331 | a = 7 b = 54 | 0.5 |
| Poloxamer 333 | a = 20 b = 54 | |
| Poloxamer 334 | a = 31 b = 54 | |
| Poloxamer 335 | a = 38 b = 54 | |
| Poloxamer 338 | a = 128 b = 54 | |
| Poloxamer 401 | a = 6 b = 67 | |
| Poloxamer 402 | a = 13 b = 67 | |
| Poloxamer 403 | a = 21 b = 67 | |
| Poloxamer 407 | a = 98 b = 67 | |

2.16. Sorbitan Fatty Acid Esters

Sorbitan esters of fatty acids are suitable surfactants for use in the present invention. Among these esters, preferred hydrophobic surfactants include sorbitan monolaurate (Arlacel 20), sorbitan monopalmitate (Span-40), sorbitan monooleate (Span-80), sorbitan monostearate, and sorbitan tristearate. Examples of these surfactants are shown in Table 17.

TABLE 17

Sorbitan Fatty Acid Ester Surfactants

| COMPOUND | COMMERCIAL PRODUCT (Supplier) | HLB |
|---|---|---|
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |
| Sorbitan trioleate | Span-85 (Atlas/ICI), Crill 45 (Croda), Nikkol SO-30 (Nikko) | 4.3 |
| Sorbitan sesquioleate | Arlacel-C (ICI), Crill 43 (Croda), Nikkol SO-15 (Nikko) | 3.7 |
| Sorbitan tristearate | Span-65 (Atlas/ICI) Crill 35 (Croda), Nikkol SS-30 (Nikko) | 2.1 |
| Sorbitan monoisostearate | Crill 6 (Croda), Nikkol SI-10 (Nikko) | 4.7 |
| Sorbitan sesquistearate | Nikkol SS-15 (Nikko) | 4.2 |

2.17. Lower Alcohol Fatty Acid Esters

Esters of lower alcohols (C$_2$ to C$_4$) and fatty acids (C$_8$ to C$_{18}$) are suitable surfactants for use in the present invention. Among these esters, preferred hydrophobic surfactants include ethyl oleate (Crodamol EO), isopropyl myristate (Crodamol IPM), and isopropyl palmitate (Crodamol IPP). Examples of these surfactants are shown in Table 18.

TABLE 18

Lower Alcohol Fatty Acid Ester Surfactants

| COMPOUND | COMMERCIAL PRODUCT (Supplier) | HLB |
|---|---|---|
| Ethyl oleate | Crodamol EO (Croda), Nikkol EOO (Nikko) | <10 |
| Isopropyl myristate | Crodamol IPM (Croda) | <10 |
| Isopropyl palmitate | Crodamol IPP (Croda) | <10 |
| Ethyl linoleate | Nikkol VF-E (Nikko) | <10 |
| Isopropyl linoleate | Nikkol VF-IP (Nikko) | <10 |

2.18. Ionic Surfactants

Ionic surfactants, including cationic, anionic and zwitterionic surfactants, are suitable hydrophilic surfactants for use in the present invention. Preferred anionic surfactants include fatty acid salts and bile salts. Preferred cationic surfactants include carnitines. Specifically, preferred ionic surfactants include sodium oleate, sodium lauryl sulfate, sodium lauryl sarcosinate, sodium dioctyl sulfosuccinate, sodium cholate, sodium taurocholate; lauroyl carnitine; palmitoyl carnitine; and myristoyl carnitine. Examples of such surfactants are shown in Table 19. For simplicity, typical counterions are shown in the entries in the Table. It will be appreciated by one skilled in the art, however, that any bioacceptable counterion may be used. For example, although the fatty acids are shown as sodium salts, other cation counterions can also be used, such as alkali metal cations or ammonium. Unlike typical non-ionic surfactants, these ionic surfactants are generally available as pure compounds, rather than commercial (proprietary) mixtures. Because these compounds are readily available from a variety of commercial suppliers, such as Aldrich, Sigma, and the like, commercial sources are not generally listed in the Table.

TABLE 19

Ionic Surfactants

| COMPOUND | HLB |
|---|---|
| FATTY ACID SALTS | >10 |
| Sodium caproate | |
| Sodium caprylate | |
| Sodium caprate | |
| Sodium laurate | |
| Sodium myristate | |
| Sodium myristolate | |
| Sodium palmitate | |
| Sodium palmitoleate | |
| Sodium oleate | 18 |
| Sodium ricinoleate | |
| Sodium linoleate | |
| Sodium linolenate | |
| Sodium stearate | |
| Sodium lauryl sulfate (dodecyl) | 40 |
| Sodium tetradecyl sulfate | |
| Sodium lauryl sarcosinate | |
| Sodium dioctyl sulfosuccinate [sodium docusate (Cytec)] | |
| BILE SALTS | >10 |
| Sodium cholate | |
| Sodium taurocholate | |
| Sodium glycocholate | |
| Sodium deoxycholate | |
| Sodium taurodeoxycholate | |
| Sodium glycodeoxycholate | |
| Sodium ursodeoxycholate | |
| Sodium chenodeoxycholate | |
| Sodium taurochenodeoxycholate | |
| Sodium glyco cheno deoxycholate | |
| Sodium cholylsarcosinate | |

TABLE 19-continued

Ionic Surfactants

| COMPOUND | HLB |
|---|---|
| Sodium N-methyl taurocholate | |
| Sodium lithocholate | |
| PHOSPHOLIPIDS | |
| Egg/Soy lecithin [Epikuron ™ (Lucas Meyer), Ovothin ™ (Lucas Meyer)] | |
| Lyso egg/soy lecithin | |
| Hydroxylated lecithin | |
| Lysophosphatidylcholine | |
| Cardiolipin | |
| Sphingomyelin | |
| Phosphatidylcholine | |
| Phosphatidyl ethanolamine | |
| Phosphatidic acid | |
| Phosphatidyl glycerol | |
| Phosphatidyl serine | |
| PHOSPHORIC ACID ESTERS | |
| Diethanolammonium polyoxyethylene-10 oleyl ether phosphate | |
| Esterification products of fatty alcohols or fatty alcohol ethoxylates with phosphoric acid or anhydride | |
| CARBOXYLATES | |
| Ether carboxylates (by oxidation of terminal OH group of fatty alcohol ethoxylates) | |
| Succinylated monoglycerides [LAMEGIN ZE (Henkel)] | |
| Sodium stearyl fumarate | |
| Stearoyl propylene glycol hydrogen succinate | |
| Mono/diacetylated tartaric acid esters of mono- and diglycerides | |
| Citric acid esters of mono-, diglycerides | |
| Glyceryl-lacto esters of fatty acids (CFR ref. 172.852) | |
| Acyl lactylates: | |
| lactylic esters of fatty acids | |
| calcium/sodium stearoyl-2-lactylate | |
| calcium/sodium stearoyl lactylate | |
| Alginate salts | |
| Propylene glycol alginate | |
| SULFATES AND SULFONATES | |
| Ethoxylated alkyl sulfates | |
| Alkyl benzene sulfones | |
| α-olefin sulfonates | |
| Acyl isethionates | |
| Acyl taurates | |
| Alkyl glyceryl ether sulfonates | |
| Octyl sulfosuccinate disodium | |
| Disodium undecylenamideo-MEA-sulfosuccinate | |
| CATIONIC Surfactants | >10 |
| Lauroyl carnitine | |
| Palmitoyl carnitine | |
| Myristoyl carnitine | |
| Hexadecyl triammonium bromide | |
| Decyl trimethyl ammonium bromide | |
| Cetyl trimethyl ammonium bromide | |
| Dodecyl ammonium chloride | |
| Alkyl benzyldimethylammonium salts | |
| Diisobutyl phenoxyethoxydimethyl benzylammonium salts | |
| Alkylpyridinium salts | |
| Betaines (trialkylglycine): | |
| Lauryl betaine (N-lauryl,N,N-dimethylglycine) | |
| Ethoxylated amines: | |
| Polyoxyethylene-15 coconut amine | |

2.19. Unionized Ionizable Surfactants

Ionizable surfactants, when present in their unionized (neutral, non-salt) form, are hydrophobic surfactants suitable for use in the compositions and methods of the present invention. Particular examples of such surfactants include free fatty acids, particularly $C_6$–$C_{22}$ fatty acids, and bile acids. More specifically, suitable unionized ionizable surfactants include the free fatty acid and bile acid forms of any of the fatty acid salts and bile salts shown in Table 19.

2.20 Preferred Surfactants and Surfactant Combinations

Among the above-listed surfactants, several combinations are preferred. In all of the preferred combinations, the carrier includes at least one hydrophilic surfactant. Preferred non-ionic hydrophilic surfactants include alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols, derivatives, and analogues thereof; polyoxyethylene vegetable oils; polyoxyethylene hydrogenated vegetable oils; reaction mixtures of polyols with fatty acids, glycerides, vegetable oils, hydrogenated vegetable oils, and sterols; sugar esters, sugar ethers; sucroglycerides; and mixtures thereof.

More preferably, the non-ionic hydrophilic surfactant is selected from the group consisting of polyoxyethylene alkylethers; polyethylene glycol fatty acids esters; polyethylene glycol glycerol fatty acid esters; polyoxyethylene sorbitan fatty acid esters; polyoxyethylene-polyoxypropylene block copolymers; polyglyceryl fatty acid esters; polyoxyethylene glycerides; polyoxyethylene vegetable oils; and polyoxyethylene hydrogenated vegetable oils. The glyceride can be a monoglyceride, diglyceride, triglyceride, or a mixture.

Also preferred are non-ionic hydrophilic surfactants that are reaction mixtures of polyols and fatty acids, glycerides, vegetable oils, hydrogenated vegetable oils or sterols. These reaction mixtures are largely composed of the transesterification products of the reaction, along with often complex mixtures of other reaction products. The polyol is preferably glycerol, ethylene glycol, polyethylene glycol, sorbitol, propylene glycol, pentaerythritol, or a saccharide.

Several particularly preferred carrier compositions are those which include as a non-ionic hydrophilic surfactant PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, or a poloxamer.

Among these preferred surfactants, more preferred are PEG-20 laurate, PEG-20 oleate, PEG-35 castor oil, PEG-40 palm kernel oil, PEG-40 hydrogenated castor oil, PEG-60 corn oil, PEG-25 glyceryl trioleate, polyglyceryl-1O laurate, PEG-6 caprate/caprylate glycerides, PEG-8 caprate/ caprylate glycerides, PEG-30 cholesterol, polysorbate 20, polysorbate 80, POE-9 lauryl ether, POE-23 lauryl ether, POE-10 oleyl ether, PEG-24 cholesterol, sucrose monostearate, sucrose monolaurate and poloxamers. Most preferred are PEG-35 castor oil, PEG-40 hydrogenated castor oil, PEG-60 corn oil, PEG-25 glyceryl trioleate, PEG-6 caprate/caprylate glycerides, PEG-8 caprate/caprylate glycerides, polysorbate 20, polysorbate 80, tocopheryl PEG-1000 succinate, PEG-24 cholesterol, and hydrophilic poloxamers.

The hydrophilic surfactant can also be, or include as a component, an ionic surfactant. Preferred ionic surfactants include alkyl ammonium salts; bile acids and salts, analogues, and derivatives thereof; fusidic acid and derivatives thereof; fatty acid conjugates of amino acids, oligopeptides, and polypeptides; glyceride esters of amino acids, oligopeptides, and polypeptides; acyl lactylates; mono- and diacetylated tartaric acid esters of mono- and diglycerides; succinylated monoglycerides; citric acid esters of mono- and diglycerides; alginate salts; propylene glycol alginate; lecithins and hydrogenated lecithins; lysolecithin and hydrogenated lysolecithins; lysophospholipids and derivatives thereof; phospholipids and derivatives thereof; salts of alkylsulfates; salts of fatty acids; sodium docusate; carnitines; and mixtures thereof.

More preferable ionic surfactants include bile acids and salts, analogues, and derivatives thereof; lecithins, lysolecithin, phospholipids, lysophospholipids and derivatives thereof; salts of alkylsulfates; salts of fatty acids; sodium docusate; acyl lactylates; mono- and diacetylated tartaric acid esters of mono- and diglycerides; succinylated monoglycerides; citric acid esters of mono- and diglycerides; carnitines; and mixtures thereof.

More specifically, preferred ionic surfactants are lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, taurodeoxycholate, chenodeoxycholate, glycodeoxycholate, glycochenodeoxycholate, taurochenodeoxycholate, ursodeoxycholate, tauroursodeoxycholate, glycoursodeoxycholate, cholylsarcosine, N-methyl taurocholate, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Particularly preferred ionic surfactants are lecithin, lysolecithin, phosphatidylcholine, phosphatidylethanolamine, phosphatidylglycerol, lysophosphatidylcholine, PEG-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, taurodeoxycholate, glycodeoxycholate, cholylsarcosine, caproate, caprylate, caprate, laurate, oleate, lauryl sulfate, docusate, and salts and mixtures thereof, with the most preferred ionic surfactants being lecithin, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, taurocholate, caprylate, caprate, oleate, lauryl sulfate, docusate, and salts and mixtures thereof.

The carrier of the present compositions includes at least two surfactants, at least one of which is hydrophilic. In one embodiment, the present invention includes at two surfactants that are hydrophilic, and preferred hydrophilic surfactants are listed above. In another embodiment, the carrier includes at least one hydrophilic surfactant and at least one hydrophobic surfactant. In this embodiment, preferred hydrophobic surfactants are alcohols; polyoxyethylene alkylethers; fatty acids; glycerol fatty acid esters; acetylated glycerol fatty acid esters; lower alcohol fatty acids esters; polyethylene glycol fatty acids esters; polyethylene glycol glycerol fatty acid esters; polypropylene glycol fatty acid esters; polyoxyethylene glycerides; lactic acid esters of mono/diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; and polyoxyethylene hydrogenated vegetable oils.

As with the hydrophilic surfactants, hydrophobic surfactants can be reaction mixtures of polyols and fatty acids, glycerides, vegetable oils, hydrogenated vegetable oils, and sterols.

Preferably, the hydrophobic surfactant is selected from the group consisting of fatty acids; lower alcohol fatty acid esters; polyethylene glycol glycerol fatty acid esters; polypropylene glycol fatty acid esters; polyoxyethylene glycerides; glycerol fatty acid esters; acetylated glycerol fatty acid esters; lactic acid esters of mono/diglycerides; sorbitan fatty acid esters; polyoxyethylene sorbitan fatty acid esters; polyoxyethylene-polyoxypropylene block copolymers; polyoxyethylene vegetable oils; polyoxyethylene hydrogenated vegetable oils; and reaction mixtures of polyols and fatty acids, glycerides, vegetable oils, hydrogenated vegetable oils, and sterols.

More preferred are lower alcohol fatty acids esters; polypropylene glycol fatty acid esters; propylene glycol fatty acid esters; glycerol fatty acid esters; acetylated glycerol fatty acid esters; lactic acid esters of mono/diglycerides; sorbitan fatty acid esters; polyoxyethylene vegetable oils; and mixtures thereof, with glycerol fatty acid esters and acetylated glycerol fatty acid esters being most preferred. Among the glycerol fatty acid esters, the esters are preferably mono- or diglycerides, or mixtures of mono- and diglycerides, where the fatty acid moiety is a $C_6$ to $C_{22}$ fatty acid.

Also preferred are hydrophobic surfactants that are the reaction mixture of polyols and fatty acids, glycerides, vegetable oils, hydrogenated vegetable oils, and sterols. Preferred polyols are polyethylene glycol, sorbitol, propylene glycol, and pentaerythritol.

Specifically preferred hydrophobic surfactants include myristic acid; oleic acid; lauric acid; stearic acid; palmitic acid; PEG 1-4 stearate; PEG 2-4 oleate; PEG-4 dilaurate; PEG-4 dioleate; PEG-4 distearate; PEG-6 dioleate; PEG-6 distearate; PEG-8 dioleate; PEG 3-16 castor oil; PEG 5-10 hydrogenated castor oil; PEG 6-20 corn oil; PEG 6-20 almond oil; PEG-6 olive oil; PEG-6 peanut oil; PEG-6 palm kernel oil; PEG-6 hydrogenated palm kernel oil; PEG-4 capric/caprylic triglyceride, mono, di, tri, tetra esters of vegetable oil and sorbitol; pentaerythrityl di, tetra stearate, isostearate, oleate, caprylate, or caprate; polyglyceryl 2-4 oleate, stearate, or isostearate; polyglyceryl 4-10 pentaoleate; polyglyceryl-3 dioleate; polyglyceryl-6 dioleate; polyglyceryl-10 trioleate; polyglyceryl-3 distearate; propylene glycol mono- or diesters of a $C_6$ to $C_{20}$ fatty acid; monoglycerides of $C_6$ to $C_{20}$ fatty acids; acetylated monoglycerides of $C_6$ to $C_{20}$ fatty acids; diglycerides of $C_6$ to $C_{20}$ fatty acids; lactic acid derivatives of monoglycerides; lactic acid derivatives of diglycerides; cholesterol; phytosterol; PEG 5-20 soya sterol; PEG-6 sorbitan tetra, hexastearate; PEG-6 sorbitan tetraoleate; sorbitan monolaurate; sorbitan monopalmitate; sorbitan mono, trioleate; sorbitan mono, tristearate; sorbitan monoisostearate; sorbitan sesquioleate; sorbitan sesquistearate; PEG 2-5 oleyl ether; POE 2-4 lauryl ether; PEG-2 cetyl ether; PEG-2 stearyl ether; sucrose distearate; sucrose dipalmitate; ethyl oleate; isopropyl myristate; isopropyl palmitate; ethyl linoleate; isopropyl linoleate; and poloxamers.

Among the specifically preferred hydrophobic surfactants, most preferred are oleic acid; lauric acid; glyceryl monocaprate; glyceryl monocaprylate; glyceryl monolaurate; glyceryl monooleate; glyceryl dicaprate; glyceryl dicaprylate; glyceryl dilaurate; glyceryl dioleate; acetylated monoglycerides; propylene glycol oleate; propylene glycol laurate; polyglyceryl-3 oleate; polyglyceryl-6 dioleate; PEG-6 corn oil; PEG-20 corn oil; PEG-20 almond oil; sorbitan monooleate; sorbitan monolaurate; POE-4 lauryl ether; POE-3 oleyl ether; ethyl oleate; and poloxamers.

3. Therapeutic Agent

In the embodiments of the present invention that include therapeutic agents, the therapeutic agents suitable for use in the pharmaceutical compositions and methods of the present invention are not particularly limited, as the compositions are surprisingly capable of solubilizing and delivering a wide variety of therapeutic agents. The therapeutic agents can be hydrophilic, lipophilic, amphiphilic or hydrophobic, and can be solubilized in the carrier, e.g., the triglyceride, the surfactant(s), or both the triglyceride and the surfactant, or present in the diluent. Optionally, the therapeutic agent can be present in a first, solubilized amount, and a second, non-solubilized (suspended) amount. Such therapeutic agents can be any agents having therapeutic or other value when administered to an animal, particularly to a mammal, such as drugs, nutrients, and cosmetics (cosmeceuticals). It should be understood that while the invention is described with particular reference to its value in the form of aqueous dispersions, the invention is not so limited. Thus, drugs, nutrients or cosmetics which derive their therapeutic or other value from, for example, topical or transdermal administration, are still considered to be suitable for use in the present invention.

Specific non-limiting examples of therapeutic agents that can be used in the pharmaceutical compositions of the present invention include polysaccharide drugs, analgesics and anti-inflammatory agents, anthelmintics, anti-arrhythmic agents, anti-asthma agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents and immunosuppressants, anti-protozoal agents, anti-thyroid agents, anti-tussives, anxiolytic, sedatives, hypnotics and neuroleptics, β-Blockers, cardiac inotropic agents, corticosteroids, diuretics, anti-parkinsonian agents, gastrointestinal agents, histamine H,-receptor antagonists, keratolytics, lipid regulating agents, muscle relaxants, anti-anginal agents, nutritional agents, analgesics, sex hormones, stimulants, peptides, peptidomimetics, DNA, RNA, oligodeoxynucleotides, genetic material, proteins, oligonucleotides, and vaccines.

In one embodiment, the therapeutic agent is a nutritional agent.

In another embodiment, the therapeutic agent is a cosmeceutical agent.

In another embodiment, the therapeutic agent is a protein, peptide or oligonucleotide. In a particular aspect of this embodiment, the therapeutic agent is a protein, peptidomimetic, DNA, RNA, oligodeoxynucleotide, genetic material, peptide or oligonucleotide having a molecular weight of less than about 1000 g/mol.

In another embodiment, the therapeutic agent is hydrophobic. Hydrophobic therapeutic agents are compounds with little or no water solubility. Intrinsic water solubilities (i.e., water solubility of the unionized form) for hydrophobic therapeutic agents are less than about 1% by weight, and typically less than about 0.1% or 0.01% by weight. In a particular aspect of this embodiment, the therapeutic agent is a hydrophobic drug. In another particular aspect, the therapeutic agent is a hydrophobic drug having a molecular weight of less than about 1000 g/mol.

In another embodiment, the therapeutic agent is hydrophilic. Amphiphilic therapeutic agents are included within the class of hydrophilic therapeutic agents. Apparent water solubilities for hydrophilic therapeutic agents generally have an aqueous solubility greater than about 100 µg/ml. Such drugs include polysaccharides and other macromolecular drugs such as peptides, proteins, peptidomimetics, cytokines, nucleotides, nucleosides, genetic materials, toxoids, serum vaccines, etc. Generally, the hydrophilic drug is a polysaccharide drug, e.g., a disaccharide, oligosaccharide, or longer chain saccharide polymer that is suitable for administration to a human being. Examples of polysaccharide drugs include, without limitation, glucosamine, glycosaminoglycans, dextran, xylan, pentasaccharide, polygalacturonic acid, polymannuronic acid, chitin, pharmaceutically acceptable salts, esters or other derivatives thereof, and combinations of any of the foregoing. That is, a single polysaccharide drug may be administered, or two or more polysaccharide drugs may be administered in combination. The polysaccharide drugs may also be fragments of naturally occurring or synthetic polysaccharides.

Preferred polysaccharide drugs are glycosaminoglycans selected from heparin, heparan, chondroitin, dermatan, hyaluronic acid and pharmaceutically acceptable salts and esters thereof. More preferred polysaccharide drugs for administration using the present dosage forms and delivery systems are heparin, low molecular weight heparin, heparan, heparin and heparan salts formed with metallic cations (e.g., sodium, calcium or magnesium, preferably sodium) or organic bases (e.g., diethylamine, triethylamine, triethanolamine, etc.), heparin and heparan esters, heparin and heparan fatty acid conjugates, heparin and heparan bile acid conjugates, heparin sulfate, and heparan sulfate. For convenience, the aforementioned more preferred polysaccharide drugs are collectively referred to herein as "heparin." The particularly preferred drug herein is low molecular weight heparin, i.e., a heparin fragment generally having a weight average molecular weight in the range of 1000 to 10,000 D. Examples of low molecular weight heparin fragments include, but are not limited to, enoxaparin, dalteparin, danaproid, gammaparin, nadroparin, ardeparin, tinzaparin, certoparin and reviparin.

In another embodiment, the therapeutic agent is one that is commonly used in the prevention of blood coagulation or treatment of thrombosis. It is known that the process for blood coagulation involves numerous and complicated enzymatic reactions. In the final steps in this "cascade" of reactions, prothrombin is converted into thrombin. Thrombin, in turn, activates platelets and converts fibrinogen into fibrin, which is then converted into a higher molecular substance by polymerization and is further cross-linked by the action of activated blood factor XIII to form an insoluble blood clot. Accordingly, thrombin plays an important role in blood coagulation process. Thrombin also activates blood factors V and VIII, which, in turn, accelerate blood coagulation by a feed-back mechanism. Thus, there continues to be a need for compositions and dosage regimens that include thrombin inhibitors and other anticoagulant agents, given their specific and important biological activity. The compositions described herein may include thrombin inhibitors and/or other anticoagulant agents. By extension, the compositions containing such therapeutic agents are suitable for treating, e.g., preventing or curing, diseases related to inappropriate coagulation or thrombosis.

Thrombin inhibitors and other anticoagulant agents are particularly suitable for treating individuals suffering from heart diseases, lung diseases, and/or blood vessel diseases. Some nonlimiting examples of specific indications for which these therapeutic agents are useful include: post surgery thromboembolic and vascular disorder; thrombophilia; venous thromboembolism; severe Raynaud's phenomenon; deep vein thrombosis; pulmonary embolism; proximal venous thrombosis; excessive clotting; inflammation; arterial thrombosis; atherosclerosis; acute coronary syndromes, e.g., unstable angina or non-Q-wave myocardial infarction (MI); atrial fibrillation; valvular heart disease; rheumatic mitral valve disease; and dilated cardiomyopathy. An additional indication involves lowering the propensity for blood clots when blood comes into contact with implanted devices such as stents, prosthetic heart valves, and biprosthetic valves.

It will be recognized that the compositions and methods described herein may include a single therapeutic agent or a combination of two or more therapeutic agents. Such combinations provide improved patient compliance and/or a superior safety and efficacy profile when compared to the individual administration of single therapeutic agents. Although conventional doses of each therapeutic agent in the combination may be used, the combination may allow for dose modification, either higher or lower, given the improved patient compliance or superior safety and efficacy profile. Such modifications to the dose are based upon the overall therapeutic benefit to the patient, which can be evaluated by one of ordinary skill in the art using routine methodology. For example, lower doses of many therapeutic agents can still provide significant therapeutic benefits while decreasing potential side effects.

Preferred combinations include: LMW heparin with one or more anticoagulants, e.g., warfarin sodium, dipyridamole, or a combination thereof; LMW heparin with one or more platelet inhibitors, e.g., aspirin, hirudin, cilostazol, ticlodipine, clopidrogel, abciximab, eptifitabide, bivalirudin, or combination thereof; LMW heparin with a one or more fibrinolytic agents, e.g., unfractionated heparin, r-tPA, or combination thereof. The additional therapeutic agent can be provided in the same composition or dosage form with the polysaccharide drug, particularly LMW heparin. The additional therapeutic agent can also be provided in a separate composition or dosage form from the polysaccharide drug.

Some examples of therapeutic agents that can be administered alone or in conjunction with a low molecular weight heparin are listed below.

Platelet inhibitors:

Platelet inhibitors are also referred to as "platelet aggregation inhibitors," "platelet antiaggregants," "antiplatelet agents," "platelet antagonists" or "platelet aggregation inhibitors." Platelet inhibitors generally relate to drugs or agents that antagonize or impair a mechanism leading to blood platelet aggregation, whether during the phases of activation and shape change or following the dense-granule release reaction and stimulation of the prostaglandin-thromboxane system. Platelet inhibitors are used primarily to treat and prevent arterial thrombosis. Platelet inhibitors include salicylates, adenosine diphosphate (ADP) inhibitors, Glycoprotein IIb/IIIa antagonists, platelet derived growth factor, indirect thrombin inhibitors, cAMP-phosphodiesterase inhibitors, and anti-inflammatory agents.

Salicylates include, without limitation, acetylsalicylic acid ("ASA," commonly known as aspirin), choline salicylate, magnesium salicylate, sodium salicylate, and salicylate derivatives. Aspirin inhibits platelet aggregation by irreversibly acetylating the cyclo-oxygenase enzyme and reducing the production of thromboxane A2, which acts as a potent vasoconstrictor and platelet-aggregating substance.

ADP inhibitors include, without limitation, ticlopidine (commercially available under the tradename TICLID® from Hoffmann-LaRoche Inc., Nutley, N.J.) and clopidogrel (commercially available under the tradename PLAVIX® from Bristol-Myers Squibb Co., Princeton, N.J.). ADP inhibitors are thienopyridine derivatives that appear to inhibit ADP-induced platelet aggregation. There is also evidence that ticlopidine inhibits ADP-induced exposure of the fibrinogen binding site, the glycoprotein IIb/IIIa receptor complex on activated platelets.

Glycoprotein IIb/IIIa antagonists include, without limitation, glycoprotein IIb/IIIa receptor antibodies and glycoprotein IIb/IIIa inhibitors. Glycoprotein IIb/IIIa receptor antibodies are antibodies that are raised against the platelet glycoprotein IIb/IIIa receptor and. The antibody abciximab (commercially available under the tradename REOPRO® from Eli Lilly and Co., Indianapolis, Ind.) has been shown to be beneficial in patients with unstable angina and in patients undergoing angioplasty. Other immunoglobulins for platelet inhibition include $Rh_0$ (D) immune human globulin, also referred to as "anti-D gammaglobulin," "anti-D ($Rh_0$) immunoglobulin," "anti-Rh immunoglobulin," "anti-$Rh_0$ (D)," "D ($Rh_0$) immune globulin," "RhD immune globulin," "Rh immune globulin," "Rh-IG," and "$Rh_0$ (D) immune human globulin."

The glycoprotein IIb/IIIa inhibitor eptifibatide (commercially available under the tradename INTEGRELIN® from Schering-Plough Corp., Kenilworth, N.J.) is a cyclic peptide competitive inhibitor of the glycoprotein IIb/IIIa receptor and is beneficial to patients undergoing angioplasty and in patients with unstable angina. In addition, tirofiban (commercially available under the tradename AGGRASTAT® from Merck & Co., Whitehouse Station, N.J.) a small non-peptide receptor inhibitor, has also been approved for use in patients with unstable angina.

An example of an inhibitor of platelet-derived growth factor is trapadil (commercially available under the tradename ROCORNAL® from Mochida Pharmaceuticals Co., Tokyo, Japan).

Thrombin inhibitors include, without limitation, hirudin and hirulog, which bind at two specific sites on thrombin, thereby inhibiting the formation of both clot-bound and circulating thrombin. Other selective thrombin inhibitors known in the art may also be used.

cAMP-Phosphodiesterase inhibitors that have antiplatelet properties include, without limitation, cilostazol (commercially available under the tradename PLETAL® from Otsuka America Pharmaceutical, Inc., Rockville, Md.) and pentoxifylline (commercially available under the tradename TRENTAL® from Hoechst Marion Roussel, Inc., Kansas City, Mo.). Cilostazol, in particular, has a demonstrated benefit in increasing pain-free walking distance and improving claudication symptoms in patients suffering from peripheral arterial disease.

Anti-inflammatory agents having anticoagulant effects on platelets include, for example, non steroidal anti-inflammatory agents such as diclofenac, diflunisal, etodolac, fenoprofen, floctafenine, flurbiprofen, ibuprofen, indomethacin, ketoprofen, meclofenamate, mefenamic acid, meloxicam, nabumetone, naproxen, oxaprozin, phenylbutazone, piroxicam, sulindac, tenoxicam, tiaprofenic acid, tolmetin and ketorolac.

Cyclooxygenase inhibitors include, without limitation, parecoxib, celcoxib, rofecoxib and valdecoxib.

Anticoagulants:

Anticoagulants are agents that prevent blood clotting. Suitable anticoagulants include naturally occurring anticoagulants found in the blood as well as semi-synthetic and synthetic anticoagulants. Specific anticoagulants include, without limitation: warfarin (commercially available under the tradename COUMADIN® from DuPont Pharmaceuticals Co., Wilmington, Del.) which prevents the modification of vitamin K dependent coagulation factors (II, VII, IX, and X); dicoumarol; acenocoumarol; anisindione; dipyridamole (commercially available under the tradename PERSANTINE® from Boehringer Ingelheim Pharmaceuticals, Inc., Ridgefield, Conn.); purified antithrombin III (ATIII); recombinant peptide/hirudin such as lepirudin (commercially available under the tradename REFLUDAN® from Aventis Pharmaceuticals Inc., Bridgewater, N.J.); bivalirudin; danaparoid (commercially available under the tradename ORGARAN® from Organon Inc., West Orange, N.J.); ancrod; argatroban, a small molecule derived from L-arginine; H376/95; tissue factor pathway inhibitors; nematode anticoagulant peptide c2; activated protein C; pentasaccharides such as (Org30540/SR90107A); DX-9065a; and RGD peptides such as fibronectin, vitronectin, osteopontin, and thrombospontin, all of which contain the tripeptide sequence RGD (arginine-glycine-aspartic acid), a sequence generally necessary for interaction with cell surface receptors.

Fibrinolytic Agents:

Fibrinolytic agents also referred to as antithrombotic agents or thrombolytic agents include fibrinolysin, i.e., plasmin, or agents that convert plasminogen to fibrinolysin in addition to agents that induce clot lysis. Such agents include, without limitation, unfractionated heparin, streptokinase, urokinase, and recombinant tissue plasminogen activator (r-tPA), tenecteplase and alteplase.

The active agent in the present dosage forms may be an integral part of the composition, or it may be present in a coating on the dosage form, e.g., on a capsule, tablet, or caplet, or on each of a plurality of granules, beads, or pellets. In preferred embodiments, the active agent, e.g., low molecular weight heparin, is present as a part of the coating on the dosage form. Alternatively, the active agent is present as an integral part of the composition and is at least partially solubilized or suspended therein. The active agent may take any number of physical forms, e.g., it may be in crystalline, amorphous, nanosized, micronized or milled form.

Although the invention is not limited thereby, examples of therapeutic agents not previously listed that are suitable for use in the compositions and methods of the present invention include the following representative compounds, as well as their pharmaceutically acceptable salts, isomers, esters, ethers and other derivatives: abacavir, acarbose, acebutolol, acetazolamide, acetohexamide, acrivastine, acutretin, acyclovir, alatrofloxacin, albendazole, albuterol, aldlofenac, alendronate, allopurinol, aloxiprin, alprazolam, alprenolol, alprostadil, amantadine, amiloride, aminoglutethimide, amiodarone, amiodarone HCl, amitriptyline, amlodipine, amodiaquine, amoxapine, amoxapine, amphetamine, amphotericin, amprenavir, amrinone, amsacrine, amyl nitrate, amylobarbital, amylobarbitone, aspirin, astemizole, atenolol, atorvastatin, atovaquone, atropine, auranofin, azapropazone, azathioprine, azelastine, azithromycin, baclofen, barbital, barbitone, becaplermin, beclamide, beclomethasone, bendrofluazide, benethamine, benethamine penicillin, benezepril, benidipine, benorylate, bentazepam, benzhexol, benzhexol HCl, benznidazole, benzonatate, benztropine, bephenium hydroxynaphthoate, betamethasone, bezafibrate, bicalutamide, biperiden, bisacodyl, bisanthrene, bovine growth hormone, bromazepam, bromfenac, bromocriptine, bromocriptine mesylate, bromperidol, brompheniramine, brotizolam, budesonide, bumetanide, bupropion, busulphan, butenafine, butenafine HCl, butobarbital, butobarbitone, butoconazole, butoconazole nitrate, calcifediol, calciprotiene, calcitonin, calcitriol, cambendazole, camptothecan, camptothecin, candesartan, capecitabine, capsacin, capsaicin, captopril, carbamazepine, carbimazole, carbinoxamine, carbromal, carotenes, cefazolin, cefoxitin sodium, celecoxib, cephadrine, cephalexin, cerivistatin, cetrizine, chlopheniramine, chlophenisamine, chloproguanil, chlorambucil, chlordiazepoxide, chlormethiazole, chloroquine, chlorothiazide, chlorproguanil HCl, chlorpromazine, chlorpropamide, chlorprothiocene, chlorprothixene, chlorthalidone, cholecalciferol, cilostazol, cimetidine, cinnarizine, cinoxacin, ciprofloxacin, ciprofloxacin HCl, cisapride, citalopram, citrizine, clarithromycin, clemastine, clemastine fumarate, clemizole, clenbuterol, clinofibrate, clioquinol, clobazam, clofazimine, clofibrate, clomiphene, clomiphene citrate, clomipramine, clonazepam, clopidrogel, clotiazepam, clotrimazole, cloxacillin, clozapine, codeine, conjugated estrogens, cortisone acetate, cortisone acetate, cromalyn sodium, cromoglicate, cromolyn, cyclizine, cyclosporin, cyproheptadine, cyproheptadine HCl, dacarbazine, danazol, dantrolene, dantrolene sodium, darodipine, decoquinate, delavirdine, demeclocycline, desoxymethasone, dexamphetamine, dexchlopheniramine, dexfenfluramine, dextropropyoxyphene, diamorphine, diazepam, diazoxide, dichlorophen, diclofenac, dicloxacillin, dicoumarol, dicumarol, didanosine, diethylpropion, diflunisal, digitoxin, digoxin, dihydro epiandrosterone, dihydrocodeine, dihydroergotamine, dihydroergotamine mesylate, dihydrotachysterol, diiodohydroxyquinoline, dilitazem, dilitazem HCl, diloxanide furoate, dimenhydrinate, dinitolmide, diphenhydramine, diphenooxylate, diphenoxylate HCl, diphenylimidazole, diphenylpyrallin, dipyridamole, dirithromycin, disopyramide, divalproen, docusate, dolasetron, domperidone, donepezil, donepezil HCl, doxazosin, doxazosin HCl, doxycycline, dronabinol, droperidol, econazole, econazole nitrate, editronate, efavirenz, elanapril, ellipticine, enalapril, enkephalin, enoxacin, enoximone, enrofloxacin, epalrestate, eperisone, ephedrine, eposartan, eposartan losartan, ergocalciferol, ergotamine, ergotamine tartrate, erythromycin, erythropoietin, essential fatty acids, estramustine, ethacrynic acid, ethambutol, ethinamate, ethinyloestradiol, ethionamide, ethopropazine, ethopropazine HCl, ethotoin, etodolac, etoperidone, etoposide, etretinate, famcyclovir, famotidine, felbamate, felodipine, fenbendazole, fenbufen, fenfluramine, fenofibrate, fenolclopam, fenoldopam, fenoprofen, fenoprofen calcium, fentanyl, fexofenadine, finasteride, flecainide, flecainide acetate, fluconazole, flucortolone, flucytosine, fludrocortisone, fludrocortisone acetate, fluexetine HCl, flunanisone, flunarizine, flunarizine HCl, flunisolide, flunitrazepam, fluopromazine, fluoxetine, fluoxymisterone, flupenthixol decanoate, flupentixol, flupentixol decanoate, fluphenazine, fluphenazine decanoate, flurazepam, flurbiprofen, flurithromycin, fluticasone propionate, fluvastatin, foscarnet sodium, fosinopril, fosphenytoin, fosphenytoin sodium, frovatriptan, frusemide, fumagillin, furazolidone, furosemide, furzolidone, gabapentin, gancyclovir, gemfibrozil, gentamycin, glibenclamide, gliclazide, glipizide, glucagon, glybenclamide, glyburide, glyceryl trinitrate, glymepiride, glymepride, granisetron, granulocyte stimulating factor, grepafloxacin, griseofulvin, guanabenz, guanabenz acetate, halofantrine, halofantrine HCl, haloperidol, hydrocortisone, hyoscyamine, ibufenac, ibuprofen, imipenem, indinavir, indivir, indomethacin, insulin, interleukin-3, irbesartan, irinotecan, isosorbide dinitrate, isosorbide mononitrate, isotretinoin, isoxazole, isradipine, itraconazole, ivermectin, ketoconazole, ketoprofen, ketorolac, ketotifen, labetalol, lamivudine, lamotrigine, lanatoside C, lanosprazole, leflunomide, levofloxacin, levothyroxine, lisinopril, lomefloxacin, lomustine, loperamide, loratadine, lorazepam, lorefloxacin, lormetazepam, losartan, lovastatin, L-thryroxine, lysuride, lysuride maleate, maprotiline, maprotiline HCl, mazindol, mebendazole, meclofenamic acid, meclozine, meclozine HCl, medazepam, medigoxin, medroxyprogesterone acetate, mefenamic acid, mefloquine, mefloquine HCl, megesterol acetate, melonicam, melphalan, mepacrine, mepenzolate bromide, meprobamate, meptazinol, mercaptopurine, mesalazine, mesoridazine, mesoridiazine, mestranol, mesylate, metformin, methadone, methaqualone, methoin, methotrexate, methoxsalen, methsuximide, methylphenidate, methylphenobarbital, methylphenobarbitone, methylprednisolone, methyltestosterone, methysergide, methysergide maleate, metoclopramide, metolazone, metoprolol, metronidazole, mianserin, mianserin HCl, miconazole, midazolam, miglitol, minoxidil, mitomycins, mitotane, mitoxantrone, mofetil, molindone, montelukast, morphine, mortriptyline, moxifloxacin, moxifloxacin HCl, mycophenolate, nabumetone, nadolol, nalbuphine, nalidixic acid, naproxen, naratriptan, naratriptan HCl, natamycin, nedocromil sodium, nefazodone, nelfinavir, nerteporfin, neutontin, nevirapine, nicardipine, nicardipine HCl, nicotine, nicoumalone, nifedipine, nilutamide, nimesulide, nimodipine, nimorazole, nisoldipine, nitrazepam, nitro furantoin, nitrofurazone, nizatidine, non-essential fatty acids, norethisterone, norfloxacin, norgestrel, nortriptyline HCl, nystatin, oestradiol, ofloxacin, olanzapine, omeprazole, ondansetron, ondansetron HCL, oprelvekin, omidazole, oxacillin, oxamniquine, oxantel, oxantel embonate, oxaprozin, oxatomide, oxazepam, oxcarbazepine, oxfendazole, oxiconazole, oxprenolol, oxybutynin, oxyphenbutazone, oxyphencylcimine, oxyphencylcimine HCl, paclitaxel, pamidronate, paramethadione, paricalcitol, paroxetine, paroxetine HCl, penicillins, pentaerythritol tetranitrate, pentazocine, pentobarbital, pentobarbitone, pentoxifylline, perchloperazine, perfloxacin, pericyclovir, perphenazine, perphenazine pimozide, phenacemide, phenbenzamine, phenindione, pheniramine, phenobarbital, phenobarbitone, phenoxybenzamine HCl, phensuximide, phentermine, phenylalanine, phenylbutazone, phenytoin, physostigmine, phytonodione, pimozide, pindolol, pioglitazone, piroxicam, pizotifen, pizotifen maleate, pramipexol, pramipexole, pranlukast, pravastatin, praziquantel, prazosin, prazosin HCl, prednisolone, prednisone, pregabalin, primidone, probenecid, probucol, procarbazine, procarbazine HCl, prochlorperazine, progesterone, proguanil, proguanil HCl, propofol, propranolol, propylthiouracil, pseudoephedrine, pyrantel, pyrantel embonate, pyridostigmine, pyrimethamine, quetiapine, quinapril, quinidine, quinidine sulfate, quinine, quinine sulfate, rabeprazole, rabeprazole sodium, raloxifene, raloxifene HCl, ranitidine, ranitidine HCl, recombinant human growth hormone, refocoxib, remifentanil, repaglinide, reserpine, residronate, retinoids, ricobendazole, rifabutin, rifabutine, rifampicin, rifampin, rifapentine, rimantadine, rimexolone, risperodone, ritonavir, rizatriptan, rizatriptan benzoate, robinirole HCl, ropinirole, rosiglitazone, roxatidine, roxithromycin, salbutamol, salmon calcitonin (sCT), saquinavir, selegiline, sertindole, sertraline, sertraline HCl, sibutramine, sibutramine HCl, sildenafil, sildenafil citrate, simvastatin, sirolimus, sodium cefazoline, somatostatin, sparfloxacin, spiramycins, spironolactone, stanozolol, stavudine, stavueline, stiboestrol, sulconazole, sulconazole nitrate, sulfabenzamide, sulfacetamide, sulfadiazine, sulfadoxine, sulfafurazole, sulfamerazine, sulfamethoxazole, sulfapyridine, sulfasalazine, sulindac, sulphabenzamide, sulphacetamide, sulphadiazine, sulphadoxine, sulphafurazole, sulphamerazine, sulphamethoxazole, sulphapyridine, sulphasalazine, sulphin-pyrazone, sulpiride, sulthiame, sumatriptan, sumatriptan succinate, tacrine, tacrolimus, tamoxifen, tamoxifen citrate, tamsulosin, tamsulosin HCl, targretin, tazarotene, telmisartan, temazepam, teniposide, terazosin, terazosin HCl, terbinafine HCl, terbutaline, terbutaline sulfate, terconazole, terenadine, terfenadine, testolactone, testosterone, tetracycline, tetrahydrocannabinol, tetramisole, thiabendazole, thioguanine, thioridazine, tiagabine, tiagabine HCl, tibolone, ticlidopine, ticlopidine, tiludronate, timolol, tinidazole, tioconazole, tirofibran, tizanidine, tizanidine HCl, tolazamide, tolbutamide, tolcapone, tolmetin, tolterodine, topiramate, topotecan, topotecan HCl, toremifene, toremifene citrate, tramadol, trazodone, trazodone HCl, tretinoin, triamcinolone, triamterene, triazolam, trifluoperazine, trimethoprim, trimipramine, trimipramine maleate, troglitazone, tromethamine, tropicamide, trovafloxacin, tumor necrosisi factor, undecenoic acid, ursodeoxycholic acid, valacylcovir, valproic acid, valsartan, vancomycin, vasopressin, venlafaxine HCl, verteporfin, vigabatrin, vinblastine, vincristine, vinorelbine, vitamin A, vitamin $B_2$, vitamin D, vitamin E and vitamin K, vitamin $K_5$, vitamin $K_6$, vitamin $K_7$, vitamin K-S (II), zafirlukast, zileuton, zolmitriptan, zolpidem, and zopiclone.

Oil-soluble vitamins, e.g., vitamin E or compounds having vitamin E activity, are particularly preferred components of the compositions and dosage forms described herein. Examples of compounds having vitamin E activity include, but are not limited to, α-tocopherol, β-tocopherol, γ-tocopherol, δ-tocopherol, α-tocotrienol, β-tocotrienol, γ-tocotrienol, δ-tocotrienol, α-tocopherol acetate, β-tocopherol acetate, γ-tocopherol acetate, δ-tocopherol acetate, α-tocotrienol acetate, β-tocotrienol acetate, γ-tocotrienol acetate, δ-tocotrienol acetate, α-tocopherol succinate, β-tocopherol succinate, γ-tocopherol succinate, δ-tocopherol succinate, α-tocotrienol succinate, β-tocotrienol succinate, γ-tocotrienol succinate, δ-tocotrienol succinate, and mixtures thereof.

However, it should be noted that oil-soluble vitamins, particularly vitamin E and compounds having vitamin E activity, e.g., antioxidant activity, may also serve as a component of the carrier for improving the delivery of one or more therapeutic agents in the present compositions. Oil-soluble vitamins, particularly vitamin E and compounds having vitamin E activity, may improve the solubilization of other therapeutic agents in the composition and/or in an aqueous dispersion of the composition when placed in an aqueous medium. Furthermore, the stability of the therapeutic agent(s) in the composition and/or the stability of the composition as a whole may be enhanced when oil-soluble vitamins are present in the formulation. Additionally, the extent and/or Aconsistency of absorption of the therapeutic agent(s) may be improved in the presence of the oil-soluble vitamin, particularly vitamin E and compounds having vitamin E activity, due to improved solubilization of the therapeutic agent and/or improved permeability of the therapeutic agent across an absorption barrier, e.g. the mucosal membrane at the site of absorption. It should also be noted that the oil-soluble vitamins may be simply regarded as part of the carrier, rather than as therapeutic agents, if another therapeutic agent is present in the pharmaceutical composition (and intended for a therapeutic purpose unrelated to any therapeutic activity of the oil-soluble vitamin).

It may be desirable to include one or more additional active agents in the dosage forms herein. A wide range of additional active agents may be co-administered with the hydrophilic drug, including both hydrophilic and lipophilic active agents, particularly although not necessarily agents that potentiate certain effects of the hydrophilic drug, or vice versa. For example, co-administration with aspirin would be desirable to treat unstable angina, and co-administration with warfarin would be indicated for prophylaxis of deep-vein thrombosis.

Of course, salts, metabolic precursors, derivatives and mixtures of any of the therapeutic agents listed herein may also be used where desired.

4. Concentrations

The components of the pharmaceutical compositions of the present invention in amounts such that upon dilution with an aqueous medium, the composition forms a clear, aqueous dispersion. The determining concentrations of components to form clear aqueous dispersions are the concentrations of triglyceride and surfactants, with the amount of the therapeutic agent, if present, being chosen as described below. The relative amounts of triglycerides and surfactants are readily determined by observing the properties of the resultant dispersion; i.e., when the relative amounts of these components are within a suitable range, the resultant aqueous dispersion is optically clear. When the relative amounts are outside the suitable range, the resulting dispersion is visibly "cloudy," resembling a conventional emulsion or multiple-phase system. Although a visibly cloudy solution may be potentially useful for some applications, such a system would suffer from many of the same disadvantages as conventional prior art formulations, as described above.

The aqueous medium can comprise body fluids naturally occurring in the subject to whom the pharmaceutical compositions are administered. Such naturally occurring fluids can be the fluids occurring or produced in the oral cavity, nasal cavity, respiratory system, digestive system, for example, gastric juice, intestinal fluid, saliva, and lung fluid. The aqueous medium can also be fluids simulating such naturally occurring body fluids, for example, simulated gastric fluid and simulated intestinal fluid in absence or presence of variable amount of naturally occurring, semi-synthetic, or synthetic surface active materials. Typical surface active materials include proteins such as pepsin and pancreatin (which also possess enzymatic activity), bile acids, bile salts, phospholipids such as lecithins and lyso-lecithins and synthetic surfactant such as Tweens, sodium lauryl sulfate, etc. The concentration of such materials present in the simulated fluids can be in the range of about 0.01 wt. % to about 10 wt. %, most typically in the range of about 0.01 wt. % to about 1 wt. %. Occasionally, other organic materials such glycerol, alcohol, and polymers such as PEG and PVP can be incorporated in the simulated fluids to adjust properties such as viscosity, osmolarity, and dielectric constant; such materials can also serve as solubilizing agents.

A convenient method of determining the appropriate relative concentrations for any particular triglyceride is as follows. A convenient working amount of a hydrophilic surfactant is provided, and a known amount of the triglyceride is added. The mixture is stirred, with the aid of gentle heating if desired, then is diluted with purified water to prepare an aqueous dispersion. Any dilution amount can be chosen, but convenient dilutions are those within the range expected in vivo, about a 10 to 250-fold dilution. In the Examples herein, a convenient dilution of 100-fold was chosen. The aqueous dispersion is then assessed qualitatively for optical clarity. The procedure can be repeated with incremental variations in the relative amount of triglyceride added, to determine the maximum relative amount of triglyceride that can be present to form a clear aqueous dispersion with a given hydrophilic surfactant, i.e., when the relative amount of triglyceride is too great, a hazy or cloudy dispersion is formed.

The amount of triglyceride that can be solubilized in a clear aqueous dispersion is increased by repeating the above procedure, but substituting a second hydrophilic surfactant, or a hydrophobic surfactant, for part of the originally-used hydrophilic surfactant, thus keeping the total surfactant concentration constant. Of course, this procedure is merely exemplary, and the amounts of the components can be chosen using other methods, as desired.

It has been surprisingly found that mixtures of surfactants including two surfactants can solubilize a greater relative amount of triglyceride than a single surfactant. Similarly, mixtures of surfactants including a hydrophilic surfactant and a hydrophobic surfactant can solubilize a greater relative amount of triglyceride than either surfactant by itself. It is particularly surprising that when the surfactant mixture includes a hydrophilic surfactant and a hydrophobic surfactant, the solubility of the triglyceride is greater than, for example, in the hydrophilic surfactant itself. Furthermore, a greater amount of the hydrophobic surfactant can be solubilized when a triglyceride is present for a given amount of a hydrophilic surfactant. Thus, contrary to conventional knowledge in the art, the total amount of water-insoluble component (triglyceride plus hydrophobic surfactant) exceeds the amount of hydrophobic surfactant or triglyceride that can be solubilized by the same amount of hydrophilic surfactant. This unexpected finding shows a surprising and non-intuitive relationship between the hydrophilic and hydrophobic components.

It should be emphasized that the optical clarity is determined in the diluted composition (the aqueous dispersion), and not in the pre-concentrate. Thus, for example, U.S. Pat. No. 4,719,239 shows optically clear compositions containing water, oil, and a 3:7 mixture of PEG-glycerol monooleate and caprylic-capric acid glycerol esters, but the compositions contain no more that about 75% by weight water, or a dilution of the pre-concentrate of no more than 3 to 1. Upon dilution with water in a ratio of more than about 3 to 1, the compositions of the cited reference phase-separate into multi-phase systems, as is shown, for example, in the phase diagram of FIG. 2 in the '239 patent. In contrast, the compositions of the present invention, when diluted to values typical of dilutions encountered in vivo, or when diluted in vivo upon administration to a patient, remain as clear aqueous dispersions. Thus, the clear aqueous dispersions of the present invention are formed upon dilution of about 10 to about 250-fold or more.

As an alternative to qualitative visual assessment of optical clarity, the optical clarity of the aqueous dispersion can be measured using standard quantitative techniques for turbidity assessment. One convenient procedure to measure turbidity is to measure the amount of light of a given wavelength transmitted by the solution, using, for example, a UV-visible spectrophotometer. Using this measure, optical clarity corresponds to high transmittance, since cloudier solutions will scatter more of the incident radiation, resulting in lower transmittance measurements. If this procedure is used, care should be taken to insure that the composition itself does not absorb light of the chosen wavelength, as any true absorbance necessarily reduces the amount of transmitted light and falsely increases the quantitative turbidity value. In the absence of chromophores at the chosen wavelength, suitable dispersions at a dilution of 100X should have an apparent absorbance of less than about 0.3, preferably less than about 0.2, and more preferably less than about 0.1.

Other methods of characterizing optical clarity, such as direct particle size measurement and other methods known in the art may also be used.

It should be emphasized that any or all of the available methods may be used to ensure that the resulting aqueous dispersions possess the requisite optical clarity. For convenience, however, the present inventors prefer to use the simple qualitative procedure; i.e., simple visible observation. However, in order to more fully illustrate the practice of the present invention, both qualitative observation and spectroscopic measures are used to assess the dispersion clarity in the Examples herein.

If present, the therapeutic agent is solubilized in the carrier, e.g., the triglyceride, the surfactant(s), or both the triglyceride and the surfactant(s). Alternatively, the therapeutic agent can be solubilized in the aqueous medium used to dilute the preconcentrate to form an aqueous dispersion. The maximum amount of therapeutic agent that can be solubilized is readily determined by simple mixing, as the presence of any non-solubilized therapeutic agent is apparent upon visual examination.

In one embodiment, the therapeutic agent is present in an amount up to the maximum amount that can be solubilized in the composition. In another embodiment, the therapeutic agent is present in a first amount that is solubilized, and a second amount that remains unsolubilized but dispersed. This may be desirable when, for example, a larger dose of the therapeutic agent is desired. Although not all of the therapeutic agent is solubilized, such a composition presents advantages over conventional compositions, since at least a portion of the therapeutic agent is present in the clear aqueous dispersion phase. Of course, in this embodiment, the optical clarity of the resultant aqueous dispersion is determined before the second non-solubilized amount of the therapeutic agent is added.

In some contexts, the compositions will be "substantially free of water." "Substantially free of water" as used herein is intended to mean that the composition or dosage form contains less than 20% water (v/v). More preferably, the composition or dosage form contains less than about 10% water and most preferably less than about 5% water. In turn, this means that any water present will not form a continuous aqueous phase.

Other considerations well known to those skilled in the art will further inform the choice of specific proportions of components, e.g., surfactants and triglycerides, of the compositions. These considerations include the degree of bioacceptability of the compounds, and the desired dosage of therapeutic agent to be provided. In some cases, the amount of triglyceride or therapeutic agent actually used in a pharmaceutical composition according to the present invention will be less than the maximum that can be solubilized, and it should be apparent that such compositions are also within the scope of the present invention.

5. Solubilizers

If desired, the pharmaceutical compositions of the present invention can optionally include additional compounds to enhance the solubility of the therapeutic agent or the triglyceride in the composition. Examples of such compounds, referred to as "solubilizers," include:

alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulosic polymers, cyclodextrins and cyclodextrin derivatives;

ethers of polyethylene glycols having an average molecular weight of about 200 to about 6000, such as tetrahydrofurfuryl alcohol PEG ether (glycofurol, available commercially from BASF under the trade name Tetraglycol) or methoxy PEG (Union Carbide);

amides, such as 2-pyrrolidone, 2-piperidone, &-caprolactam, N-alkylpyrrolidone, N-hydroxyalkylpyrrolidone, N-alkylpiperidone, N-alkylcaprolactam, dimethylacetamide, and polyvinylpyrrolidone;

esters, such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof;

and other solubilizers known in the art, such as dimethyl acetamide, dimethyl isosorbide (Arlasolve DMI (ICI)), N-methyl pyrrolidones (Pharnasolve (ISP)), monooctanoin, diethylene glycol monoethyl ether (available from Gattefosse under the trade name Transcutol), and water.

Mixtures of solubilizers are also within the scope of the invention. Except as indicated, these compounds are readily available from standard commercial sources.

Preferred solubilizers include triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-600, glycofurol, transcutol, propylene glycol, and dimethyl isosorbide. Particularly preferred solubilizers include sorbitol, glycerol, triacetin, ethyl alcohol, PEG-400, glycofuirol and propylene glycol.

The amount of solubilizer that can be included in compositions of the present invention is not particularly limited. Of course, when such compositions are ultimately administered to a patient, the amount of a given solubilizer is limited to a bioacceptable amount, which is readily determined by one of skill in the art. In some circumstances, it may be advantageous to include amounts of solubilizers far in excess of bioacceptable amounts, for example, to maximize the concentration of therapeutic agent, with excess solubilizer removed prior to providing the composition to a patient using conventional techniques, such as distillation or evaporation. Thus, if present, the solubilizer can be in a concentration of 50%, 100%, 200%, or up to about 400% by weight, based on the amount of surfactant. If desired, very small amounts of solubilizers may also be used, such as 25%, 10%, 5%, 1% or even less. Typically, the solubilizer will be present in an amount of about 1% to about 100%, more typically about 5% to about 25% by weight or about 10% to about 25% by weight.

6. Enzyme Inhibitors

When the therapeutic agent is subject to enzymatic degradation, the compositions can include an enzyme-inhibiting agent. Enzyme inhibiting agents are shown for example, in Bemskop-Schnurch, A., "The use of inhibitory agents to overcome enzymatic barrier to perorally administered therapeutic peptides and proteins", *J Controlled Release* 52, 1–16 (1998), the disclosure of which is incorporated herein by reference.

Generally, inhibitory agents can be divided into the following classes:

Inhibitors that are not based on amino acids, such as P-aminobenzamidine, FK-448, camostat mesylate, sodium glycocholate;

Amino acids and modified amino acids, such as aminoboronic acid derivatives and n-acetylcysteine;

Peptides and modified peptides, such as bacitracin, phosphinic acid dipeptide derivatives, pepstatin, antipain, leupeptin, chymostatin, elastatin, bestatin, hosphoramindon, puromycin, cytochalasin potatocarboxy peptidase inhibitor, and amastatin;

Polypeptide protese inhibitors, such as aprotinin (bovine pancreatic trypsin inhibitor), Bowman-Birk inhibitor and soybean trypsin inhibitor, chicken egg white trypsin inhibitor, chicken ovoinhibitor, and human pancreatic trypsin inhibitor.

Complexing agents, such as EDTA, EGTA, 1,10-phenanthroline and hydroxychinoline; and Mucoadhesive polymers and polymer-inhibitor conjugates, such as polyacrylate derivatives, chitosan, cellulosics, chitosan-EDTA, chitosan-EDTA-antipain, polyacrylic acid-bacitracin, carboxymethyl cellulose-pepstatin, polyacrylic acid-Bwoman-Birk inhibitor.

The choice and levels of the enzyme inhibitor are based on toxicity, specificity of the proteases and the potency of the inhibition. The inhibitor can be suspended or solubilized in the composition preconcentrate, or added to the aqueous diluent or as a beverage.

Without wishing to be bound by theory, it is believed that an inhibitor can function solely or in combination as:

a competitive inhibitor, by binding at the substrate binding site of the enzyme, thereby preventing the access to the substrate; examples of inhibitors believed to operate by this mechanism are antipain, elastatinal and the Bowman Birk inhibitor;

a non-competitive inhibitor which can be simultaneously bound to the enzyme site along with the substrate, as their binding sites are not identical; and/or a complexing agent due to loss in enzymatic activity caused by deprivation of essential metal ions out of the enzyme structure.

7. Other Additives

Other additives conventionally used in pharmaceutical compositions can be included, and these additives are well known in the art. Such additives include detackifiers, antifoaming agents, buffering agents, antioxidants, preservatives, chelating agents, viscomodulators, tonicifiers, flavorants, colorants odorants, opacifiers, suspending agents, binders, fillers, plasticizers, lubricants, and mixtures thereof. The amounts of such additives can be readily determined by one skilled in the art, according to the particular properties desired. Of course, it will be appreciated that the presence of one or more additives in the compositions, and in the ultimate dosage form, may result in a dispersion that is not clear, i.e., a dispersion having an absorbance of greater than about 0.3 at 400 nm.

8. Dosage Forms

The pharmaceutical compositions of the present invention can be formulated as a preconcentrate in a liquid, semi-solid, or solid form, or as an aqueous or organic diluted preconcentrate. In the diluted form, the diluent can be water, an aqueous medium, a buffer, an organic solvent, a beverage, a juice, or mixtures thereof. If desired, the diluent can include components soluble therein, such as a therapeutic agent, an enzyme inhibitor, solubilizers, additives, and the like.

The compositions can be processed according to conventional processes known to those skilled in the art, such as lyophilization, encapsulation, compression, melting, extrusion, drying, chilling, molding, spraying, coating, comminution, mixing, homogenization, sonication and granulation, to produce the desired dosage form.

The dosage form is not particularly limited. Thus, compositions of the present invention can be formulated as pills, capsules, caplets, tablets, granules, beads or powders. Granules, beads and powders can, of course, be further processed to form pills, capsules, caplets or tablets. When formulated as a capsule, the capsule can be a hard or soft gelatin capsule, a starch capsule, or a cellulosic capsule. Such dosage forms can further be coated with, for example, a seal coating or an enteric coating. The term "enteric coated capsule" as used herein means a capsule coated with a coating resistant to acid; i.e., an acid resistant enteric coating. Enteric coated compositions of this invention protect therapeutic peptides or proteins in a restricted area of drug liberation and absorption, and reduce or even exclude extensive dilution effects. Although solubilizers are typically used to enhance the solubility of a hydrophobic therapeutic agent, they may also render the compositions more suitable for encapsulation in hard or soft gelatin capsules. Thus, the use of a solubilizer such as those described above is particularly preferred in capsule dosage forms of the pharmaceutical compositions. If present, these solubilizers should be added in amounts sufficient to impart to the compositions the desired solubility enhancement or encapsulation properties.

Although formulations specifically suited to oral administration are presently preferred, the compositions of the present invention can also be formulated for topical, transdermal, buccal, ocular, pulmonary, vaginal, rectal, transmucosal or parenteral administration, as well as for oral administration. Thus, the dosage form can be a solution, suspension, emulsion, cream, ointment, lotion, suppository, spray, aerosol, paste, gel, drops, douche, ovule, wafer, troche, cachet, syrup, elixir, or other dosage form, as desired. If formulated as a suspension, the composition can further be processed in capsule form.

When formulated as a sprayable solution or dispersion, a dosage form of a multiparticulate carrier coated onto a substrate with the pharmaceutical compositions described herein can be used. The substrate can be a granule, a particle, or a bead, for example, and formed of a therapeutic agent or a pharmaceutically acceptable material. The multiparticulate carrier can be enteric coated with a pharmaceutically acceptable material as is well known to those skilled in the art.

Other additives may be included, such as are well known in the art, to impart the desired consistency and other properties to the formulation.

9. Specific Embodiments

In all of the embodiments described herein, the triglyceride and surfactants are present in amounts such that upon mixing with an aqueous medium, either in vitro or in vivo, a clear, aqueous dispersion is formed. This optical clarity in an aqueous dispersion defines the appropriate relative concentrations of the triglyceride and surfactant components, but does not restrict the dosage form of the compositions to an aqueous dispersion, nor does it limit the compositions of the invention to optically clear dosage forms. Thus, the appropriate concentrations of the triglyceride and surfactants are determined by the optical clarity of a dispersion formed by the composition preconcentrate and an aqueous medium in a dilution of about 10 to about 250-fold, as a preliminary matter. Once the appropriate concentrations are determined, the pharmaceutical compositions can be formulated as described in the preceding section, without regard to the optical clarity of the ultimate formulation. Of course, optically clear aqueous dispersions, and their preconcentrates, are preferred formulations. In one embodiment, the present invention relates to pharmaceutical compositions having a triglyceride and a carrier, the carrier including at least two surfactants, at least one of which is hydrophilic. The triglyceride and surfactants are present in amounts such that upon mixing with an aqueous medium, either in vitro or in vivo, the composition forms a clear aqueous dispersion. In a particular aspect of this embodiment, the composition can contain more triglyceride than can be solubilized in a clear aqueous dispersion having only one surfactant, the surfactant being hydrophilic. Thus, this embodiment provides a higher concentration of triglyceride than is achievable with a single hydrophilic surfactant, resulting in a reduced triglyceride to hydrophilic surfactant ratio and enhanced biocompatibility.

In another embodiment, the present invention relates to pharmaceutical compositions having a triglyceride and a carrier, the carrier including at least one hydrophilic surfactant and at least one hydrophobic surfactant. The triglyceride and surfactants are present in amounts such that upon mixing with an aqueous medium, either in vitro or in vivo, the composition forms a clear aqueous dispersion. In a particular aspect of this embodiment, the composition contains more triglyceride than can be solubilized in a clear aqueous dispersion having a hydrophilic surfactant but not having a hydrophobic surfactant.

In another embodiment, the triglyceride itself can have therapeutic value as, for example, a nutritional oil, or absorption-promoting value as, for example, a long-chain triglyceride (LCT) or a medium-chain triglyceride (MCT). Thus, in this embodiment, the present invention provides pharmaceutical compositions including a triglyceride having nutritional and/or absorption-promoting value, and a carrier. The carrier includes at least two surfactants, at least one of which is hydrophilic. Optionally, the carrier can include at least one hydrophilic surfactant and at least one hydrophobic surfactant. The triglyceride and surfactants are present in amounts such that upon dilution with an aqueous medium, either in vitro or in vivo, the composition forms a clear aqueous dispersion.

In another embodiment, the present invention relates to a pharmaceutical composition that includes a therapeutic agent, a triglyceride and a carrier. The carrier includes at least two surfactants, at least one of which is hydrophilic. Optionally, the carrier includes at least one hydrophilic surfactant and at least one hydrophobic surfactant. The triglyceride, and surfactants are present in amounts such that upon dilution with an aqueous medium, either in vitro or in vivo, the composition forms a clear aqueous dispersion. The therapeutic agent is present in two amounts, a first amount of the therapeutic agent solubilized in the clear aqueous dispersion, and a second amount of the therapeutic agent that remains non-solubilized but dispersed.

In another aspect, the present invention relates to triglyceride-containing pharmaceutical compositions as described in the preceding embodiments, which further include a therapeutic agent. In particular embodiments, the therapeutic agent is a hydrophobic drug or a hydrophilic drug. In other embodiments, the therapeutic agent is a nutritional agent. In still further embodiments, the therapeutic agent is a cosmeceutical agent.

10. Preparation of Pharmaceutical Compositions

A. Overview

The pharmaceutical compositions of the present invention can be prepared by conventional methods well known to those skilled in the art. Of course, the specific method of preparation will depend upon the ultimate dosage form. For dosage forms substantially free of water, i.e., when the composition is provided in a pre-concentrate form for later dispersion in vitro or in vivo in an aqueous system, the composition is prepared by simple mixing of the components to form a pre-concentrate. The mixing process can be aided by gentle heating, if desired. For compositions in the form of an aqueous dispersion, the pre-concentrate form is prepared, then the appropriate amount of an aqueous medium is added. Upon gentle mixing, a clear aqueous dispersion is formed. If any water-soluble enzyme inhibitors or additives are included, these may be added first as part of the pre-concentrate, or added later to the clear aqueous dispersion, as desired. The compositions can be prepared with or without a therapeutic agent, and a therapeutic agent may also be provided in the diluent, if desired.

As previously noted, in another embodiment, the present invention includes a multi-phase dispersion containing a therapeutic agent. In this embodiment, a pharmaceutical composition includes a triglyceride and a carrier, which forms a clear aqueous dispersion upon mixing with an aqueous medium, and an additional amount of non-solubilized therapeutic agent. Thus, the term "multi-phase" as used herein to describe these compositions of the present invention means a composition which when mixed with an aqueous medium forms a clear aqueous phase and a particulate dispersion phase. The carrier and triglycerides are as described above, and can include any of the surfactants, therapeutic agents, solubilizers and additives previously described. An additional amount of therapeutic agent is included in the composition. This additional amount is not solubilized by the carrier, and upon mixing with an aqueous system is present as a separate dispersion phase. The additional amount is optionally a milled, micronized, or precipitated form. Thus, upon dilution, the composition contains two phases: a clear aqueous dispersion of the triglyceride and surfactants containing a first, solubilized amount of the therapeutic agent, and a second, non-solubilized amount of the therapeutic agent dispersed therein. It should be emphasized that the resultant multi-phase dispersion will not have the optical clarity of a dispersion in which the therapeutic agent is fully solubilized, but will appear to be cloudy, due to the presence of the non-solubilized phase. Such a formulation may be useful, for example, when the desired dosage of a therapeutic agent exceeds that which can be solubilized in the carrier and/or triglyceride. The formulation may also contain additives, as described above.

One skilled in the art will appreciate that a therapeutic agent may have a greater solubility in the pre-concentrate composition than in the aqueous dispersion, so that meta-stable, supersaturated solutions having apparent optical clarity but containing a therapeutic agent in an amount in excess of its solubility in the aqueous dispersion can be formed. Such super-saturated solutions, whether characterized as clear aqueous dispersions (as initially formed) or as multi-phase solutions (as would be expected if the meta-stable state breaks down), are also within the scope of the present invention.

The multi-phase formulation can be prepared by the methods described above. A pre-concentrate is prepared by simple mixing of the components, with the aid of gentle heating, if desired. It is convenient to consider the therapeutic agent as divided into two portions, a first solubilizable portion that will be solubilized and contained within the clear aqueous dispersion upon dilution, and a second non-solubilizable portion that will remain non-solubilized. When the ultimate dosage form is non-aqueous, the first and second portions of the therapeutic agent are both included in the pre-concentrate mixture. When the ultimate dosage form is aqueous, the composition can be prepared in the same manner, and upon dilution in an aqueous system, the composition will form the two phases as described above, with the second non-solubilizable portion of the therapeutic agent dispersed or suspended in the aqueous system, and the first solubilizable portion of the therapeutic agent solubilized in the composition. Alternatively, when the ultimate dosage form is aqueous, the pre-concentrate can be prepared including only the first, solubilizable portion of the therapeutic agent. This pre-concentrate can then be diluted in an aqueous system to form a clear aqueous dispersion, to which is then added the second, non-solubilizable portion of the therapeutic agent to form a multi-phase aqueous composition.

B. Methods

In another embodiment, the present invention relates to methods of increasing the solubilization of a therapeutic agent in a composition, by providing the therapeutic agent in a composition of the present invention. The composition can be any of the compositions described herein, with or without a therapeutic agent. It is surprisingly found that by using the combinations of triglycerides and surfactants described herein, greater amounts of triglycerides can be solubilized, without resort to unacceptably high concentrations of hydrophilic surfactants.

In another embodiment, the present invention relates to methods of increasing the rate and/or extent of absorption of therapeutic agents by administering to a patient a pharmaceutical composition of the present invention. In this embodiment, the therapeutic agent can be present in the pharmaceutical composition pre-concentrate, in the diluent, or in a second pharmaceutical composition, such as a conventional commercial formulation, which is co-administered with a pharmaceutical composition of the present invention. For example, the delivery of therapeutic agents in conventional pharmaceutical compositions can be improved by co-administering a pharmaceutical composition of the present invention with a conventional composition.

Administration of the compositions and dosage forms described herein may be used to treat any disorder, condition or disease for which the particular therapeutic agent is generally indicated. Dosage regimens and daily dosage for a therapeutic agent can vary a great deal, as a number of factors are involved, including the particular derivative of the therapeutic agent, the age and general condition of the patient, the particular condition or disorder and its severity, and the like. Clearly, however, it is necessary that the dosage given be sufficient to provide the desired pharmacological activity in a patient's circulation.

For low molecular weight heparains or heparinoids, typical intravenous or subcutaneous dosages are on the order of about 700 to 20,000 IU/day, while typical dosages for unfractionated heparin administered by injection are on the order of 10,000 to 40,000 Units/day. Expected typical dosages for orally administered low molecular weight heparin using the dosage forms of the invention are on the order of about 700 to 400,000, preferably 2,500 to 100,000 IU/day, while expected typical dosages for orally administered unfractionated heparin using the dosage forms of the invention are on the order of about 2,500 to 800,000 Units/day. For the administration of heparin and heparinoids, the indication will typically be the treatment and prevention of thrombosis.

For other therapeutic agents, the dosages can be determined by one of ordinary skill in the art without undue experimentation. For example, suitable dosages for humans can be determined based on data derived from animal studies. In addition, suitable dosages may be determined by administering an estimated dose, noting the response, and adjusting the dose accordingly.

C. Characteristics of the Pharmaceutical Compositions

The pharmaceutical compositions or the aqueous dispersions formed upon dilution of the pharmaceutical compositions described herein will generally have the following characteristics:

Rapid formation: upon dilution with an aqueous medium, the composition forms a clear dispersion very rapidly; i.e., the clear dispersion appears to form instantaneously.

Optical clarity: the dispersions are essentially optically clear to the naked eye, and show no readily observable signs of heterogeneity, such as turbidity or cloudiness. More quantitatively, dispersions of the pharmaceutical compositions of the present invention have absorbances (400 nm) of less than about 0.3, and often less than about 0.1, at 100X dilution, as described more fully in the Examples herein. In the multi-phase embodiment of the compositions described herein, it should be appreciated that the optical clarity of the aqueous phase will be obscured by the dispersed particulate non-solubilized therapeutic agent.

Robustness to dilution: the dispersions are surprisingly stable to dilution in aqueous medium. The hydrophobic therapeutic agent remains solubilized for at least the period of time relevant for absorption.

As discussed above, conventional triglyceride-containing formulations suffer the disadvantage that bioabsorption of the therapeutic agents contained therein is dependent upon enzymatic degradation (lipolysis) of the triglyceride components. The solubilization of the triglyceride in an aqueous medium is usually limited if only a hydrophilic surfactant is used to disperse the triglyceride, as is conventional. Without a sufficiently high concentration of the hydrophilic surfactant, an emulsion or milky suspension of the triglyceride is formed, and the triglyceride is present in the form of relatively large oil droplets. In this case, the large size of the triglyceride particles impedes the transport and absorption of the triglyceride or therapeutic agent solubilized in the triglyceride or in the carrier. In addition, the large, thermodynamically unstable triglyceride particles could further impose a risk when the compositions are administered intravenously, by plugging the blood capillaries.

To achieve a high level of fully-solubilized triglyceride would require an amount of the hydrophilic surfactant exceeding that which would be bioacceptable. The pharmaceutical compositions of the present invention, however, solve these and other problems of the prior art by adding a third component, a hydrophobic surfactant or a second hydrophilic surfactant. The solubilization of the triglyceride in the aqueous system is thereby unexpectedly enhanced. Conversely, it is also true that solubilization of a hydrophobic surfactant or a second hydrophilic surfactant is unexpected enhanced based on the presence of the triglyceride in the formulation. Of course, the relative amounts of the hydrophobic surfactant or the second hydrophilic surfactant in the formulation will depend on the type of formulation that is desired, actual components used, nature of the therapeutic agent, and so forth. These and other factors are routinely considered by those of skill in the art in determining the amount of each component to be added to a formulation. In addition, a suitable amount of each component to form the desired formulations can be readily determined by routine experimentation.

It is also unexpectedly found that the total amount of solubilized water-insoluble components, the triglyceride and hydrophobic surfactant, can greatly exceed the amount of the hydrophobic surfactant alone that can be solubilized using the same amount of the hydrophilic surfactant.

In addition to forming a thermodynamically stable aqueous dispersion upon mixing with an aqueous medium, the present compositions may also form optically clear, meta-stable or supersaturated dispersions with respect to the therapeutic agent and/or the triglyceride/hydrophobic surfactant in an amount in excess of the equilibrium solubility of the aqueous dispersion. Super-saturated solutions, whether characterized as homogeneous, single-phase and clear aqueous dispersions (as initially formed), or as multi-phase solutions (as would be expected if the meta-stable state breaks down), are also within the scope of the present invention. It is particularly desirable, however, that a meta-stable or supersaturated composition containing the therapeutic agent, triglyceride, and/or the hydrophobic surfactant is formed in the aqueous dispersion for at least a period of time sufficient for the absorption of the therapeutic agent in vivo. A suitable time period will be known by one of ordinary skill in the art. Generally, up to about eight hours, more typically from about one to about four hours, upon forming the dispersion is a sufficient time period for absorption of the therapeutic agent in vivo.

The unique pharmaceutical compositions and methods of the present invention present a number of significant and unexpected advantages, including:

Increased safety: The present compositions and methods allow for increased levels of triglyceride relative to hydrophilic surfactants, thereby reducing the need for excessively large amounts of hydrophilic surfactant. Further, the triglyceride-containing compositions of the present invention present small particle sizes, thus avoiding the problems of large particle size in conventional triglyceride-containing formulations and the concomitant safety concerns in parenteral administration.

Efficient transport: The particle sizes in the aqueous dispersions of the present invention are much smaller than the larger particles characteristic of vesicular, emulsion or microemulsion phases. This reduced particle size enables more efficient drug transport through the intestinal aqueous boundary layer, and through the absorptive brush border membrane. More efficient transport to absorptive sites leads to improved and more consistent absorption of therapeutic agents.

Less-dependence on lipolysis: The lack of large particle-size triglyceride components provides pharmaceutical compositions less dependent upon lipolysis, and upon the many poorly characterized factors that affect the rate and extent of lipolysis, for effective presentation of a therapeutic agent to an absorptive site. Such factors include the presence of composition components that may inhibit lipolysis; patient conditions which limit production of lipase, such as pancreatic lipase secretory diseases; and dependence of lipolysis on stomach pH, endogenous calcium concentration, and presence of co-lipase or other digestion enzymes. The reduced lipolysis dependence further provides transport that is less prone to suffer from any lag time between administration and absorption caused by the lipolysis process, enabling a more rapid onset of therapeutic action and better bioperformance characteristics. In addition, pharmaceutical compositions of the present invention can make use of hydrophilic surfactants that might otherwise be avoided or limited due to their potential lipolysis inhibiting effects.

Non-dependence on bile and meal fat contents: Due to the higher solubilization potential over bile salt micelles, the present compositions are less dependent on endogenous bile and bile related patient disease states, and meal fat contents. These advantages overcome meal-dependent absorption problems caused by poor patient compliance with meal-dosage restrictions.

Superior solubilization: The triglyceride and surfactant combinations used in compositions of the present invention enable superior loading capacity over conventional formulations. Thus, for example, more therapeutic agent can be solubilized in the triglyceride and surfactant combinations described herein than would be possible with conventional formulations containing only surfactant alone. Stated differently, the presence of the triglyceride in the present combinations improves the loading of the therapeutic agent for any given surfactant level. In addition, the particular combination of surfactants used can be optimized for a specific therapeutic agent to more closely match the polarity distribution of the therapeutic agent, resulting in still further enhanced solubilization.

Superior loading/presentation of absorption enhancers: The triglyceride and surfactant combinations in the present compositions enhance the compositions' loading capacity with respect to absorption enhancers incorporated therein, and also provide for superior presentation of the enhancers at the absorption sites, relative to conventional formulations. Consequently, the invention also includes a method for increasing the loading capacity of a pharmaceutical composition by providing: a pharmaceutical composition comprised of (a) a carrier comprising a triglyceride and a first surfactant, and (b) a therapeutically effective amount of a polysaccharide drug; and adding an absorption-enhancing amount of a second surfactant to the pharmaceutical composition, the second surfactant comprising a hydrophobic surfactant, wherein the absorption-enhancing amount is effective to increase the loading capacity of the pharmaceutical composition. The formulations formed by the method form clear aqueous dispersions. The formed dispersions preferably have, for example, an average particle size of less than about 200 nm and an absorbance of less of less than about 0.3 at 400 nm.

Preferred absorption enhancers include, without limitation, those mentioned in the overviews provided by Muranishi (1990), "Absorption Enhancers," *Critical Reviews in Therapeutic Drug Carrier Systems* 7 (1):1–33; Aungst (2000), "Intestinal Permeation Enhancers," *J. Pharm. Sci.* 89(4):429–442 and Curatolo et al. "Safety Assessment of Intestinal Permeability Enhancers" in "Drug Absorption Enhancement" (ed.) Boer, Harwood Academic Publishers. Such absorption enhancers include, for example, fatty acids, e.g., as described in sections 2.1, 2.2, 2.3, 2.4, 2.6, 2.7, 2.11, 2.16 and 2.19 supra, monoglycerides e.g., as described in section 2.9 supra, lecithins, e.g., as described in section 2.18 supra, and bile acids, e.g., as described in section 2.19 supra.

Because the compositions of the present invention provide a clear aqueous dispersion upon mixing with an aqueous medium, they have the advantage of sufficiently solubilizing and effectively presenting any absorption enhancer present in the compositions in an absorption-enhancing form at the absorption site of the therapeutic agent. For example, chenodeoxycholic acid (CDCA) and ursodeoxycholic acid (UDCA) are known enhancers for promoting the oral absorption of macromolecules. CDCA and UDCA, particularly UDCA, is practically insoluble in water having a pH at about 7 and below. As a result, there is a high probability that these enhancers will exist in their insoluble forms in the stomach and duodenum, thereby limiting their absorption-enhancing activity in a conventional formulation. The compositions of the present invention, however, are advantageous in that the absorption enhancer remains solubilized in the aqueous environment of the stomach and/or intestines following oral administration of the composition.

As another example, glycerol monooleate, like other hydrophobic enhancers, is practically water insoluble. In the absence of sufficient dispersion and/or solubilization, glycerol monooleate compositions form a turbid and coarse emulsion of large oil droplets that have little absorption enhancement activity. However, the combination of triglyceride and surfactants of the present invention enables the solubilization of glycerol mono-oleate in a clear aqueous dispersion, thereby facilitating the absorption-enhancing ability of glycerol monooleate.

Faster dissolution and release: Due to the robustness of compositions of the present invention to dilution, the therapeutic agents remain solubilized and thus do not suffer problems of precipitation of the therapeutic agent in the time frame relevant for absorption. In addition, the therapeutic agent is presented in small particle carriers, and is not limited in dilution rate by entrapment in emulsion carriers. These factors avoid liabilities associated with the poor partitioning of lipid solubilized drug in to the aqueous phase, such as large emulsion droplet surface area, and high interfacial transfer resistance, and enable rapid completion of the critical partitioning step.

Consistent performance: Aqueous dispersions of the present invention are thermodynamically stable for the time period relevant for absorption, and can be more predictably reproduced, thereby limiting variability in bioavailability—a particularly important advantage for therapeutic agents with a narrow therapeutic index.

Efficient release: The compositions of the present invention are designed with components that help to keep the therapeutic agent or absorption promoter, such as a permeation enhancer, an enzyme inhibitor, etc., solubilized for transport to the absorption site, but readily available for absorption, thus providing a more efficient transport and release.

Less prone to gastric emptying delays: Unlike conventional triglyceride-containing formulations, the present compositions are less prone to gastric emptying delays, resulting in faster absorption. Further, the particles in dispersions of the present invention are less prone to unwanted retention in the gastrointestinal tract.

Small size: Because of the small particle size in aqueous dispersion, the pharmaceutical compositions of the present invention allow for faster transport of the therapeutic agent through the aqueous boundary layer. Thus, the triglyceride and surfactants of the carrier are present in amounts such that upon mixing with an aqueous medium in an aqueous medium to carrier ratio of about 100:1 by weight, the carrier forms an aqueous dispersion having an average particle size less than about 200 nm.

Improved delivery of the therapeutic agent: As discussed previously, the delivery of the therapeutic agent is improved with respect to the extent, rate, and/or consistency of the absorption of the therapeutic agent. The improved delivery is a result of improved loading and solubilization of the triglyceride, the surfactant, and/or the therapeutic agent in the present compositions and in the aqueous dispersions thereof, as indicated, for example, by the clarity of the aqueous dispersion. In one approach, the delivery of the therapeutic agent is enhanced as a result of an increased amount of the therapeutic agent in a readily absorbable form. Delivery of hydrophobic therapeutic agents, such as fenofibrate, progesterone, and cyclosporin, may be enhanced based on this approach.

In another approach, the delivery of the therapeutic agent can also be potentially enhanced by the improved permeability of the therapeutic agent across the absorption barrier, e.g., the mucosal membranes in the nasal cavity, in the oral cavity, in the gastrointestinal tract, in the lungs and elsewhere in the body. Improved permeability is a result of improved loading in the composition, improved solubilization in the aqueous dispersion of the composition at the site of absorption, and the hydrophobic surfactants, e.g. fatty acids, bile acids, and mono-, di-fatty acid esters of polyols such as propylene glycol, glycerol, and polyethylene glycol, which often have absorption-enhancer activity. Delivery of hydrophilic therapeutic agents, such as bisphosphonates, low molecular weight heparin, oligonucleotides, and insulin may exhibit enhanced delivery based on this approach.

These and other advantages of the present invention, as well as aspects of preferred embodiments, are illustrated more fully in the Examples that follow.

EXAMPLES

Example 1 Preparation of Compositions

A simple pre-concentrate is prepared as follows. Predetermined weighed amounts of the surfactants and triglyceride are stirred together to form a homogeneous mixture. For combinations that are poorly miscible, the mixture can be gently heated to aid in formation of the homogeneous mixture. If the composition is to include a therapeutic agent, the chosen therapeutic agent in a predetermined amount is added and stirred until solubilized. Optionally, solubilizers or additives are included by simple mixing.

To form an aqueous dispersion of the pre-concentrate, a predetermined amount of purified water, buffer solution, or aqueous simulated physiological solution, is added to the pre-concentrate, and the resultant mixture is stirred to form a clear, aqueous dispersion.

Example 2 Triglyceride Solubilization in Conventional Formulations

Conventional formulations of a triglyceride and a hydrophilic surfactant were prepared for comparison to compositions of the present invention. For each surfactant-triglyceride pair, multiple dispersions were prepared with differing amounts of the two components, to determine the maximum amount of the triglyceride that can be present while the composition still forms a clear dispersion upon a 100-fold dilution with distilled water. No therapeutic agent was included in these compositions, since it is believed that the presence of the therapeutic agent does not substantially affect the clear, aqueous nature of composition. For the same reason, these compositions were free of additional solubilizers and other additives. The optical clarity was determined by visual inspection and/or by UV absorption (at 400 nm). When UV absorption was used, compositions were considered to be clear when the absorption was less than about 0.2. Table 20 shows the maximum amount of triglyceride present in such binary mixtures forming clear aqueous dispersions. The numerical entries in the Table are in units of grams of triglyceride per 100 grams of hydrophilic surfactant.

TABLE 20

Binary Triglyceride-Surfactant Solubility

| Hydrophilic Surfactant Triglyceride | PEG-35 Castor Oil (Incrocas 35) | PEG-40H Castor-Oil (Cremophor RH-40) | PEG-6 Caprate/ Caprylate (Softigen 767) | PEG-60 Corn Oil (Crovol M-70) | PEG-45 Palm Kernel Oil (Crovol PK-70) | Polysorbate-20 (Tween 20) | Polysorbate 80 (Tween 80) |
|---|---|---|---|---|---|---|---|
| Corn Oil (Croda, Super Refined) | 10 | 25 | 3 | 5 | 8 | 2 | 10 |
| Soybean Oil (Croda, Super Refined) | 10 | 25 | 3 | 8 | 8 | 2 | 10 |
| Glyceryl Tricaprylate/Caprate (Captex 300) | 60 | 40 | 8 | 30 | 25 | 20 | 45 |
| Glyceryl Tricaprylate/Caprate (Captex 355) | 70 | 40 | 5 | 55 | 30 | 20 | 55 |
| Glyceryl Tricaprylate/Caprate/Laurate (Captex 350) | 70 | 60 | 5 | 55 | 25 | 10 | 50 |
| Glyceryl Tricaprylate/Caprate/Linoleate (Captex 810D) | 30 | 40 | 3 | 25 | 15 | 2 | 25 |

Example 3 Effect of Surfactant Combinations

The procedure of Example 2 was repeated for compositions containing PEG-40 hydrogenated castor oil (Cremophor RH 40) or polysorbate 80 (Tween 80) as the hydrophilic surfactant, but substituting a second hydrophilic surfactant (compositions number 6–7 and 14–16) or a hydrophobic surfactant (compositions number 4–5, 8–9, and 17–18) for part of the hydrophilic surfactant. The total amount of hydrophilic surfactant 10 was kept constant. The results are summarized in Table 21.

TABLE 21A

Effects of Surfactant Combinations on the Solubilization of Triglycerides

| | Composition in w/w ratio | | | | | | | | |
|---|---|---|---|---|---|---|---|---|---|
| | 1 | 2 | 3 | 4 | 5 | 6 | 7 | 8 | 9 |
| Corn Oil | 25 | 30 | 40 | 40 | 40 | 40 | 40 | 40 | 40 |
| Cremophor RH-40 | 100 | 100 | 100 | 77 | 71 | 67 | 57 | 62 | 57 |
| Peceol | — | — | — | 23 | 29 | — | — | — | — |
| Kessco PEG 400 MO | — | — | — | — | — | 33 | 43 | — | — |
| Crovol M-40 | — | — | — | — | — | — | — | 38 | 43 |
| Appearance of the Concentrate | Clear | Hazy | Hazy | Clear | Clear | Clear | Clear | Hazy | Hazy |
| Abs @ 400 nm of the 100× (w/v) Dilution in Deionized Water | 0.148 | 2.195 | 2.518 | 0.121 | 0.132 | 0.124 | 0.102 | 0.233 | 0.167 |

TABLE 21B

Effects of Surfactant Combinations on the Solubilization of Triglycerides

| | Composition in w/w ratio | | | | | | | | |
|---|---|---|---|---|---|---|---|---|---|
| | 10 | 11 | 12 | 13 | 14 | 15 | 16 | 17 | 18 |
| Corn Oil | 10 | 15 | 20 | 30 | 15 | 20 | 30 | 20 | 25 |
| Tween 80 | 100 | 100 | 100 | 100 | 67 | 67 | 67 | 67 | 67 |
| Kessco PEG 400 MO | — | — | — | — | 33 | 33 | 33 | — | — |
| Crovol M-40 | — | — | — | — | — | — | — | 33 | 33 |
| Appearance of the Concentrate | Clear | Clear | Hazy | Hazy | Clear | Clear | Clear | Clear | Clear |
| Abs @ 400 nm of the 100× (w/v) Dilution in Deionized Water | 0.002 | 1.314 | 1.613 | 1.654 | 0.041 | 0.019 | 0.194 | 0.057 | 0.158 |

The clear or hazy appearance noted in the Table is that of the pre-concentrate, not of the aqueous dispersion. The clarity of the aqueous dispersion is shown quantitatively by UV absorption of the 1000X dilution at 400 nm.

Comparing compositions 1–3, a binary corn oil-Cremophor RH-40 mixture having 25 grams of corn oil per 100 grams of the surfactant is optically clear, having an absorption of 0.148. However, upon a slight increase of the amount of corn oil to 30 grams, the dispersion becomes cloudy, with an absorbance of 2.195, indicating the formation of a conventional emulsion. Compositions 4–5 show the surprising result that when part of the hydrophilic Cremophor RH-40 is replaced by a hydrophobic surfactant (Peceol), keeping the total surfactant concentration constant, compositions having a much higher amount of triglyceride (40 grams) still form clear aqueous dispersions, with absorbances less than 0.2 and dramatically less than the comparable binary composition number 3. A similar result is shown in compositions 8–9 for a different hydrophobic surfactant, Crovol M-40. Likewise, when part of the hydrophilic surfactant is replaced by a second hydrophilic surfactant in compositions 6–7, it is surprisingly found that the amount of triglyceride solubilized is similarly increased.

The second part of the Table, Table 21B, shows a similar surprising result for a different hydrophilic surfactant, Tween 80. Simple binary corn oil-Tween 80 mixtures form clear aqueous dispersions with 10 grams of corn oil, but are cloudy and multi-phasic with 15 grams or more of the triglyceride. As the Table shows, substitution of part of the hydrophilic surfactant with a second hydrophilic surfactant or a hydrophobic surfactant dramatically increases the amount of triglyceride that can be solubilized.

Example 4 Effect of Surfactant Combinations

Example 3 was repeated, using different triglyceride-surfactant combinations. In particular, medium-chain triglycerides (MCTs) were used instead of corn oil, a long-chain triglyceride (LCT). The results are shown in the three-part Table 22.

TABLE 22A

Solubilization of MCTs

| | Composition in w/w ratio | | | | |
|---|---|---|---|---|---|
| | 19 | 20 | 21 | 22 | 23 |
| Pureco 76 | 33 | 50 | 80 | 50 | 80 |
| Cremophor RH-40 | 100 | 100 | 100 | 40 | 100 |
| Imwitor 988 | — | — | — | 60 | 100 |
| Ethanol | — | — | — | — | 33 |
| Appearance of the Concentrate | Clear | Clear | Hazy | Clear | Clear |
| Abs @ 400 nm of the 100× (w/v) Dilution in Deionized Water | 0.201 | 0.346 | 2.522 | 0.204 | 0.098 |

TABLE 22B

Solubilization of MCTs

| | Composition in w/w ratio | | | |
|---|---|---|---|---|
| | 24 | 25 | 26 | 27 |
| Captex 300 | 40 | 75 | 75 | 75 |
| Cremophor RH-40 | 100 | 100 | 50 | 100 |

TABLE 22B-continued

Solubilization of MCTs

| | Composition in w/w ratio | | | |
|---|---|---|---|---|
| | 24 | 25 | 26 | 27 |
| Imwitor 988 | — | — | 50 | 75 |
| Appearance of the Concentrate | Clear | Hazy | Clear | Clear |
| Abs @ 400 nm of the 100× (w/v) Dilution in Deionized Water | 0.180 | 0.557 | 2.208 | 0.078 |

TABLE 22C

Solubilization of MCTs

| | Composition in w/w ratio | | | | | |
|---|---|---|---|---|---|---|
| | 28 | 29 | 30 | 31 | 32 | 33 |
| Captex 300 | 20 | 25 | 33 | 30 | 40 | 40 |
| Tween 20 | 100 | 100 | 100 | 70 | 70 | 66 |
| Brij 30 | — | — | — | 30 | 30 | 34 |
| Appearance of the Concentrate | Clear | Hazy | Hazy | Clear | Clear | Clear |
| Abs @ 400 nm of the 100× (w/v) Dilution in Deionized Water | 0.078 | 1.192 | 2.536 | 0.017 | 0.234 | 0.103 |

Table 22 shows that the increased solubilization of the triglyceride is observed for MCTs as well as for LCTs, with a variety of surfactants. Table 22 additionally shows that the same effect is observed in the presence of increased amounts of surfactants (compositions 23 and 27) and solubilizers (composition 23).

Example 5 Characterization of Compositions

Various compositions were prepared and characterized by visual observation as well as by UV absorbance at 400 nm. Each composition was diluted 100-fold with distilled water. The results are shown in Table 23.

TABLE 23

Visual and Spectroscopic Characterization

| No. | Composition | | Visual Observation | Absorbance at 400 nm |
|---|---|---|---|---|
| 24 | Soybean Oil | 80 mg | Very clear solution | 0.014 |
| | Tween 20 | 200 mg | | |
| | Tween 80 | 800 mg | | |
| 25 | Captex 810D | 250 mg | Very clear solution | 0.030 |
| | Incrocas 35 | 500 mg | | |
| | Tween 80 | 500 mg | | |
| 26 | Captex 810D | 200 mg | Clear solution | 0.157 |
| | Incrocas 35 | 667 mg | | |
| | Myvacet 9-45 | 333 mg | | |
| 27 | Corn Oil | 250 mg | Clear solution | 0.085 |
| | Cremophor RH-40 | 750 mg | | |
| | Peceol | 150 mg | | |
| | Propylene Glycol | 100 mg | | |
| 28 | Captex 355 | 200 mg | Clear solution | 0.212 |
| | Labrafil M2125CS | 300 mg | | |
| | Cremophor RH-40 | 500 mg | | |
| | Ethanol | 100 mg | | |
| 29 | Captex 355 | 150 mg | Clear solution | 0.141 |
| | Cremophor RH-40 | 600 mg | | |
| | Labrafil M2125CS | 250 mg | | |
| | Ethanol | 100 mg | | |
| 30 | Captex 355 | 300 mg | Clear solution, Slightly hazy | 0.241 |
| | Incrocas 35 | 500 mg | | |
| | Labrafil M2125CS | 200 mg | | |
| | Ethanol | 100 mg | | |
| 31 | Captex 355 | 250 mg | Clear solution | 0.076 |
| | Incrocas 35 | 600 mg | | |
| | Labrafil M2125CS | 150 mg | | |
| | Ethanol | 100 mg | | |
| 32 | Pureco 76 | 160 mg | Clear solution | 0.168 |
| | Cremophor RH-40 | 480 mg | | |
| | Labrafil M2125CS | 160 mg | | |
| | Ethanol | 150 mg | | |

Example 6 Comparative Example

Prior art formulations were prepared for comparison with the compositions of the present invention. As in Example 5, the compositions were diluted 100-fold with distilled water, and characterized by visual observation and by UV absorbance. The results are shown in Table 24.

TABLE 24

Compositions Not Forming Clear Aqueous Dispersions

| No. | Composition | | Visual Observation | Absorbance at 400 nm |
|---|---|---|---|---|
| 33 | Corn Oil | 400 mg | Milky suspension | 1.989 |
| | Cremophor RH-40 | 710 mg | | |
| | Crovol M-40 | 290 mg | | |
| 34 | Captex 300 | 300 mg | Milky suspension | 1.594 |
| | Tween 20 | 650 mg | | |
| | Imwitor 988 | 350 mg | | |
| 35 | Corn Oil | 400 mg | Milky suspension | 2.716 |
| | Cremophor RH-40 | 620 mg | | |
| | Labrafil M2125CS | 380 mg | | |
| 36 | Soybean Oil | 185 mg | Milky suspension | 2.595 |
| | Captex GTO | 275 mg | | |
| | Tween 80 | 275 mg | | |
| | Triacetin | 185 mg | | |
| 37 | Pureco 76 | 315 mg | Milky suspension | 2.912 |
| | Cremophor RH-40 | 225 mg | | |
| | Span 20 | 360 mg | | |
| 38 | Soybean Oil | 340 mg | Milky suspension | 2.566 |
| | Captex GTO | 280 mg | | |
| | Tween 80 | 280 mg | | |
| 39 | Pureco 76 | 330 mg | Milky suspension | 2.233 |
| | Labrasol | 120 mg | | |
| 40 | Corn Oil | 400 mg | Milky suspension | 2.249 |
| | Cremophor RH-40 | 570 mg | | |
| | Lauroglycol FCC | 430 mg | | |
| 41 | Soybean Oil | 160 mg | Milky suspension | 2.867 |
| | Tween 80 | 200 mg | | |
| | Imwitor 988 | 450 mg | | |
| | Ethanol | 150 mg | | |
| 42 | Corn Oil | 200 mg | Milky suspension | 1.547 |
| | Tween 80 | 570 mg | | |
| | Kessco PEG 400 MO | 430 mg | | |

As the Table shows, conventional formulations such as those disclosed in U.S. Pat. No. 5,645,856, form milky suspensions rather than the clear aqueous dispersions of the present invention.

Example 7 Formulations with Therapeutic Agents

Table 25 shows several formulations of compositions that can be prepared according to the present invention, using a variety of therapeutic agents.

TABLE 25

Formulations

| No. | Composition (g) | |
|---|---|---|
| 43 | Cremophor RH-40 | 0.75 |
| | Peceol | 0.25 |
| | Corn Oil NF | 0.40 |
| | Heparin sodium | 0.10 |
| 44 | Cremophor RH-40 | 0.57 |
| | Crovol M-40 | 0.43 |
| | Corn Oil NF | 0.40 |
| | Heparan | 0.15 |
| 45 | Cremophor RH-40 | 0.57 |
| | Kessco PEG 400 MO | 0.43 |
| | Soybean Oil NF | 0.40 |
| | Heparan sulfate | 0.30 |
| 46 | Tween 80 | 0.70 |
| | Tween 85 | 0.35 |
| | Miglyol 812 | 0.30 |
| | Hyaluronic acid | 0.10 |
| | PEG 400 | 0.25 |
| 47 | Cremophor RH-40 | 0.50 |
| | Imwitor 988 | 0.50 |
| | Captex 300 | 0.75 |
| | Dermatan | 0.20 |
| | Propylene Glycol | 0.15 |
| 48 | Tween 20 | 0.66 |
| | Brij 30 | 0.34 |
| | Captex 355 | 0.40 |
| | Chondroitin | 0.02 |
| 49 | Tween 80 | 0.67 |
| | Kessco PEG 400 MO | 0.33 |
| | Corn Oil | 0.30 |
| | Dalteparin sodium (a LMW heparin) | 0.25 |
| 50 | Crovol M-70 | 0.67 |
| | Crovol M-40 | 0.33 |
| | Captex 350 | 0.75 |
| | Nadroparin Ca (a LMW heparin) | 0.10 |
| | Ethanol | 0.15 |
| 51 | Cremophor RH40 | 0.45 |
| | Arlacel 186 | 0.32 |
| | Olive Oil | 0.23 |
| | Enoxaprin (a LMW heparin) | 0.04 |
| 52 | Incrocas 35 | 0.80 |
| | Arlacel 186 | 0.20 |
| | Miglyol 818 | 0.45 |
| | Dextran | 0.04 |
| | Water | 0.10 |
| 53 | Cremophor RH-40 | 0.62 |
| | Capmul MCM | 0.38 |
| | Miglyol 810 | 0.25 |
| | Heparin sodium | 0.03 |
| | Water | 0.10 |
| | PEG 400 | 0.05 |
| 54 | Gelucire 44/14 | 0.35 |
| | Monomul 90L-12 | 0.15 |
| | Kollidon 30 | 0.35 |
| | Fenofibrate | 0.15 |
| 55 | Cremophor RH-40 | 0.57 |
| | Crovol M-40 | 0.43 |
| | Corn Oil NF | 0.40 |
| | Rofecoxib | 0.15 |
| 56 | Cremophor RH-40 | 0.57 |
| | Kessco PEG 400 MO | 0.43 |
| | Soybean Oil NF | 0.40 |
| | Nabumetone | 0.30 |
| 57 | Tween 80 | 0.70 |
| | Tween 85 | 0.35 |
| | Miglyol 812 | 0.30 |
| | Paclitaxel | 0.10 |
| | PEG 400 | 0.25 |
| 58 | Cremophor RH-40 | 0.50 |
| | Imwitor 988 | 0.50 |
| | Captex 300 | 0.75 |
| | Cyclosporin A | 0.20 |
| | Propylene Glycol | 0.15 |
| 59 | Tween 20 | 0.66 |
| | Brij 30 | 0.34 |
| | Captex 355 | 0.40 |
| | Retinoic Acid | 0.02 |
| 60 | Tween 80 | 0.67 |
| | Kessco PEG 400 MO | 0.33 |
| | Corn Oil | 0.30 |
| | Terbinafine | 0.25 |
| 61 | Crovol M-70 | 0.67 |
| | Crovol M-40 | 0.33 |
| | Captex 350 | 0.75 |
| | Progesterone | 0.10 |
| | Ethanol | 0.15 |
| 62 | Labrasol | 0.30 |
| | Gelucire 44/14 | 0.70 |
| | Dronabinol | 0.02 |
| | Ethanol | 0.10 |
| 63 | Incrocas 35 | 0.80 |
| | Arlacel 186 | 0.20 |
| | Miglyol 818 | 0.45 |
| | Alendronate sodium | 0.04 |
| | Water | 0.10 |
| 64 | Ursodeoxycholic Acid | 0.15 |
| | Lutrol F68 | 0.45 |
| | Imwitor 928 | 0.20 |
| | Kollidon 30 | 0.20 |
| | Tinzaparin (a LMW heparin) | 0.10 |
| 65 | Vitamin E-TPGS | 0.40 |
| | Ursodeoxycholic Acid | 0.10 |
| | Maisine I-35 | 0.20 |
| | Kollidon 30 | 0.30 |
| 66 | Cremophor RH-40 | 0.62 |
| | Capmul MCM | 0.38 |
| | Miglyol 810 | 0.25 |
| | Heparin sodium | 0.03 |
| | Water | 0.10 |
| | PEG 400 | 0.05 |

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope. All patents, patent applications, patent publications and non-patent literature references mentioned herein are incorporated by reference in their entireties.

We claim:

1. A pharmaceutical composition comprising:
   (a) a carrier comprising a triglyceride and at least two surfactants, at least one of the surfactants being hydrophilic; and
   (b) a therapeutically effective amount of a polysaccharide drug, wherein the triglyceride and surfactants are present in amounts such that upon mixing with an aqueous medium in an aqueous medium to carrier ratio of about 100:1 by weight, the carrier forms a clear aqueous dispersion having an absorbance of less than about 0.3 at 400 nm.

2. The pharmaceutical composition of claim 1, wherein the triglyceride is selected from the group consisting of vegetable oils, fish oils, animal fats, hydrogenated vegetable oils, partially hydrogenated vegetable oils, synthetic triglycerides, modified triglycerides, fractionated triglycerides, and mixtures thereof.

3. The pharmaceutical composition of claim 1, wherein the triglyceride is selected from the group consisting of almond oil; babassu oil; borage oil; blackcurrant seed oil;

canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; soy oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; glyceryl tricaprylate/caprate/stearate; saturated polyglycolized glycerides; linoleic glycerides; caprylic/capric glycerides; modified triglycerides; fractionated triglycerides; and mixtures thereof.

4. The pharmaceutical composition of claim 1, wherein the triglyceride is selected from the group consisting of coconut oil; corn oil; olive oil; palm oil; peanut oil; safflower oil; sesame oil; soybean oil; hydrogenated castor oil; hydrogenated coconut oil; partially hydrogenated soybean oil; glyceryl tricaprate; glyceryl trilaurate; glyceryl trioleate; glyceryl trilinoleate; glyceryl tricaprylate/caprate; glyceryl tricaprylate/caprate/laurate; glyceryl tricaprylate/caprate/linoleate; glyceryl tricaprylate/caprate/stearate; saturated polyglycolized glycerides; linoleic glycerides; caprylic/capric glycerides; modified triglycerides; fractionated triglycerides; and mixtures thereof.

5. The pharmaceutical composition of claim 1, wherein the triglyceride is selected from the group consisting of a medium chain triglyceride, a long chain triglyceride, a modified triglyceride, a fractionated triglyceride, and mixtures thereof.

6. The pharmaceutical composition of claim 1, wherein the hydrophilic surfactant comprises at least one non-ionic hydrophilic surfactant having an HLB value greater than or equal to about 10.

7. The pharmaceutical composition of claim 1, wherein the hydrophilic surfactant comprises at least one ionic surfactant.

8. The pharmaceutical composition of claim 6, which further comprises at least one ionic surfactant.

9. The pharmaceutical composition of claim 6, wherein the non-ionic surfactant is selected from the group consisting of alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols; polyoxyethylene vegetable oils; polyoxyethylene hydrogenated vegetable oils; reaction mixtures of polyols and at least one member of the group consisting of fatty acids, glycerides, vegetable oils, hydrogenated vegetable oils, and sterols; sugar esters, sugar ethers; sucroglycerides; and mixtures thereof.

10. The pharmaceutical composition of claim 6, wherein the non-ionic hydrophilic surfactant is selected from the group consisting of polyoxyethylene alkylethers; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene vegetable oils; polyoxyethylene hydrogenated vegetable oils; reaction mixtures of polyols and at least one member of the group consisting of fatty acids, glycerides, vegetable oils, hydrogenated vegetable oils, and sterols; and mixtures thereof.

11. The pharmaceutical composition of claim 10, wherein the glyceride is selected from the group consisting of a monoglyceride, a diglyceride, a triglyceride, and mixtures thereof.

12. The pharmaceutical composition of claim 10, wherein the reaction mixture comprises the transesterification products of a polyol and at least one member of the group consisting of fatty acids, glycerides, vegetable oils, hydrogenated vegetable oils, and sterols.

13. The pharmaceutical composition of claim 11, wherein the polyol is selected from the group consisting of glycerol, ethylene glycol, polyethylene glycol, sorbitol, propylene glycol, pentaerythritol, a saccharide, and mixtures thereof.

14. The pharmaceutical composition of claim 6, wherein the hydrophilic surfactant is selected from the group consisting of PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, a poloxamer, and mixtures thereof.

15. The pharmaceutical composition of claim 6, wherein the hydrophilic surfactant is selected from the group consisting of PEG-20 laurate, PEG-20 oleate, PEG-35 castor oil, PEG-40 palm kernel oil, PEG-40 hydrogenated castor oil, PEG-60 corn oil, PEG-25 glyceryl trioleate, polyglyceryl-10 laurate, PEG-6 caprate/caprylate glycerides, PEG-8 caprate/caprylate glycerides, PEG-30 cholesterol, polysorbate 20, polysorbate 80, POE-9 lauryl ether, POE-23 lauryl ether, POE-10 oleyl ether, PEG-24 cholesterol, sucrose monostearate, sucrose monolaurate, a poloxamer, and mixtures thereof.

16. The pharmaceutical composition of claim 6, wherein the hydrophilic surfactant is selected from the group consisting of PEG-35 castor oil, PEG-40 hydrogenated castor oil, PEG-60 corn oil, PEG-25 glyceryl trioleate, PEG-6 caprate/caprylate glycerides, PEG-8 caprate/caprylate glycerides, polysorbate 20, polysorbate 80, tocopheryl PEG-1000 succinate, PEG-24 cholesterol, a poloxamer, and mixtures thereof.

17. The pharmaceutical composition of claim 7, wherein the ionic surfactant is selected from the group consisting of alkyl ammonium salts; bile salts; fusidic acid; fatty acid conjugates of amino acids, oligopeptides, and polypeptides; glyceride esters of amino acids, oligopeptides, and polypeptides; acyl lactylates; mono- and diacetylated tartaric acid esters of mono- and diglycerides; succinylated monoglycerides; citric acid esters of mono- and diglycerides; alginate salts; propylene glycol alginate; lecithins and hydrogenated lecithins; lysolecithin and hydrogenated lysolecithins; lysophospholipids; carnitine fatty acid ester salts; phospholipids; salts of alkylsulfates; salts of fatty acids; sodium docusate; and mixtures thereof.

18. The pharmaceutical composition of claim 7, wherein the ionic surfactant is selected from the group consisting of bile acids and; lecithins, lysolecithin, phospholipids, and lysophospholipids; carnitine fatty acid ester salts; salts of alkylsulfates; salts of fatty acids; sodium docusate; acyl lactylates; mono- and diacetylated tartaric acid esters of mono- and diglycerides; succinylated monoglycerides; citric acid esters of mono-, diglycerides; and mixtures thereof.

19. The pharmaceutical composition of claim 7, wherein the ionic surfactant is selected from the group consisting of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, taurodeoxycholate, chenodeoxycholate, glycodeoxycholate, glycochenodeoxycholate, taurochenodeoxycholate, ursodeoxycholate, lithocholate, tauroursodeoxycholate, glycoursodeoxycholate, cholylsarcosine, N-methyl taurocholate, caproate, caprylate, caprate, laurate, myristate, palmitate, oleate, ricinoleate, linoleate, linolenate, stearate, lauryl sulfate, tetraacetyl sulfate, docusate, lauroyl carnitine, palmitoyl carnitine, myristoyl carnitine, and salts and mixtures thereof.

20. The pharmaceutical composition of claim 7, wherein the ionic surfactant is selected from the group consisting of lecithin, lysolecithin, phosphatidylcholine, phosphatidylethanolamine, phosphatidylglycerol, lysophosphatidylcholine, PEG-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, chenodeoxycholate, lithocholate, ursodeoxycholate, taurodeoxycholate, glycodeoxycholate, cholylsarcosine, caproate, caprylate, caprate, laurate, oleate, lauryl sulfate, docusate, lauroyl carnitine, palmitoyl carnitine, myristoyl carnitine, and salts and mixtures thereof.

21. The pharmaceutical composition of claim 7, wherein the ionic surfactant is selected from the group consisting of lecithin, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, chenodeoxycholate, lithocholate, ursodeoxycholate, taurocholate, caprylate, caprate, oleate, lauryl sulfate, docusate, lauroyl carnitine, palmitoyl carnitine, myristoyl carnitine, and salts and mixtures thereof.

22. The pharmaceutical composition of claim 1, wherein the carrier comprises at least two hydrophilic surfactants.

23. The pharmaceutical composition of claim 1, wherein the carrier comprises at least one hydrophilic surfactant and at least one hydrophobic surfactant.

24. The pharmaceutical composition of claim 23 wherein the hydrophobic surfactant is a compound or mixture of compounds having an HLB value less than about 10.

25. The pharmaceutical composition of claim 24, wherein the hydrophobic surfactant is selected from the group consisting of alcohols; polyoxyethylene alkylethers; fatty acids; bile acids; glycerol fatty acid esters; acetylated glycerol fatty acid esters; lower alcohol fatty acids esters; polyethylene glycol fatty acids esters; polyethylene glycol glycerol fatty acid esters; polypropylene glycol fatty acid esters; polyoxyethylene glycerides; lactic acid esters of mono/diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sugar esters; sugar ethers; sucroglycerides; polyoxyethylene vegetable oils; polyoxyethylene hydrogenated vegetable oils; reaction mixtures of polyols and at least one member of the group consisting of fatty acids, glycerides, vegetable oils, hydrogenated vegetable oils, and sterols; and mixtures thereof.

26. The pharmaceutical composition of claim 24, wherein the hydrophobic surfactant is selected from the group consisting of fatty acids; bile acids; lower alcohol fatty acid esters; polyethylene glycol glycerol fatty acid esters; polypropylene glycol fatty acid esters; polyoxyethylene glycerides; glycerol fatty acid esters; acetylated glycerol fatty acid esters; lactic acid esters of mono/diglycerides; sorbitan fatty acid esters; polyoxyethylene sorbitan fatty acid esters; polyoxyethylene-polyoxypropylene block copolymers; polyoxyethylene vegetable oils; polyoxyethylene hydrogenated vegetable oils; reaction mixtures of polyols and at least one member of the group consisting of fatty acids, glycerides, vegetable oils, hydrogenated vegetable oils, and sterols; and mixtures thereof.

27. The pharmaceutical composition of claim 24, wherein the hydrophobic surfactant is selected from the group consisting of bile acids; lower alcohol fatty acids esters; polypropylene glycol fatty acid esters; propylene glycol fatty acid esters; glycerol fatty acid esters; acetylated glycerol fatty acid esters; lactic acid esters of mono/diglycerides; sorbitan fatty acid esters; polyoxyethylene vegetable oils; and mixtures thereof.

28. The pharmaceutical composition of claim 24, wherein the hydrophobic surfactant is selected from the group consisting of a glycerol fatty acid ester, an acetylated glycerol fatty acid ester, and mixtures thereof.

29. The pharmaceutical composition of claim 28, wherein the glycerol fatty acid ester is selected from the group consisting of a monoglyceride, diglyceride, and mixtures thereof.

30. The pharmaceutical composition of claim 29, wherein the fatty acid of the glycerol fatty acid ester is a $C_6$ to $C_{22}$ fatty acid or a mixture thereof.

31. The pharmaceutical composition of claim 24, wherein the hydrophobic surfactant is a reaction mixture of a polyol and at least one member of the group consisting of fatty acids, glycerides, vegetable oils, hydrogenated vegetable oils, and sterols.

32. The pharmaceutical composition of claim 31, wherein the reaction mixture is a transesterification product of a polyol and at least one member of the group consisting of fatty acids, glycerides, vegetable oils, hydrogenated vegetable oils, and sterols.

33. The pharmaceutical composition of claim 31, wherein the polyol is selected from the group consisting of polyethylene glycol, sorbitol, propylene glycol, pentaerythritol, a saccharide, and mixtures thereof.

34. The pharmaceutical composition of claim 24, wherein the hydrophobic surfactant is selected from the group consisting of myristic acid; oleic acid; lauric acid; stearic acid; palmitic acid; PEG 1-4 stearate; PEG 2-4 oleate; PEG-4 dilaurate; PEG-4 dioleate; PEG-4 distearate; PEG-6 dioleate; PEG-6 distearate; PEG-8 dioleate; PEG 3-16 castor oil; PEG 5-10 hydrogenated castor oil; PEG 6-20 corn oil; PEG 6-20 almond oil; PEG-6 olive oil; PEG-6 peanut oil; PEG-6 palm kernel oil; PEG-6 hydrogenated palm kernel oil; PEG-4 capric/caprylic triglyceride, mono, di, tri, tetra esters of vegetable oil and sorbitol; pentaerythrityl di, tetra stearate, isostearate, oleate, caprylate, or caprate; polyglyceryl 2-4 oleate, stearate, or isostearate; polyglyceryl 4-10 pentaoleate; polyglyceryl-3 dioleate; polyglyceryl-6 dioleate; polyglyceryl-10 trioleate; polyglyceryl-3 distearate; propylene glycol mono- or diesters of a $C_6$ to $C_{22}$ fatty acid; monoglycerides of a $C_6$ to $C_{22}$ fatty acid; acetylated monoglycerides of a $C_6$ to $C_{22}$ fatty acid; diglycerides of $C_6$ to $C_{22}$ fatty acids; lactic acid esters of monoglycerides; lactic acid esters of diglycerides; cholesterol; phytosterol; PEG 5-20 soya sterol; PEG-6 sorbitan tetra, hexastearate; PEG-6 sorbitan tetraoleate; sorbitan monolaurate; sorbitan monopalmitate; sorbitan mono, trioleate; sorbitan mono, tristearate; sorbitan monoisostearate; sorbitan sesquioleate; sorbitan sesquistearate; PEG 2-5 oleyl ether; POE 2-4 lauryl ether; PEG-2 cetyl ether; PEG-2 stearyl ether; sucrose distearate; sucrose dipalmitate; ethyl oleate; isopropyl myristate; isopropyl palmitate; ethyl linoleate; isopropyl linoleate; poloxamers; cholic acid; ursodeoxycholic acid; glycocholic acid; taurocholic acid; lithocholic acid; deoxycholic acid; chenodeoxycholic acid; and mixtures thereof.

35. The pharmaceutical composition of claim 24, wherein the hydrophobic surfactant is selected from the group consisting of oleic acid; lauric acid; glyceryl monocaprate; glyceryl monocaprylate; glyceryl monolaurate; glyceryl monooleate; glyceryl dicaprate; glyceryl dicaprylate; glyceryl dilaurate; glyceryl dioleate; acetylated monoglycerides; propylene glycol oleate; propylene glycol laurate; polyglyceryl-3 oleate; polyglyceryl-6 dioleate; PEG-6 corn oil; PEG-20 corn oil; PEG-20 almond oil; sorbitan monooleate; sorbitan monolaurate; POE-4 lauryl ether; POE-3 oleyl ether; ethyl oleate; poloxamers; cholic acid; ursodeoxycholic acid; glycocholic acid; taurocholic acid; lithocholic acid; deoxycholic acid; chenodeoxycholic acid; and mixtures thereof.

36. The pharmaceutical composition of claim 1, wherein the polysaccharide drug is selected from glucosamine, glycosaminoglycans, dextran, xylan, pentasaccharide, polygalacturonic acid, polymannuronic acid, chitin, pharmaceutically acceptable salts, esters or other derivatives thereof, and combinations of any of the foregoing.

37. The pharmaceutical composition of claim 1, wherein the polysaccharide drug is a glycosaminoglycan.

38. The pharmaceutical composition of claim 37, wherein the glycosaminoglycan is selected from heparin, heparan, chondroitin, dermatan, hyaluronic acid and pharmaceutically acceptable salts thereof.

39. The pharmaceutical composition of claim 37, wherein the glycosaminoglycan is selected from heparin, low molecular weight heparin, heparin sodium, heparan, heparan sulfate, and pharmaceutically acceptable salts of any of the foregoing formed with metallic cations or organic bases.

40. The pharmaceutical composition of claim 39, wherein the polysaccharide drug is low molecular weight heparin.

41. The pharmaceutical composition of claim 40, wherein the low molecular weight heparin is selected from the group consisting of enoxaparin, dalteparin, gammaparin, nadroparin, tinzaparin, certoparin, reviparin, pamaparin, and mixtures thereof.

42. The pharmaceutical composition of claim 39, wherein the polysaccharide drug is heparin sodium.

43. The pharmaceutical composition of claim 39, wherein the polysaccharide drug is heparan.

44. The pharmaceutical composition of claim 39, wherein the polysaccharide drug is heparan sulfate.

45. The pharmaceutical composition of claim 1, wherein the surfactants are present in amounts such that the triglyceride can be present in an amount greater than the amount of the triglyceride that remains solubilized in an aqueous dispersion of the triglyceride and a carrier having only one surfactant, the surfactant being hydrophilic, and having the same total surfactant concentration.

46. The pharmaceutical composition of claim 22, wherein the surfactants are present in amounts such that the triglyceride can be present in an amount greater than the amount of the triglyceride that remains solubilized in an aqueous dispersion of the triglyceride and a carrier having only one surfactant, the surfactant being hydrophilic, and having the same total surfactant concentration.

47. The pharmaceutical composition of claim 23, wherein the surfactants are present in amounts such that the triglyceride can be present in an amount greater than the amount of the triglyceride that remains solubilized in an aqueous dispersion of the triglyceride and a carrier having a hydrophilic surfactant but not having a hydrophobic surfactant, and having the same total surfactant concentration.

48. The pharmaceutical composition of claim 1, wherein the triglyceride and surfactants are present in amounts such that upon mixing with an aqueous medium in an aqueous medium to carrier ratio of about 10:1 by weight, the carrier forms a clear aqueous dispersion.

49. The pharmaceutical composition of claim 1, wherein the absorbance of the carrier is less than about 0.2.

50. The pharmaceutical composition of claim 1, wherein the absorbance of the carrier is less than about 0.1.

51. The pharmaceutical composition of claim 1, which fuirther comprises a solubilizer.

52. The pharmaceutical composition of claim 51, wherein the solubilizer is selected from the group consisting of alcohols, polyols, amides, esters, propylene glycol ethers and mixtures thereof.

53. The pharmaceutical composition of claim 52, wherein the alcohol or polyol is selected from the group consisting of ethanol, isopropanol, butanol, benzyl alcohol, ethylene glycol, propylene glycol, butanediols and isomers thereof, glycerol, pentaerythritol, sorbitol, mannitol, transcutol, maltol, maltodextrins, dimethyl isosorbide, polyethylene glycol, polypropylene glycol, polyvinylalcohol, hydroxypropyl methylcellulose and other cellulosic polymers, cyclodextrins, and mixtures thereof.

54. The pharmaceutical composition of claim 52, wherein the amide is selected from the group consisting of 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide, polyvinylpyrrolidone, and mixtures thereof.

55. The pharmaceutical composition of claim 52, wherein the ester is selected from the group consisting of ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof, and mixtures thereof.

56. The pharmaceutical composition of claim 51, wherein the solubilizer is selected from the group consisting of ethanol, isopropanol, butanol, benzyl alcohol, ethylene glycol, propylene glycol, butanediol and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulosic polymers, cyclodextrins, ethyl propionate, tributylcitrate, acetyl triethylcitrate, acetyl tributyl citrate, triethylcitrate, ethyl oleate, ethyl caprylate, ethyl butyrate, triacetin, propylene glycol diacetate, ε-caprolactone and isomers thereof, δ-valerolactone and isomers thereof, β-butyrolactone and isomers thereof, 2-pyrrolidone, 2-piperidone, ε-caprolactam, N-methylpyrrolidone, N-ethylpyrrolidone, N-hydroxyethyl pyrrolidone, N-octylpyrrolidone, N-laurylpyrrolidone, dimethylacetamide, polyvinylpyrrolidone, glycofurol, methoxy PEG, and mixtures thereof.

57. The pharmaceutical composition of claim 51, wherein the solubilizer is selected from the group consisting of ethanol, isopropanol, benzyl alcohol, ethylene glycol, propylene glycol, 1,3-butanediol, glycerol, pentaerythritol, sorbitol, glycofurol, transcutol, dimethyl isosorbide, polyethylene glycol, polyvinylalcohol, hydroxypropyl methylcellulose, methylcellulose, ethylcellulose, hydroxypropylcyclodextrins, sulfobutyl ether derivatives of cyclodextrins, ethyl propionate, tributylcitrate, triethylcitrate, ethyl oleate, ethyl caprylate, triacetin, β-butyrolactone and isomers thereof, 2-pyrrolidone, N-methylpyrrolidone, N-ethylpyrrolidone, N-hydroxyethylpyrrolidone, N-octylpyrrolidone, N-laurylpyrrolidone, dimethylacetamide, polyvinylpyrrolidone, and mixtures thereof.

58. The pharmaceutical composition of claim 51, wherein the solubilizer is selected from the group consisting of triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-600, glycofurol, transcutol, propylene glycol, dimethyl isosorbide and mixtures thereof.

59. The pharmaceutical composition of claim 51, wherein the solubilizer is selected from the group consisting of triacetin, ethanol, polyethylene glycol 400, glycofurol, propylene glycol and mixtures thereof.

60. The pharmaceutical composition of claim 1, which further comprises at least one additive selected from the group consisting of an antioxidant, a bufferant, an antifoaming agent, a detackifier, a preservative, a chelating agent, a viscomodulator, a tonicifier, a flavorant, a colorant, an odorant, an opacifier, a suspending agent, a binder, a filler, a plasticizer, and a lubricant.

61. The pharmaceutical composition of claim 1, which further comprises an amount of an enzyme inhibiting agent sufficient to at least partially inhibit enzymatic degradation of the polysaccharide drug.

62. The pharmaceutical composition of claim 61, wherein the enzyme inhibitor is solubilized or suspended in the carrier.

63. The pharmaceutical composition of claim 1, which further comprises an aqueous medium comprising water, an aqueous palatable diluent or an aqueous beverage.

64. The pharmaceutical composition of claim 63, wherein the polysaccharide drug is provided to the composition in the aqueous medium.

65. The pharmaceutical composition of claim 63, wherein the aqueous medium further comprises an amount of an enzyme inhibiting agent sufficient to at least partially inhibit enzymatic degradation of the polysaccharide drug.

66. The pharmaceutical composition of claim 1 in the form of a preconcentrate in a liquid, semi-solid, or solid form, or as an aqueous or organic diluted preconcentrate.

67. The pharmaceutical composition of claim 1, wherein the polysaccharide drug is solubilized in the carrier.

68. The pharmaceutical composition of claim 1, wherein the polysaccharide drug is suspended in the carrier.

69. The pharmaceutical composition of claim 1, wherein the polysaccharide drug is partially suspended and partially solubilized in the carrier.

70. The pharmaceutical composition of claim 1, wherein the composition is substantially free of water.

71. A dosage form comprising the pharmaceutical composition of claim 1 processed by a technique selected from the group consisting of lyophilization, encapsulation, extruding, compression, melting, molding, spraying, coating, comminution, mixing, homogenization, sonication, granulation, and combinations thereof.

72. A dosage form comprising the pharmaceutical composition of claim 1, wherein the dosage form is selected from the group consisting of a pill, capsule, caplet, tablet, granule, bead and powder.

73. The dosage form of claim 72, comprising a capsule.

74. The dosage form of claim 73, wherein the capsule is selected from the group consisting of a starch capsule, a cellulosic capsule, a hard gelatin capsule and a soft gelatin capsule.

75. The dosage form of claim 74, wherein the capsule is selected from the group consisting of a starch capsule, a cellulosic capsule, and a soft gelatin capsule.

76. The dosage form of claim 72, which further comprises an enteric coating, a seal coating, or both.

77. A dosage form comprising the pharmaceutical composition of claim 1, wherein the dosage form is selected from the group consisting of a solution, suspension, emulsion, cream, ointment, lotion, suppository, spray, aerosol, paste, gel, drops, douche, ovule, wafer, troche, cachet, syrup and elixir.

78. A dosage form comprising a multiparticulate carrier coated onto a substrate with the pharmaceutical composition of claim 1.

79. The dosage form of claim 78, wherein the substrate is selected from the group consisting of a particle, a granule and a bead, and is formed of a material selected from the group consisting of the polysaccharide drug, a pharmaceutically acceptable material, and a mixture thereof.

80. The dosage form of claim 78, wherein the multiparticulate carrier is coated with a coating selected from the group consisting of an enteric coating, a seal coating, and a mixture thereof.

81. The dosage form of claim 77, wherein the dosage form is further processed by a technique selected from the group consisting of encapsulation, compression, extrusion or molding.

82. The dosage form of claim 77, wherein the dosage form is encapsulated in a capsule selected from the group consisting of a starch capsule, a cellulosic capsule, a hard gelatin capsule, and a soft gelatin capsule.

83. The dosage form of claim 82, wherein the dosage form is encapsulated in a capsule selected from the group consisting of a starch capsule, a cellulosic capsule, and a soft gelatin capsule.

84. A pharmaceutical composition comprising:
(a) a carrier comprising a triglyceride and at least two surfactants, at least one of the surfactants being hydrophilic; and
(b) a therapeutically effective amount of a polysaccharide drug, wherein the triglyceride and the surfactants are present in amounts such that upon mixing with an aqueous medium in an aqueous medium to carrier ratio of about 100:1 by weight, the carrier forms an aqueous dispersion having an average particle size less than about 200 nm.

85. A pharmaceutical composition comprising:
(a) a carrier comprising a triglyceride, at least one hydrophilic surfactant, and at least one hydrophobic surfactant; and
(b) a therapeutically effective amount of a polysaccharide drug, wherein the triglyceride and surfactants are present in amounts such that upon mixing with an aqueous medium in an aqueous medium to carrier ratio of about 100:1 by weight, the carrier forms a clear aqueous dispersion having an absorbance of less than about 0.3 at 400 nm.

86. A pharmaceutical composition comprising:
(a) a therapeutically effective amount of a polysaccharide drug; and
(b) a carrier comprising a triglyceride and at least two surfactants, at least one of the surfactants being hydrophilic, wherein the triglyceride and surfactants are present in amounts such that upon mixing with an aqueous medium in an aqueous medium to carrier ratio of about 100:1 by weight, the carrier forms a clear aqueous dispersion having an absorbance of less than about 0.3 at 400 nm, and wherein the triglyceride is present in an amount greater than the amount of the triglyceride that remains solubilized in an aqueous dispersion of the triglyceride and a carrier having only one surfactant, the surfactant being hydrophilic, and having the same total surfactant concentration.

87. A pharmaceutical composition comprising:
(a) a therapeutically effective amount of a polysaccharide drug; and
(b) a carrier comprising a triglyceride, at least one hydrophilic surfactant, and at least one hydrophobic surfactant, wherein the triglyceride and surfactants are present in amounts such that upon mixing with an aqueous medium in an aqueous medium to carrier ratio of about 100:1 by weight, the carrier forms a clear aqueous dispersion having an absorbance of less than about 0.3 at 400 nm, and wherein the triglyceride is present in an amount greater than the amount of the triglyceride that remains solubilized in an aqueous dispersion of the triglyceride and one surfactant, the surfactant being hydrophilic, and having the same total surfactant concentration.

88. A method of treating a mammalian patient with a polysaccharide drug, the method comprising:
(a) providing an initial dosage form of a pharmaceutical composition having a carrier comprising a triglyceride and at least two surfactants, at least one of the surfactants being hydrophilic wherein the triglyceride and surfactants are present in amounts such that upon mixing with an aqueous medium in an aqueous medium to carrier ratio of about 100:1 by weight, the carrier forms a clear aqueous dispersion having an absorbance of less than about 0.3 at 400 nm.
(b) providing a polysaccharide drug; and
(c) administering said dosage form to said animal.

89. The method of claim 88, further comprising providing at least one additional therapeutic agent selected from the group consisting of platelet aggregation inhibitors, platelet antagonists, anticoagulants, fibrinolytic agents and combinations thereof.

90. The method of claim 88, further comprising providing at least one additional therapeutic agent selected from the group consisting of aspirin, clopidrogel, ticlidopine, dipyridamole, coumarins, COX inhibitors and combinations thereof.

91. The method of claim 88, wherein the polysaccharide drug is in the initial dosage form.

92. The method of claim 88, wherein the polysaccharide drug is in a second dosage form.

93. The method of claim 91, wherein the at least one additional therapeutic agent is in the initial dosage form.

94. The method of claim 92, wherein the at least one additional therapeutic agent is in the second dosage form.

95. The method of claim 91, wherein the at least one additional therapeutic agent is in a second dosage form.

96. The method of claim 92, wherein the at least one additional therapeutic agent is in the initial dosage form.

97. The method of claim 88, wherein the dosage form is processed by a technique selected from the group consisting of lyophilization, encapsulation, extruding, compression, melting, molding, spraying, coating, comminution, mixing, homogenization, sonication, granulation, and combinations thereof.

98. The method of claim 88, wherein the dosage form is selected from the group consisting of a pill, capsule, caplet, tablet, granule, bead and powder.

99. The method of claim 98, wherein the dosage from is a capsule.

100. The method of claim 99, wherein the capsule is selected from the group consisting of a starch capsule, a cellulosic capsule, a hard gelatin capsule and a soft gelatin capsule.

101. The method of claim 100, wherein the capsule is selected from the group consisting of a starch capsule, a cellulosic capsule, and a soft gelatin capsule.

102. The method of claim 99, wherein the capsule further comprises a coating selected from the group consisting of an enteric coating, a seal coating, and a combination thereof.

103. The method of claim 88, wherein the dosage form is selected from the group consisting of a solution, suspension, emulsion, cream, ointment, lotion, suppository, spray, aerosol, paste, gel, drops, douche, ovule, wafer, troche, cachet, syrup and elixir.

104. The method of claim 88, wherein the dosage form comprises a multiparticulate carrier coated onto a substrate with the pharmaceutical composition.

105. The method of claim 104, wherein the substrate is selected from the group consisting of a particle, a granule and a bead, and is formed of a material selected from the group consisting of the polysaccharide drug, a pharmaceutically acceptable material and a mixture thereof.

106. The method of claim 104, wherein the multiparticulate carrier is coated with a coating selected from the group consisting of an enteric coating, a seal coating, and a combination thereof.

107. The method of claim 104, wherein the dosage form is further processed by encapsulation, compression, extrusion or molding.

108. The method of claim 104, wherein the dosage form is a starch capsule, a cellulosic capsule, a hard gelatin capsule, or a soft gelatin capsule.

109. The method of claim 104, wherein the dosage form is a starch capsule, a cellulosic capsule, or a soft gelatin capsule.

110. The method of claim 88, wherein the polysaccharide drug is provided by solubilizing the therapeutic agent in the triglyceride, in the carrier, or in both the triglyceride and the carrier.

111. The method of claim 88, wherein the polysaccharide drug is provided separately from the dosage form of the pharmaceutical composition.

112. The method of claim 88, wherein the dosage form is administered by a route selected from the group consisting of oral, parenteral, buccal, topical, transdermal, ocular, pulmonary, vaginal, rectal and transmucosal.

113. The method of claim 88, wherein the mammalian patient is a human.

114. The method of claim 88, wherein the polysaccharide drug is solubilized in the carrier.

115. The method of claim 88, wherein the polysaccharide drug is suspended in the carrier.

116. The method of claim 88, wherein the composition is substantially free of water.

117. The method of claim 88, wherein the mammalian patient is in need of the prevention of blood coagulation or the treatment of thrombosis.

118. A method of treating a mammalian patient with a polysaccharide drug, the method comprising:
(a) providing a dosage form of a pharmaceutical composition having a carrier comprising a triglyceride and at least two surfactants, at least one of the surfactants being hydrophilic, wherein the triglyceride and surfactants are present in amounts such that upon mixing with an aqueous medium in an aqueous medium to carrier ratio of about 100:1 by weight, the carrier forms a clear aqueous dispersion having an absorbance of less than about 0.3 at 400 nm; and
(b) administering the dosage form to the mammalian patient.

119. The method of claim 118, wherein the mammalian patient is in need of prevention of blood coagulation or treatment of thrombosis.

120. A method for increasing the loading capacity of a pharmaceutical composition comprising the steps of:
  providing a pharmaceutical composition comprised of
    (a) a carrier comprising a triglyceride and a first surfactant, and
    (b) a therapeutically effective amount of a polysaccharide drug; and
  adding an absorption-enhancing amount of a second surfactant to the pharmaceutical composition, the second surfactant comprising a hydrophobic surfactant, wherein said aborption-enhancing amount is effective to increase the loading capacity of the pharmaceutical composition, wherein the triglyceride and the combined surfactants are present in amounts such that upon mixing with an aqueous medium in an aqueous medium to triglyceride and surfactants ratio of about 100:1 by weight, the triglyceride and surfactants form a clear aqueous dispersion.

121. The method of claim 120, wherein the clear aqueous dispersion formed has an average particle size of less than about 200 nm.

122. The method of claim 120, wherein the clear aqueous dispersion formed has an absorbance of less than about 0.3 at 400 nm.

* * * * *